US005681942A

United States Patent [19]
Buchwald et al.

[11] Patent Number: 5,681,942
[45] Date of Patent: Oct. 28, 1997

[54] FANCONI ANEMIA TYPE C GENE

[75] Inventors: Manuel Buchwald, Toronto; Craig A. Strathdee, Nepean, both of Canada; Rachel Wevrick, Menlo Park, Calif.; Christopher George Porter Mathew, London, England

[73] Assignees: HSC Research & Development Limited Partnership, Toronto, Canada; The United Medical and Dental Schools of Guy's and St. Thomas's Hospitals, London, England

[21] Appl. No.: 441,430

[22] Filed: May 15, 1995

Related U.S. Application Data

[63] Continuation of Ser. No. 3,963, Jan. 15, 1993, abandoned, which is a continuation-in-part of Ser. No. 918,313, Jul. 21, 1992, abandoned, which is a continuation-in-part of Ser. No. 876,285, Apr. 29, 1992, abandoned.

[51] Int. Cl.$^6$ .................................................. C07H 21/04
[52] U.S. Cl. .................. 536/23.5; 536/24.2; 536/24.31; 536/24.33
[58] Field of Search .......................... 536/23.5, 24.2, 536/24.31, 24.33

[56] References Cited

PUBLICATIONS

Strathdee et al. (1992, Apr. 30) Nature 356: 763–767.
Auerbach et al., "Complementation Studies in Fanconi Anemia," in *Fanconi Anemia, Clinical, Cytogenetic and Experimental Aspects* (Schroeder–Kurth, et al., eds.) pp. 213–225, Springer–Verlag, Berlin (1989).
Auerbach, "A Test For Fanconi's Anemia", *Blood* 72:366–367 (1988).
Auerbach et al., "International Fanconi Anemia Registry: Relation of Clinical Symptoms to Diepoxybutane Sensitivity," *Blood* 73:391–396 (1989).
Buchwald et al., "Complementation and Gene Transfer Studies in Fanconi Anemia," *Fanconi Anemia, Clinical, Cytogenetic and Experimental Aspects* (Schroeder–Kurth, et al., eds.) pp. 226–235, Springer–Verlag, Berlin (1989).
Buchwald et al., "Studies of gene transfer and reversion to mitomycin C resistance in Fanconi anemia cells," *Mutation Research* 184:153–159 (1987).
Diatloff–Zito et al., "Partial complementation of the Fanconi anemia defect upon transfection by heterologous DNA," *Human Genetics* 86:151–161 (1990).
Digweed et al., "Complementation Studies in Fanconi Anemia Using Cell Fusion and Microinjection of mRNA," in *Fanconi Anemia, Clinical, Cytogenetic and Experimental Aspects* (Schroeder–Kurth, et al., eds.) pp. 236–254 (1989).
Duckworth–Rysiecki et al., "Characterization of a Simian virus 40–transformed Fanconi anemia fibroblast cell line," *Mutation Research* 166:207–214 (1986).
Duckworth–Rysiecki et al., "Identification of Two Complementation Groups in Fanconi Anemia," *Somatic Cell and Molecular Genetics* 11:35–41 (1985).
German et al., "A Test for Fanconi's Anemia," *Blood* 69:1637–1641 (1987).
Gök, M. and Wunder, E., "Microinjection of normal cell extracts into Fanconi anemia fibroblasts corrects defective scheduled DNA synthesis recovery after 8–methoxypsoralen plus UVa treatment," *Human Genetics* 75:350–355 (1987).
Ishida, R. and Buchwald, M., "Susceptibility of Fanconi's Anemia Lymphoblasts to DNA–cross–linking and Alkylating Agents," *Cancer Research* 42:4000–4006 (1982).
Mann et al., "Fanconi Anemia: Evidence for Linkage Heterogeneity on Chromosome 20q," *Genomics* 9:329–337 (1991).
Moustacchi et al., "Two complementation groups of Fanconi's anemia differ in their phenotypic response to a DNA–crosslinking treatment," *Human Genetics* 75:45–47 (1987).
Rosselli, F. and Moustacchi, E., "Cocultivation of Fanconi anemia cells and of mouse lymphoma mutants leads to inter–species complementation of chromosomal hypersensitivity to DNA cross–linking agents," *Human Genetics* 84:517–521 (1990).
Strathdee et al., "Cloning of cDNAs for Fanconi's anaemia by functional complementation," *Nature* 356:763–767 (Apr. 1992).
Strathdee et al., "Cloning of cDNAs for Fanconi anaemia by functional complementation," *Nature* 358:434 (Jul. 1992).
Tanaka et al., "Analysis of a human DNA excision repair gene involved in group A xeroderma pigmentosum and containing a zinc–finger domain," *Nature* 348:73–76 (1990).
Tanaka et al., "Molecular cloning of a mouse DNA repair gene that complements the defect of group–A xeroderma pigmentosum," *Proc. Natl. Acad. Sci. USA* 86:5512–5516 (1989).
Wunder et al., "Cellular Effects of Fanconi Anemia Genes and Their Correction by Microinjection," in *Fanconi Anemia, Clinical, Cytogenetic and Experimental Aspects* (Schroeder–Kurth, et al., eds.) pp. 181–195 (1989).
Teitz et al, "Isolation by polymerase chain reaction of cDNA whose product partially complements the ultraviolet sensitivity of xeroderma pigmentosum group C cells," *Gene* 87:295–298 (1990).
Shelley et al., "The Promoter of the CD11b Gene Directs Myeloid–Specific and Developmentally Regulated Express," *PNAS* 88:10529–9 (1991).
Martin–Gallardo et al., "Automated DNA Sequencing and Analysis of 106 Kilobases From Human Chromosome 19q13.3," *Nature Genet.* 1:34–39 (1992).

*Primary Examiner*—Lisa B. Arthur
*Attorney, Agent, or Firm*—Klarquist Sparkman Campbell Leigh & Whinston, LLP

[57] ABSTRACT

Fanconi Anemia is a human genetic disease, the precise cause of which is, to date, unknown. This invention provides an isolated human cDNA molecule which is able to specifically complement, in one type of Fanconi Anemia, (type C) the characteristic defect exhibited by cells derived from patients with Fanconi Anemia. The genomic gene from which this cDNA is derived is also provided as is the sequence of the protein encoded by this gene. Mutations in this gene are proposed to underlie Fanconi Anemia Type C. Diagnostic and therapeutic applications which derive from this work are described. The murine homolog of the human cDNA is also provided.

14 Claims, 22 Drawing Sheets

```
Exon 1                *                   *                   *
  1 ACTGCTGACACGTGTGCGCGCGCGCGGCTCCACTGCCGGGCGACCGCGGGAAAATTCCAA AAAAACTCAAAAAGCCAATACGAGGCAAAGCCAAATTTTCAAGCCACAGATCCCGGGCGG
            Exon 1A     GAGCCCCCGGAGAGGCGGGAGCGGTGTTGGCGTTTTGG 121 TGGCTTCCTTTCCGCCACTGCCCAAACTGCTGAAGCAGCTCCCGCGAGGACCACCCGATT
    TTCTTTTTTGTTCATTGAGCGCAGGCAGCTATGTCTTCTTCAAAGGAGAGGAGCAAAGC

TAATGTGTGCCGACCATTTCCTTCAGTGCTGGACAGGCTGCTGTGAAGGGACATCACCTT

241 TTCGCTTTTTCCAAGATGGCTCAAGATTCAGTAGATCTTTCTTGTGATTATCAGTTTTGG
                 M  A  Q  D  S  V  D  L  S  C  D  Y  Q  F  W

ATGCAGAAGCTTTCTGTATGGGATCAGGCTTCCACTTTGGAAACCCAGCAAGACACCTGT
    M  Q  K  L  S  V  W  D  Q  A  S  T  L  E  T  Q  Q  D  T  C  35

361 CTTCACGTGGCTCAGTTCCAGGAGTTCCTAAGGAAGATGTATGAAGCCTTGAAAGAGATG
    L  H  V  A  Q  F  Q  E  F  L  R  K  M  Y  E  A  L  K  E  M

GATTCTAATACAGTCATTGAAAGATTCCCCACAATTGGTCAACTGTTGGCAAAAGCTTGT
    D  S  N  T  V  I  E  R  F  P  T  I  G  Q  L  L  A  K  A  C   75

481 TGGAATCCTTTTATTTTAGCATATGATGAAAGCCAAAAAATTCTAATATGGTGCTTATGT
    W  N  P  F  I  L  A  Y  D  E  S  Q  K  I  L  I  W  C  L  C

TGTCTAATTAACAAAGAACCACAGAATTCTGGACAATCAAAACTTAACTCCTGGATACAG
    C  L  I  N  K  E  P  Q  N  S  G  Q  S  K  L  N  S  W  I  Q   115

601 GGTGTATTATCTCATATACTTTCAGCACTCAGATTTGATAAAGAAGTTGCTCTTTTCACT
    G  V  L  S  H  I  L  S  A  L  R  F  D  K  E  V  A  L  F  T

CAAGGTCTTGGGTATGCACCTATAGATTACTATCCTGGTTTGCTTAAAAATATGGTTTTA
    Q  G  L  G  Y  A  P  I  D  Y  Y  P  G  L  L  K  N  M  V  L   155

721 TCATTAGCGTCTGAACTCAGAGAGAATCATCTTAATGGATTTAACACTCAAAGGCGAATG
    S  L  A  S  E  L  R  E  N  H  L  N  G  F  N  T  Q  R  R  M

GCTCCCGAGCGAGTGGCGTCCCTGTCACGAGTTTGTGTCCCACTTATTACCCTGACAGAT
    A  P  E  R  V  A  S  L  S  R  V  C  V  P  L  I  T  L  T  D   195

841 GTTGACCCCCTGGTGGAGGCTCTCCTCATCTGTCATGGACGTGAACCTCAGGAAATCCTC
    V  D  P  L  V  E  A  L  L  I  C  H  G  R  E  P  Q  E  I  L

CAGCCAGAGTTCTTTGAGGCTGTAAACGAGGCCATTTTGCTGAAGAAGATTTCTCTCCCC
    Q  P  E  F  F  E  A  V  N  E  A  I  L  L  K  K  I  S  L  P   235
```

FIG. 6A

```
 961 ATGTCAGCTGTAGTCTGCCTCTGGCTTCGGCACCTTCCCAGCCTTGAAAAAGCAATGCTG
      M  S  A  V  V  C  L  W  L  R  H  L  P  S  L  E  K  A  M  L
     CATCTTTTTGAAAAGCTAATCTCCAGTGAGAGAAATTGTCTGAGAAGGATCGAATGCTTT  275
      H  L  F  E  K  L  I  S  S  E  R  N  C  L  R  R  I  E  C  F
1081 ATAAAAGATTCATCGCTGCCTCAAGCAGCCTGCCACCCTGCCATATTCCGGGTTGTTGAT
      I  K  D  S  S  L  P  Q  A  A  C  H  P  A  I  F  R  V  V  D
     GAGATGTTCAGGTGTGCACTCCTGGAAACCGATGGGGCCCTGGAAATCATAGCCACTATT  315
      E  M  F  R  C  A  L  L  E  T  D  G  A  L  E  I  I  A  T  I
1201 CAGGTGTTTACGCAGTGCTTTGTAGAAGCTCTGGAGAAAGCAAGCAAGCAGCTGCGGTTT
      Q  V  F  T  Q  C  F  V  E  A  L  E  K  A  S  K  Q  L  R  F
     GCACTCAAGACCTACTTTCCTTACACTTCTCCATCTCTTGCCATGGTGCTGCTGCAAGAC  355
      A  L  K  T  Y  F  P  Y  T  S  P  S  L  A  M  V  L  L  Q  D
1321 CCTCAAGATATCCCTCGGGGACACTGGCTCCAGACACTGAAGCATATTTCTGAACTGCTC
      P  Q  D  I  P  R  H  G  W  L  Q  T  L  K  H  I  S  E  L  L
     AGAGAAGCAGTTGAAGACCAGACTCATGGGTCCTGCGGAGGTCCCTTTGAGAGCTGGTTC  395
      R  E  A  V  E  D  Q  T  H  G  S  C  G  G  P  F  E  S  W  F
1441 CTGTTCATTCACTTCGGAGGATGGGCTGAGATGGTGGCAGAGCAATTACTGATGTCGGCA
      L  F  I  H  F  G  G  W  A  E  M  V  A  E  Q  L  L  M  S  A
     GCCGAACCCCCCACGGCCCTGCTGTGGCTCTTGGCCTTCTACTACGGCCCCCGTGATGGG  435
      A  E  P  P  T  A  L  L  W  L  L  A  F  Y  Y  G  P  R  D  G
1561 AGGCAGCAGGCACAGACTATGGTCCAGGTGAAGGCCGTGCTGGGCCACCTCCTGGCAATG
      R  Q  Q  A  Q  T  M  V  Q  V  K  A  V  L  G  H  L  L  A  M
     TCCAGAAGCAGCAGCCTCTCAGCCCAGGACCTGCAGACGGTAGCAGGACAGGGCACAGAC  476
      S  R  S  S  S  L  S  A  Q  D  L  Q  T  V  A  G  Q  G  T  D
1684 ACAGACCTCAGAGCTCCTGCACAACAGCTGATCAGGCACCTTCTCCTCAACTTCCTGCTC
      T  D  L  R  A  P  A  Q  Q  L  I  R  H  L  L  L  N  F  L  L
     TGGGCTCCTGGAGGCCACACGATCGCCTGGGATGTCATCACCCTGATGGCTCACACTGCT  516
      W  A  P  G  G  H  T  I  A  W  D  V  I  T  L  M  A  H  T  A
1804 GAGATAACTCACGAGATCATTGGCTTTCTTGACCAGACCTTGTACAGATGGAATCGTCTT
      E  I  T  H  E  I  I  G  F  L  D  Q  T  L  Y  R  W  N  R  L
     GGCATTGAAAGCCCTAGATCAGAAAAAACTGGCCCGAGAGCTCCTTAAAGAGCTGCGAACT  556
      G  I  E  S  P  R  S  E  K  L  A  R  E  L  L  K  E  L  R  T
```

FIG. 6B

1924 CAAGTCTAGAAGGCACGCAGGCCGTGTGGGTGCCCGGCGTGAGGGATCAGGCTCGCCAGG
     Q   V   -
     GCCACAGGACAGGTGATGACCTGTGGCCACGCATTTGTGGAGTAAGTGCCCTCGCTGGGC
2044 TGTGAGAATGAGCTGTACACATCTTGGGACAATCTGCTAGTATCTATTTTACAAAATGCA
     GAGCCAGGTCCCTCAGCCCAGACTCAGTCAGACATGTTCACTAATGACTCAAGTGAGCTT
2164 CGGTACTCCTGGTGCCCGCCCGGCCAGACCGTCAGCTTGATAATTACTAAAGCAAAGGCC
     TGGGTGGGAGAACAGGTTTCTAGTTTTTACCCAAGTCAAGCTGCACATCTATTATTTAAA
2284 AATTCAAAGTCTTAGAACCAAGAATTTGGTCATGAACC ATTAAA GAATTTAGAGAGAACT
     TAGCT CTTTTT AGACTCTTTTTAGGAGTCAGGGATCTGGGATAAAGCCACACTGTCTTGC
          Poly(A) Tail
2404 TGTATGGAGAAATTCTTCAAGGGGAGTCAGGGTCCCTCAGGCTTCCCTTGTGTCTCCCTG
     GACCTGCCTGACAGGCCACAGGAGCAGACAGCACACCCAAGCCCGGGCCTCCGGCACACT
2524 CTTTCCACTCTGTATTTGCTAAATGATGCTAACTGCTACCAAAAGGCCCTTGGGACATCA
     GAGGAGCCGGCAGCGAAGGTAGAGGATGTGTTCCAGAAACATTAGAAGGCAGGATTAATT
2644 CAGTTAGTTAGTCTCTTGTTAAATGGAAATGGGAATTGGAAATTCCTGATAAAGAATTGG
     CCTGGCTGGGTGCAGTGGCTCACACCTGTGATCCCAGCACTTTGGGAGGCCAAGGCAGGG
2764 GGATTACTTCAGCCCAGGAGTTCCAGACTGCCTGGCTAACATGGCAATACCCTATCTCTA
     CTAAAAATACAAAAATTATCGGGGTGCAATGGCATGCATCTGTAACCCAGCTATTCAAGA
2884 GGCTGAGGCATGAGGATCTCTTGAACCCGGGAGGTGGGAGTTGTAGTGAGCCGAGATCAT
     GACACTGCACTCCAGCCTGGGCAACAGAGCGAGACCATCTCTTAAAAAAGGCATTGTTA
3004 GTGTAACTCAAGGTTAACATTTATTTCATGTCAGTACAGGGTGCTTTTTCCTTTCAGGGA
     CATTCTGGAATTGTATTGGTTGTACATTCTTTTGTGTCTATTCTGTTTGTCAAGTGAGTC
3124 AAGACT GCTTTTGTCCATTTTGATT GTGTGT ATTAGTCTGAGTCTTGGCTCCGTTTTG
                              Poly(A) Tail
     AGGTATGAGCAAAGTTTTGCTGGATAGAGTTAACCTTTAGGGAAATTCCTTATTTTGGTA

FIG. 6C

```
3244 TGTGGCAATGCTAATAGATCCACTGAAGATCTGGAAAATTCCAGGAACTTTTTCACCTGA
     GCCTTTCTTCTGAGAAATGCTGCAGTCAGAAGGGTGTGCTGGTAAAGTATTTTGGTGGCA
3364 GCTGCCATCATGGTCATTGCCTTCATATAACATGCTTCGTGCTCATGGTCATTGCCTTCA
     TATAACATGCTTCGTCCCATCATGATCCTTGCCTTCATATAACAAACATGCTTCGTCAGA
3484 GGTGTTGGGGTTGAAAAAGGAGCTGCATGCTTCACTGGAGTTGAGGGCCTCTCCTGTCTG
     ACTTTAAGCCAGAACTTGTGGCTGGGCCATGGAAGCTGTGACTCCTCTGTGGACATGGTG
3604 GCAGCAGGGAACCCCTAGAGAGAGGGGCCACTGGGACCAGGCCTCCTGTTGTGGAGGGAC
     TCCTGGGACAGTCCTCCACCCTGTCCTGTGGTCCTGTGTACAGGGTTGGCCTCTTCCTCC
3724 TCCCCTGCCAGGCCTCTGCCCATGCCCCTTCCTTCCTTCTCCTGGGACTGGTGAAGCTAG
     GCATCTGGAAGACTTCTTCCTAGCCTGGAAGCCCTGACCTCGGCCCATCTGCAGAATCTC
3844 CCAGTTCCTTCACAGCTGCCGAGTCCTCTCACGGGTGCGGTGGAGGCGGCCTTGCGGTGG
     TGCTTTCTGGGCAGCCAGGGGTTCCTGGGTGGGAGGACTGTCCCTCTGGGGACGTGGCAC
3964 TGAAGTGCCTGCTGGCTTCATGTGGCCCTTTGCCCTTTCCCAGCCTGAGAGATGCTCAAA
     GGTGGGGAGCTGGGGGAGCCACCCCTCGGCCATTCCCTCCACCTCCAAGACAGGTGGCGG
4084 CCGGGCAGGCACTCTTAAGCCCACCTCCCCCTCTTGTTGCCTTCGATTTCGGCAAAGCCT
     GGGCAGGTGCCACCGGGAAGGAATGGCATCGAGATGCTGGGCGGGGACGCGGCGTGGCGA
4204 GGGGGCTTGACGGCGTTGGCGGGGCTGGGCACAGGGGCAGCCGCAGGGAGGCAGGGATGG
     CAAGGCGTGAAGCCACCCTGGAAGGAACTGGACCAAGGTCTTCAGAGGTGCGACAGGGTC
4324 TGGAATCTGACCTTACTCTAGCAGGAGTTTTTGTAGACTCTCCCTGATAGTTTAGTTTTT
     GATAAAGCATGCTGGTAAAACCACTACCCTCAGAGAGAGCCAAAAATACAGAAGAGGCGG
4444 AGAGCGCCCCTCCAACCAGGCTGTTATTCCCCTGGACTCCGTGACATCTGTGGAATTTTT
     TAGCTCTTTAAAATCTGTAATTTGTTGTCTATTTTTTCATTCTAAATAAAACTTCAGTTT
4564 GCACCT
       └─Poly(A) Tail
```

FIG. 6D

```
    AATTCCCGCACGCGCAGTGCACTCCCTTGCGGCCGCGGGAAAATTCCAAACACGTCAAAA
    CAAAAAAGGTTCCGTGAGCTGTGCCAAGTTTTCAAGCCGCAGAAGCCGGGCGGTGGCTTC
121 TTTTCCGCCGCAGCCCAGTCTGCTGAGGCAGCTCTGGGTGAGGACCACCCGGGAAGACCG
    CCGTTTCCTGCTAGGGCAGAGAAGACTCGCGAGAACGTGCGCCCGAGTCTCAACGTGGGC
241 GAGCCGCGCTCCCGGGGGGTGGAGCTGAGGCAGGACGGCTGCTGTGAAGGGACAGTGCTG
    CTCTCAGAGATGGCTCAGGAGTCTGCAGACCTTGCTTCTGACTGTCAGTCTTGGCTGCAG
                 M  A  Q  E  S  A  D  L  A  S  D  C  Q  S  W  L  Q  16
361 AAGCTTTCTGCATGGGAACAGGCCTCTTCTGAGGAAACCCAGAAGGACACTTGTCTTCAC
    K  L  S  A  W  E  Q  A  S  S  E  E  T  Q  K  D  T  C  L  H
    TTGTCCGGGTTCCAGGAGTTCCTGAGGCAGATGTATGAAATCTTGAAGGAGATGGATTCT
    L  S  G  F  Q  E  F  L  R  Q  M  Y  E  I  L  K  E  M  D  S  57
481 GATGCAATCCTGGAAAGGTTCCCCACAATTGGTCAACTGTTGGCAAAAGCTTGTTGGAATC
    D  A  I  L  E  R  F  P  T  I  G  Q  L  L  A  K  A  C  W  N  P
    CTCTCATCTTAGCATATGATGAAAGCCAAAAAATTGTAATATGGTGCTTATGTTGTCTG
    L  I  L  A  Y  D  E  S  Q  K  I  V  I  W  C  L  C  C  L  97
601 ATGAACAAAGAACCTCGGACTTCTGCAGAGTCAGGACTTAACTCGTGGATCCGGGGTTTGT
    M  N  K  E  P  R  T  S  A  E  S  G  L  N  S  W  I  R  G  L  L
    TATCTCATGTACTTTCTGCATTCAGATTCGACATGAAAGAAGTTTGTCTTTTTTACCAAA
    S  H  V  L  S  A  F  R  F  D  M  K  E  V  C  L  F  T  K  136
721 AGTCTTGGATATGAGTCTATTGATTACTATCCTAGTTTGCTTAAAAATATGGTTTTGTCAT
    S  L  G  Y  E  S  I  D  Y  Y  P  S  L  L  K  N  M  V  L  S  L
    TAGTGTCTGAGCTCAGAGAGAGTCATCTTAATGGACTGAGCACTCAAAGTCGGATGGCT
    V  S  E  L  R  E  S  H  L  N  G  L  S  T  Q  S  R  M  A  176
841 CCTGAGCGCATGATGTCCCTGTCAGAAGTTTGTGTCCCTCTTGTCACTCTGCCTGATATGG
    P  E  R  M  M  S  L  S  E  V  C  V  P  L  V  T  L  P  D  M  E
    AACCCCTGGTAGAGGCTCTACTCACCTACCATGGACATGAGCCCCAGGAAGTCCTGGCT
    P  L  V  E  A  L  L  T  Y  H  G  H  E  P  Q  E  V  L  A  217
961 CCTGAGTTCTTCGAAGCTGTAAATGAGGCCTTCTTGTCGGAAAAAATTGTTGTACCCACGT
    P  E  F  F  E  A  V  N  E  A  F  L  S  E  K  I  V  V  P  T  S
    CCTCTGTGGTCAGCCTCTGGTTTCGGCATCTCCCCAGTCTTGAAAAAGCAACGCTGCAT
    S  V  V  S  L  W  F  R  H  L  P  S  L  E  K  A  T  L  H  257
```

FIG. 11A

```
1081 CTTTTTGAAAAGCTTTTCTCCAGCAAGATAATTTGCCTGAGAAGGATGGAGTGCTGTATAA
      L  F  E  K  L  F  S  S  K  I  I  C  L  R  R  M  E  C  C  I  R

GAGAGTCATTCCTGCCTCAAGCAGCCTGCCAACCTGCCATCTTCAGAATTGTTCATGAA
      E  S  F  L  P  Q  A  A  C  Q  P  A  I  F  R  I  V  H  E     297

1201 ATGTTCAGGTTTGTGCTGCTGAAAAACTGACGGAGCCCCAGAAGTACTAGCTGCTCTTCAGG
      M  F  R  F  V  L  L  K  T  D  G  A  P  E  V  L  A  A  L  Q  V

TTTTCACATCGTGCTTGGTAGAAGCTCTGAAAAAAGAAAACAAGCAGCTGACGTTTGCC
      F  T  S  C  L  V  E  A  L  K  K  E  N  K  Q  L  T  F  A     337

1321 CTCAGGACCTACTTTCCTTACGGTGCTCCATGTCTTGCTGCAGCGCTGTCCAGCACCCTG
      L  R  T  Y  F  P  Y  G  A  P  C  L  A  A  A  L  S  Q  H  P  E

AAGCAATCCCACAGGGACACCGGCTCCAGCCTCTGCTGCACATTTCCCAACTCCTCAGA
      A  I  P  Q  G  H  R  L  Q  P  L  L  H  I  S  Q  L  L  R     376

1441 GAAGCAGTTGAAGACTGTACTCGTGGGTCTCCGCGAAATCCCTTTGAGAGCTGGTTTTTGT
      E  A  V  E  D  C  T  R  G  S  P  R  N  P  F  E  S  W  F  L  F

TTGTTCACTTTGGAGGATGGGTTGACCTGGCTGTGGCAGAGTTACTGCTGAGGGAGGAA
      V  H  F  G  G  W  V  D  L  A  V  A  E  L  L  L  R  E  E     417

1501 GCTGAGCCTCCTGCTGGCCTGCTGTGGCTCTTGGTGTTCTATTACAGCCCACAGGATGGGA
      A  E  P  P  A  G  L  L  W  L  L  V  F  Y  Y  S  P  Q  D  G  S

GTCAGCAGAGAGAGCAGAGCATGGTGGAGCTGAAGGTATTAATCAACCGTCTCCTGATG
      Q  Q  R  E  Q  S  M  V  E  L  K  V  L  I  N  R  L  L  M     457

1561 CTGCTCAGAAGCGGCCCCCTCTCAGCTACTGATCTGCAGGAAGCAGCTGAGAGTCCCAGTG
      L  L  R  S  G  P  L  S  A  T  D  L  Q  E  A  A  E  S  P  S  G

GAGACCCCAGACCACCTGTATGTGGACAGCTGGTCAGACGCCTTCTTCTTAGTCTCTTG
      D  P  R  P  P  V  C  G  Q  L  V  R  R  L  L  L  S  L  L     496

1801 CTCTGGACCCCAGAAGGCCATGCAATTGTCTGGGAAGCTGTCACCCATATGGCCCACACGG
      L  W  T  P  E  G  H  A  I  V  W  E  A  V  T  H  M  A  H  T  D

ATGCTGTAATCCATGAGATTATTGGTTTTCTTGACCAGACCTTGTACAGATCACAACAT
      A  V  I  H  E  I  I  G  F  L  D  Q  T  L  Y  R  S  Q  H     537

1921 CTTTGTGTTGAAGCCTCGAGAAAACTGGCCAGAGACCTCCTAAAGGAGCTGCAAGCCCAGG
      L  C  V  E  A  S  R  K  L  A  R  D  L  L  K  E  L  Q  A  Q  V

TCTAGCAGGTAGTACAGAATGTGGGCACCTGCGGTGAAGCTCCCTCAGTGGATGAGATG   558
```

FIG. 11B

2041 CTGTTTCTGAGGCAAGAACAAGTGAGAGTGGTTGAACATATTCGTGCCTTGGCCTGATGGA
     GTGATGTGTACCACCTCCCACGCTGTACTGCCTGGCCCCGGCGGTCCATGAGTATTATG
2161 AAGGGAAGGGCCCAGACTGCCTGTTAGGTTCCAGCCATTCATAAGAGCTAGCACTGGCTGG
     TGTGCTGACTCTCTTTATCCTTCCCTCTCTAGTGAAGGTGTGGGGGATGCCCAGTAGCA
2281 GGAGACATGAGCCCTGTAGTGGATGAGGCTGTACCGTACAGATGAGCACCTGNCTCACCGG
     TGACTGTCGCTCAGTGAGGCCTTTGTTCCTCAGTGCAGAAATGCTGCAAGGCACCACTA
2401 TAGTGGAAGGAATGAGAGGTGGCCAGAGAAGGGTCATTCCTTCCTCCTCCTCTAAACCCCC
     AAAAGGCAAAACACATCTGCTTCCCTATGTCT<u>AGTAAA</u>CAGGATTTGGAAACTGAGAGT
2521 GAGTCCTTGTCCTCCTGCACTTGCTGTGGGTGGGGATGACGGGCATGGCTGTTGTTTTCTA
     GTGAGAATATATACAAGTGAGCAGTGTGTGGGCTGTGACCCTCCTGCACATCTGCTATG
2641 AGAACCCTTGCCCCATGTGAAATCAGCTTCAATTCTCACAGTAGGACATTTGATGACTGCA
     CTCAGGCTGTCTAGGGGGGTTGTGGCATAAAGTCATGAAGGCCTGGGTTTTCTCTTGCA
2761 TCTGCACATCCAGGCTTTGCCGGGCAAACACTGACTGGCAGTGGATTCGTCTTTTACCCAC
     CTGCTGATGGGCTCACAGTGGAGTGGAGCTGGACTTTCTACTTTTTCATTCTG<u>AATAAA</u>
2881 AAGTTGTACTTAATTT - poly A tail

FIG. 11C

```
    AATTCCCGCACGCGCAGTGCACTCCCTTGCGGCCGCGGGAAAATTCCAAACACGTCAAAA
    CAAAAAAGGTTCCGTGAGCTGTGCCAAGTTTTCAAGCCGCAGAAGCCGGGCGGTGGCTTC
121 TTTTCCGCCGCAGCCCAGTCTGCTGAGGCAGCTCTGGGTGAGGACCACCCGGGAAGACCG
    CCGTTTCCTGCTAGGGCAGAGAAGACTCGCGAGAACGTGCGCCCGAGTCTCAACGTGGGC
241 GAGCCGCGCTCCCGGGGGGTGGAGCTGAGGCAGGACGGCTGCTGTGAAGGGACAGTGCTG
    CTCTCAGAGATGGCTCAGGAGTCTGCAGACCTTGCTTCTGACTGTCAGTCTTGGCTGCAG
              M  A  Q  E  S  A  D  L  A  S  D  C  Q  S  W  L  Q  16
361 AAGCTTTCTGCATGGGAACAGGCCTCTTCTGAGGAAACCCAGAAGGACACTTGTCTTCAC
     K  L  S  A  W  E  Q  A  S  S  E  E  T  Q  K  D  T  C  L  H
    TTGTCCGGGTTCCAGGAGTTCCTGAGGCAGATGTATGAAATCTTGAAGGAGATGGATTCT
     L  S  G  F  Q  E  F  L  R  Q  M  Y  E  I  L  K  E  M  D  S  57
481 GATGCAATCCTGGAAAGGTTCCCCACAATTGGTCAACTGTTGGCAAAAGCTTGTTGGAATC
     D  A  I  L  E  R  F  P  T  I  G  Q  L  L  A  K  A  C  W  N  P
    CTCTCATCTTAGCATATGATGAAAGCCAAAAAATTGTAATATGGTGCTTATGTTGTCTG
     L  I  L  A  Y  D  E  S  Q  K  I  V  I  W  C  L  C  C  L  97
601 ATGAACAAAGAACCTCGGACTTCTGCAGAGTCAGGACTTAACTCGTGGATCCGGGGTTTGT
     M  N  K  E  P  R  T  S  A  E  S  G  L  N  S  W  I  R  G  L  L
    TATCTCATGTACTTTCTGCATTCAGATTCGACATGAAAGAAGTTTGTCTTTTTACCAAA
     S  H  V  L  S  A  F  R  F  D  M  K  E  V  C  L  F  T  K  136
721 AGTCTTGGATATGAGTCTATTGATTACTATCCTAGTTTGCTTAAAAATATGGTTTTGTCAT
     S  L  G  Y  E  S  I  D  Y  Y  P  S  L  L  K  N  M  V  L  S  L
    TAGTGTCTGAGCTCAGAGAGAGTCATCTTAATGGACTGAGCACTCAAAGTCGGATGGCT
     V  S  E  L  R  E  S  H  L  N  G  L  S  T  Q  S  R  M  A  176
841 CCTGAGCGCATGATGTCCCTGTCAGAAGTTTGTGTCCCTCTTGTCACTCTGCCTGATATGG
     P  E  R  M  M  S  L  S  E  V  C  V  P  L  V  T  L  P  D  M  E
    AACCCCTGGTAGAGGCTCTACTCACCTACCATGGACATGAGCCCCAGGAAGTCCTGGCT
     P  L  V  E  A  L  L  T  Y  H  G  H  E  P  Q  E  V  L  A  217
961 CCTGAGTTCTTCGAAGCTGTAAATGAGGCCTTCTTGTCGGAAAAAATTGTTGTACCCACGT
     P  E  F  F  E  A  V  N  E  A  F  L  S  E  K  I  V  V  P  T  S
    CCTCTGTGGTCAGCCTCTGGTTTCGGCATCTCCCCAGTCTTGAAAAAGCAACGCTGCAT
     S  V  V  S  L  W  F  R  H  L  P  S  L  E  K  A  T  L  H  257
```

FIG. 12A

```
1081 CTTTTTGAAAAGCTTTTCTCCAGCAAGATAATTTGCCTGAGAAGGATGGAGTGCTGTATAA
      L  F  E  K  L  F  S  S  K  I  I  C  L  R  R  M  E  C  C  I  R

GAGAGTCATTCCTGCCTCAAGCAGCCTGCCAACCTGCCATCTTCAGAATTGTTCATGAA
      E  S  F  L  P  Q  A  A  C  Q  P  A  I  F  R  I  V  H  E    297

1201 ATGTTCAGGTTTGTGCTGCTGAAAACTGACGGAGCCCCAGAAGTACTAGCTGCTCTTCAGG
      M  F  R  F  V  L  L  K  T  D  G  A  P  E  V  L  A  A  L  Q  V

TTTTCACATCGTGCTTGGTAGAAGCTCTGAAAAAAGAAAACAAGCAGCTGACGTTTGCC
      F  T  S  C  L  V  E  A  L  K  K  E  N  K  Q  L  T  F  A    337

1321 CTCAGGACCTACTTTCCTTACGGTGCTCCATGTCTTGCTGCAGCGCTGTCCCAGCACCCTG
      L  R  T  Y  F  P  Y  G  A  P  C  L  A  A  A  L  S  Q  H  P  E

AAGCAATCCCACAGGGACACCGGCTCCAGCCTCTGCTGCACATTTCCCAACTCCTCAGA
      A  I  P  Q  G  H  R  L  Q  P  L  L  H  I  S  Q  L  L  R    376

1441 GAAGCAGTTGAAGACTGTACTCGTGGGTCTCCGCGAAATCCCTTTGAGAGCTGGTTTTTGT
      E  A  V  E  D  C  T  R  G  S  P  R  N  P  F  E  S  W  F  L  F

TTGTTCACTTTGGAGGATGGGTTGACCTGGCTGTGGCAGAGTTACTGCTGAGGGAGGAA
      V  H  F  G  G  W  V  D  L  A  V  A  E  L  L  L  R  E  E    417

1501 GCTGAGCCTCCTGCTGGCCTGCTGTGGCTCTTGGTGTTCTATTACAGCCCACAGGATGGGA
      A  E  P  P  A  G  L  L  W  L  L  V  F  Y  Y  S  P  Q  D  G  S

GTCAGCAGAGAGAGCAGAGCATGGTGGAGCTGAAGGTATTAATCAACCGTCTCCTGATG
      Q  Q  R  E  Q  S  M  V  E  L  K  V  L  I  N  R  L  L  M    457

1561 CTGCTCAGAAGCGGCCCCCTCTCAGCTACTGATCTGCAGGAAGCAGCTGAGAGTCCCAGTG
      L  L  R  S  G  P  L  S  A  T  D  L  Q  E  A  A  E  S  P  S  G

GAGACCCCAGACCACCTGTATGTGGACAGCTGGTCAGACGCCTTCTTCTTAGTCTCTTG
      D  P  R  P  P  V  C  G  Q  L  V  R  R  L  L  L  S  L  L    496

1801 CTCTGGACCCCAGAAGGCCATGCAATTGTCTGGGAAGCTGTCACCCATATGGCCCACACGG
      L  W  T  P  E  G  H  A  I  V  W  E  A  V  T  H |M  A  H  T  D
                                                     |
     |GGTCCGACTTTTGAGATCACAGGCCCAGGATGCTGCCCCAGGATATGGAGATCC
     |G
      G  P  T  F  E  I  T  G  P  G  C  C  P  R  I  W  R  S

ATGCTGTAATCCATGAGATTATTGGTTTTCTTGACCAGACCTTGTACAGATCACAACAT
      A  V  I  H  E  I  I  G  F  L  D  Q  T  L  Y  R  S  Q  H    537

|ACAAAGCCACAGCACAGACCCAGAGCCCACCTGTGCTGTACAGA|
      T  K  P  Q  H  R  P  R  A  H  L  C  C  T  E
```

FIG. 12B

1921 CTTTGTGTTGAAGCCTCGAGAAAACTGGCCAGAGACCTCCTAAAGGAGCTGCAAGCCCAGG
     L   C   V   E   A   S   R   K   L   A   R   D   L   L   K   E   L   Q   A   Q   V

TCTAGCAGGTAGTACAGAATGTGGGCACCTGCGGTGAAGCTCCCTCAGTGGATGAGATG
                                                                                    558

2041 CTGTTTCTGAGGCAAGAACAAGTGAGAGTGGTTGAACATATTCGTGCCTTGGCCTGATGGA

GTGATGTGTACCACCTCCCACGCTGTACTGCCTGGCCCCGGCGGTCCATGAGTATTATG

2161 AAGGGAAGGGCCCAGACTGCCTGTTAGGTTCCAGCCATTCATAAGAGCTAGCACTGGCTGG

TGTGCTGACTCTCTTTATCCTTCCCTCTCTAGTGAAGGTGTGGGGGATGCCCAGTAGCA

2281 GGAGACATGAGCCCTGTAGTGGATGAGGCTGTACCGTACAGATGAGCACCTGNCTCACCGG

TGACTGTCGCTCAGTGAGGCCTTTGTTCCTCAGTGCAGAAATGCTGCAAGGCACCACTA

2401 TAGTGGAAGGAATGAGAGGTGGCCAGAGAAGGGTCATTCCTTCCTCCTCCTCTAAACCCCC

AAAAGGCAAAACACATCTGCTTCCCTATGTCT<u>AGTAAA</u>CAGGATTTGGAAACTGAGAGT

2521 GAGTCCTTGTCCTCCTGCACTTGCTGTGGGTGGGGATGACGGGCATGGCTGTTGTTTTCTA

GTGAGAATATATACAAGTGAGCAGTGTGTGGGCTGTGACCCTCCTGCACATCTGCTATG

2641 AGAACCCTTGCCCCATGTGAAATCAGCTTCAATTCTCACAGTAGGACATTTGATGACTGCA

CTCAGGCTGTCTAGGGGGGTTGTGGCATAAAGTCATGAAGGCCTGGGTTTTCTCTTGCA

2761 TCTGCACATCCAGGCTTTGCCGGGCAAACACTGACTGGCAGTGGATTCGTCTTTTACCCAC

CTGCTGATGGGCTCACAGTGGAGTGGAGCTGGACTTTCTACTTTTTCATTCTG<u>AATAAA</u>

2881 AAGTTGTACTTAATTT - poly A tail

FIG. 12C

```
EXON-1  ACTGCTGACA CGTGTGCGCG CGCGCGGCTC CACTGCCGGG CGACCGCGGG  50
                 ||  ||||| ||    |||| ||    ||  ||||||||
MOUSE                     GCA CGCGCAG-TG CACTCCCTTG CGGCCGCGGG  32

EXON-1  AAAATTCCAA AAAAACTCAA AA-AGCCAA- -TAC-GAG-G CAAAGCCAAA  95
        ||||||||||  | |   ||||  ||  |   ||   | | | | ||||||||||
MOUSE   AAAATTCCAA ACAC-GTCAA AACAAAAAAG GTTCCGTGAG CTGTGCCAAG  81

EXON-1  TTTTCAAGCC ACAGATCCCG GCGGTGGCT TCCTTTCCGC CACTGCCCAA  145
        ||||||||||  ||||  |||  |||||||||| || ||||||| | | |||||
MOUSE   TTTTCAAGCC GCAGAAGCCG GGCGGTGGCT TCTTTTCCGC CGCAGCCCAG  131

EXON-1  ACTGCTGAAG CAGCTCC-CG CGAGGACCAC CCGATTTAAT GTGTGCCGAC  194
        |||||||  | ||||||   |  |||||||||   |||   |||   |||  |
MOUSE   TCTGCTGAGG CAGCTCTGGG TGAGGACCAC CCGGG--AA- GA---CCG-C  174

EXON-1  CATTTCCTTC -AGTGCT--- ---------- ---------- ----------  210
         | ||||||| |  || ||
MOUSE   CGTTTCCTGC TAGGGCAGAG AAGACTCGCG AGAACGTGCG CCCGAGTCTC  224

EXON-1  ---------- ---------- ---------- ---------- -GGACAGGCT  219
                                                     |||| ||||
MOUSE   AACGTGGGCG AGCCGCGCTC CCGGGGGGTG GAGCTGAGGC AGGAC-GGCT  273

EXON-1  GCTGTGAAGG GACA-T-CAC CTTTTCGCTT TTTCCAAGATG             258
        ||||||||||  ||||  |            |  ||  ||Met
MOUSE   GCTGTGAAGG GACAGTGC---------TGC TCTCAGAGATG             305
```

FIG. 13

```
human   MAQDSVDLSC DYQFWMQKLS VWDQASTLET QQDTCLHVAQ FQEFLRKMYE 50
        |||:|:||:  | | |:|||| :|:|||: || | |||||:  |||||| |||
mouse   MAQESADLAS DCQSWLQKLS AWEQASSEET QKDTCLHLSG FQEFLRQMYE 50 human   ALKEMDSNTV IERFPTIGQL LAKACWNPFI LAYDESQKIL IWCLCCLINK 100
        ||||||  :  :|||||||||| ||||||||| | |||||||||: ||||||||:||
mouse   ILKEMDSDAI LERFPTIGQL LAKACWNPLI LAYDESQKIV IWCLCCLMNK 100 human   EPQNSGQSKL NSWIQGVLSH ILSALRFD-K EVALFTQGLGY APIDYYPGL 149
        ||  |: | | |||| |:||| :||| |||  || ||| ||| ||||| |
mouse   EPRTSAESGL NSWIRGLLSH VLSAFRFDMK EVELFTKSLGY ESIDYYPSL 150 human   LKNMVLSLAS ELRENHLNGF NTQRRMAPER VASLSRVCVP LITLTDVDPL 199
        ||||||||:|  |||| ||||  || ||||||  : ||| |||| |:|| |::||
mouse   LKNMVLSLVS ELRESHLNGL STQSRMAPER MMSLSEVCVP LVTLPDMEPL 200 human   VEALLICHGR EPQEILQPEF FEAVNEAILL KKISLPMSAV VCLCVRHLPS 249
        ||||| ||:  ||||:| ||| ||||||| |  || :| |  |:|  ||||
mouse   VEALLTYHGH EPQEVLAPEF FEAVNEAFLS EKIVVPTSSV VSLWFRHLPS 250 human   LEKAMLHLFE KLISSERNCL RRIECFIKDS SLPQAACHPA IFRVVDEMFR 299
        ||||  ||||| || ||   || ||:|| |:::|   |||||| || ||||:|  ||||
mouse   LEKATLHLFE KLFSSKIICL RRMECCIRES FLPQAACQPA IFRIVHEMFR 300 human   CALLETDGAL EIIATIQVFT QCFVEALEKA SKQLRFALKT YFPYTSPSLA 349
        :||  ||||  |:::|  :|||| | |||| | |||  |||:| ||||: |:||
mouse   FVLLKTDGAP EVLAALQVFT SCLVEALKKE NKQLTFALRT YFPYGAPCLA 350 human   MVLLQDPQDI PRGHWLQTLK HISELLREAV EDQTHGSCGG PFESWFLFIH 399
        :| | |  |  | ||| || |  |||  ||||||  || |:||   ||||||||:|
mouse   AALSQHPEAI PQGHRLQPLL HISQLLREAV EDCTRGSPRN PFESWFLFVH 400 human   FGGWAEM-VA EQLLMSAAEP PTALLWLLAF YYGPRDGRQQ RAQTMVQVKA 448
        ||||:::  ||  | ||   ||| | :||||| :| || || ||  | |:|| :|:
mouse   FGGWVDLAVA ELLLREEAEP PAGLLWLLVF YYSPQDGSQQ REQSMVELKV 450 human   VLGHLLAMSR SSSLSAQDLQ TVAGQGTDTD LRAPAQQLIR HLLLNFLLWA 498
        :: :|| : |  |: ||| |||  :|  :            ||:| :||| ||||
mouse   LINRLLMLLR SGPLSATDLQ EAAESPSGDP RPPVCGQLVR RLLLSLLLWT 500 human   PGGHTIAWDV ITLMAHTAEI THEIIGFLDQ TLYRWNRLGI ESPRSEKLAR 548
        | || |:|::  :| ||||  :| ||||||||| ||||  :::  :  |  |   ||||
mouse   PEGHAIVWEA VTHMAHTDAV IHEIIGFLDQ TLYRSQHLCV EASR--KLAR 548 human   ELLKELRTQV 558
        :|||||  ||
mouse   DLLKELQAQV 558
```

FIG. 14

SEQUENCE LISTING ( 1 ) GENERAL INFORMATION:

( i i i ) NUMBER OF SEQUENCES: 73

( 2 ) INFORMATION FOR SEQ ID NO: 1:

( i ) SEQUENCE CHARACTERISTICS:
        ( A ) LENGTH: 4488 base pairs
        ( B ) TYPE: Nucleic Acid
        ( C ) STRANDEDNESS: Double stranded
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
    ( A ) ORGANISM: Homo sapiens ( v i i ) IMMEDIATE SOURCE:
    ( A ) LIBRARY: Human cDNA ( v i i i ) POSITION IN GENOME: (of corresponding genomic gene)
    ( A ) CHROMOSOME/SEGMENT: 9q
    ( B ) MAP POSITION: 22.3
    ( C ) UNITS:

( x ) SEQUENCE DESCRIPTION: SEQ ID NO: 1:

```
                                                      GAGCCCCC GGAGAGGCGG      18

GAGCGGTGTT GGCGTTTTGG TTCTTTTTGT TCATTGAGCG CAGGCAGCTA TGTCTTCTTC      78

AAAGGAGAGG AGCAAAGCTT TAATGTGTGC CGACCATTTC CTTCAGTGCT GGACAGGCTG     138

CTGTGAAGGG ACATCACCTT TTCGCTTTTT CCAAG ATG GCT CAA GAT TCA            188
                                        Met Ala Gln Asp Ser
                                         1               5

GTA GAT CTT TCT TGT GAT TAT CAG TTT TGG ATG CAG AAG CTT TCT           233
Val Asp Leu Ser Cys Asp Tyr Gln Phe Trp Met Gln Lys Leu Ser
              10                  15                  20

GTA TGG GAT CAG GCT TCC ACT TTG GAA ACC CAG CAA GAC ACC TGT           278
Val Trp Asp Gln Ala Ser Thr Leu Glu Thr Gln Gln Asp Thr Cys
              25                  30                  35

CTT CAC GTG GCT CAG TTC CAG GAG TTC CTA AGG AAG ATG TAT GAA           323
Leu His Val Ala Gln Phe Gln Glu Phe Leu Arg Lys Met Tyr Glu
              40                  45                  50

GCC TTG AAA GAG ATG GAT TCT AAT ACA GTC ATT GAA AGA TTC CCC           368
Ala Leu Lys Glu Met Asp Ser Asn Thr Val Ile Glu Arg Phe Pro
              55                  60                  65

ACA ATT GGT CAA CTG TTG GCA AAA GCT TGT TGG AAT CCT TTT ATT           413
Thr Ile Gly Gln Leu Leu Ala Lys Ala Cys Trp Asn Pro Phe Ile
              70                  75                  80

TTA GCA TAT GAT GAA AGC CAA AAA ATT CTA ATA TGG TGC TTA TGT           458
Leu Ala Tyr Asp Glu Ser Gln Lys Ile Leu Ile Trp Cys Leu Cys
              85                  90                  95

TGT CTA ATT AAC AAA GAA CCA CAG AAT TCT GGA CAA TCA AAA CTT           503
Cys Leu Ile Asn Lys Glu Pro Gln Asn Ser Gly Gln Ser Lys Leu
             100                 105                 110

AAC TCC TGG ATA CAG GGT GTA TTA TCT CAT ATA CTT TCA GCA CTC           548
Asn Ser Trp Ile Gln Gly Val Leu Ser His Ile Leu Ser Ala Leu
             115                 120                 125

AGA TTT GAT AAA GAA GTT GCT CTT TTC ACT CAA GGT CTT GGG TAT           593
Arg Phe Asp Lys Glu Val Ala Leu Phe Thr Gln Gly Leu Gly Tyr
             130                 135                 140

GCA CCT ATA GAT TAC TAT CCT GGT TTG CTT AAA AAT ATG GTT TTA           638
Ala Pro Ile Asp Tyr Tyr Pro Gly Leu Leu Lys Asn Met Val Leu
             145                 150                 155

TCA TTA GCG TCT GAA CTC AGA GAG AAT CAT CTT AAT GGA TTT AAC           683
Ser Leu Ala Ser Glu Leu Arg Glu Asn His Leu Asn Gly Phe Asn
             160                 165                 170

ACT CAA AGG CGA ATG GCT CCC GAG CGA GTG GCG TCC CTG TCA CGA           728
Thr Gln Arg Arg Met Ala Pro Glu Arg Val Ala Ser Leu Ser Arg
             175                 180                 185

GTT TGT GTC CCA CTT ATT ACC CTG ACA GAT GTT GAC CCC CTG GTG           773
Val Cys Val Pro Leu Ile Thr Leu Thr Asp Val Asp Pro Leu Val
             190                 195                 200

GAG GCT CTC CTC ATC TGT CAT GGA CGT GAA CCT CAG GAA ATC CTC           818
Glu Ala Leu Leu Ile Cys His Gly Arg Glu Pro Gln Glu Ile Leu
             205                 210                 215
```

-continued

| | | | | | | | | | | | | | | | |
|---|---|---|---|---|---|---|---|---|---|---|---|---|---|---|---|
| CAG | CCA | GAG | TTC | TTT | GAG | GCT | GTA | AAC | GAG | GCC | ATT | TTG | CTG | AAG | 863 |
| Gln | Pro | Glu | Phe 220 | Phe | Glu | Ala | Val | Asn 225 | Glu | Ala | Ile | Leu | Leu 230 | Lys | |
| AAG | ATT | TCT | CTC | CCC | ATG | TCA | GCT | GTA | GTC | TGC | CTC | TGG | CTT | CGG | 908 |
| Lys | Ile | Ser | Leu | Pro 235 | Met | Ser | Ala | Val | Val 240 | Cys | Leu | Trp | Leu | Arg 245 | |
| CAC | CTT | CCC | AGC | CTT | GAA | AAA | GCA | ATG | CTG | CAT | CTT | TTT | GAA | AAG | 953 |
| His | Leu | Pro | Ser | Leu 250 | Glu | Lys | Ala | Met | Leu 255 | His | Leu | Phe | Glu | Lys 260 | |
| CTA | ATC | TCC | AGT | GAG | AGA | AAT | TGT | CTG | AGA | AGG | ATC | GAA | TGC | TTT | 998 |
| Leu | Ile | Ser | Ser | Glu 265 | Arg | Asn | Cys | Leu | Arg 270 | Arg | Ile | Glu | Cys | Phe 275 | |
| ATA | AAA | GAT | TCA | TCG | CTG | CCT | CAA | GCA | GCC | TGC | CAC | CCT | GCC | ATA | 1043 |
| Ile | Lys | Asp | Ser | Ser 280 | Leu | Pro | Gln | Ala | Ala 285 | Cys | His | Pro | Ala | Ile 290 | |
| TTC | CGG | GTT | GTT | GAT | GAG | ATG | TTC | AGG | TGT | GCA | CTC | CTG | GAA | ACC | 1088 |
| Phe | Arg | Val | Val | Asp 295 | Glu | Met | Phe | Arg | Cys 300 | Ala | Leu | Leu | Glu | Thr 305 | |
| GAT | GGG | GCC | CTG | GAA | ATC | ATA | GCC | ACT | ATT | CAG | GTG | TTT | ACG | CAG | 1133 |
| Asp | Gly | Ala | Leu | Glu 310 | Ile | Ile | Ala | Thr | Ile 315 | Gln | Val | Phe | Thr | Gln 320 | |
| TGC | TTT | GTA | GAA | GCT | CTG | GAG | AAA | GCA | AGC | AAG | CAG | CTG | CGG | TTT | 1178 |
| Cys | Phe | Val | Glu | Ala 325 | Leu | Glu | Lys | Ala | Ser 330 | Lys | Gln | Leu | Arg | Phe 335 | |
| GCA | CTC | AAG | ACC | TAC | TTT | CCT | TAC | ACT | TCT | CCA | TCT | CTT | GCC | ATG | 1223 |
| Ala | Leu | Lys | Thr | Tyr 340 | Phe | Pro | Tyr | Thr | Ser 345 | Pro | Ser | Leu | Ala | Met 350 | |
| GTG | CTG | CTG | CAA | GAC | CCT | CAA | GAT | ATC | CCT | CGG | GGA | CAC | TGG | CTC | 1268 |
| Val | Leu | Leu | Gln | Asp 355 | Pro | Gln | Asp | Ile | Pro 360 | Arg | Gly | His | Trp | Leu 365 | |
| CAG | ACA | CTG | AAG | CAT | ATT | TCT | GAA | CTG | CTC | AGA | GAA | GCA | GTT | GAA | 1313 |
| Gln | Thr | Leu | Lys | His 370 | Ile | Ser | Glu | Leu | Leu 375 | Arg | Glu | Ala | Val | Glu 380 | |
| GAC | CAG | ACT | CAT | GGG | TCC | TGC | GGA | GGT | CCC | TTT | GAG | AGC | TGG | TTC | 1358 |
| Asp | Gln | Thr | His | Gly 385 | Ser | Cys | Gly | Gly | Pro 390 | Phe | Glu | Ser | Trp | Phe 395 | |
| CTG | TTC | ATT | CAC | TTC | GGA | GGA | TGG | GCT | GAG | ATG | GTG | GCA | GAG | CAA | 1403 |
| Leu | Phe | Ile | His | Phe 400 | Gly | Gly | Trp | Ala | Glu 405 | Met | Val | Ala | Glu | Gln 410 | |
| TTA | CTG | ATG | TCG | GCA | GCC | GAA | CCC | CCC | ACG | GCC | CTG | CTG | TGG | CTC | 1448 |
| Leu | Leu | Met | Ser | Ala 415 | Ala | Glu | Pro | Pro | Thr 420 | Ala | Leu | Leu | Trp | Leu 425 | |
| TTG | GCC | TTC | TAC | TAC | GGC | CCC | CGT | GAT | GGG | AGG | CAG | CAG | AGA | GCA | 1493 |
| Leu | Ala | Phe | Tyr | Tyr 430 | Gly | Pro | Arg | Asp | Gly 435 | Arg | Gln | Gln | Arg | Ala 440 | |
| CAG | ACT | ATG | GTC | CAG | GTG | AAG | GCC | GTG | CTG | GGC | CAC | CTC | CTG | GCA | 1538 |
| Gln | Thr | Met | Val | Gln 445 | Val | Lys | Ala | Val | Leu 450 | Gly | His | Leu | Leu | Ala 455 | |
| ATG | TCC | AGA | AGC | AGC | AGC | CTC | TCA | GCC | CAG | GAC | CTG | CAG | ACG | GTA | 1583 |
| Met | Ser | Arg | Ser | Ser 460 | Ser | Leu | Ser | Ala | Gln 465 | Asp | Leu | Gln | Thr | Val 470 | |
| GCA | GGA | CAG | GGC | ACA | GAC | ACA | GAC | CTC | AGA | GCT | CCT | GCA | CAA | CAG | 1628 |
| Ala | Gly | Gln | Gly | Thr 475 | Asp | Thr | Asp | Leu | Arg 480 | Ala | Pro | Ala | Gln | Gln 485 | |
| CTG | ATC | AGG | CAC | CTT | CTC | CTC | AAC | TTC | CTG | CTC | TGG | GCT | CCT | GGA | 1673 |
| Leu | Ile | Arg | His | Leu 490 | Leu | Leu | Asn | Phe | Leu 495 | Leu | Trp | Ala | Pro | Gly 500 | |
| GGC | CAC | ACG | ATC | GCC | TGG | GAT | GTC | ATC | ACC | CTG | ATG | GCT | CAC | ACT | 1718 |
| Gly | His | Thr | Ile | Ala 505 | Trp | Asp | Val | Ile | Thr 510 | Leu | Met | Ala | His | Thr 515 | |

-continued

| | | | | | | | | | | | | | | |
|---|---|---|---|---|---|---|---|---|---|---|---|---|---|---|
| GCT | GAG | ATA | ACT | CAC | GAG | ATC | ATT | GGC | TTT | CTT | GAC | CAG | ACC | TTG |
| Ala | Glu | Ile | Thr | His | Glu | Ile | Ile | Gly | Phe | Leu | Asp | Gln | Thr | Leu |
| | | | 520 | | | | | 525 | | | | | 530 | |

1763

| TAC | AGA | TGG | AAT | CGT | CTT | GGC | ATT | GAA | AGC | CCT | AGA | TCA | GAA | AAA |
|---|---|---|---|---|---|---|---|---|---|---|---|---|---|---|
| Tyr | Arg | Trp | Asn | Arg | Leu | Gly | Ile | Glu | Ser | Pro | Arg | Ser | Glu | Lys |
| | | | 535 | | | | | 540 | | | | | 545 | |

1808

| CTG | GCC | CGA | GAG | CTC | CTT | AAA | GAG | CTG | CGA | ACT | CAA | GTC | TAG | A |
|---|---|---|---|---|---|---|---|---|---|---|---|---|---|---|
| Leu | Ala | Arg | Glu | Leu | Leu | Lys | Glu | Leu | Arg | Thr | Gln | Val | | |
| | | | 550 | | | | | 555 | | | | | | |

1851

```
AGGCACGCAG GCCGTGTGGG TGCCCGGCGT GAGGGATCAG GCTCGCCAGG                    1901
GCCACAGGAC AGGTGATGAC CTGTGGCCAC GCATTTGTGG AGTAAGTGCC CTCGCTGGGC        1961
TGTGAGAATG AGCTGTACAC ATCTTGGGAC AATCTGCTAG TATCTATTTT ACAAAATGCA        2021
GAGCCAGGTC CCTCAGCCCA GACTCAGTCA GACATGTTCA CTAATGACTC AAGTGAGCTT        2081
CGGTACTCCT GGTGCCCGCC CGGCCAGACC GTCAGCTTGA TAATTACTAA AGCAAAGGCC        2141
TGGGTGGGAG AACAGGTTTC TAGTTTTTAC CCAAGTCAAG CTGCACATCT ATTATTTAAA        2201
AATTCAAAGT CTTAGAACCA AGAATTTGGT CATGAACCAT TAAAGAATTT AGAGAGAACT        2261
TAGCTCTTTT TAGACTCTTT TTAGGAGTCA GGGATCTGGG ATAAAGCCAC ACTGTCTTGC        2321
TGTATGGAGA AATTCTTCAA GGGGAGTCAG GGTCCCTCAG GCTTCCCTTG TGTCTCCCTG        2381
GACCTGCCTG ACAGGCCACA GGAGCAGACA GCACACCCAA GCCCGGGCCT CCGGCACACT        2441
CTTTCCACTC TGTATTTGCT AAATGATGCT AACTGCTACC AAAAGGCCCT TGGGACATCA        2501
GAGGAGCCGG CAGCGAAGGT AGAGGATGTG TTCCAGAAAC ATTAGAAGGC AGGATTAATT        2561
CAGTTAGTTA GTCTCTTGTT AAATGGAAAT GGGAATTGGA AATTCCTGAT AAAGAATTGG        2621
CCTGGCTGGG TGCAGTGGCT CACACCTGTG ATCCCAGCAC TTTGGGAGGC CAAGGCAGGG        2681
GGATTACTTC AGCCCAGGAG TTCCAGACTG CCTGGCTAAC ATGGCAATAC CCTATCTCTA        2741
CTAAAAATAC AAAAATTATC GGGGTGCAAT GGCATGCATC TGTAACCCAG CTATTCAAGA        2801
GGCTGAGGCA TGAGGATCTC TTGAACCCGG GAGGTGGGAG TTGTAGTGAG CCGAGATCAT        2861
GACACTGCAC TCCAGCCTGG GCAACAGAGC GAGACCATCT CTTAAAAAAA GGCATTGTTA        2921
GTGTAACTCA AGGTTAACAT TTATTTCATG TCAGTACAGG GTGCTTTTC CTTTCAGGA         2981
CATTCTGGAA TTGTATTGGT TGTACATTCT TTTGTGTCTA TTCTGTTTGT CAAGTGAGTC        3041
AAGACTTGCT TTTGTCCATT TTGATTTGTG TGTATTAGTC TGAGTCTTGG CTCCGTTTTG        3101
AGGTATGAGC AAAGTTTTGC TGGATAGAGT TAACCTTTAG GGAAATTCCT TATTTTGGTA        3161
TGTGGCAATG CTAATAGATC CACTGAAGAT CTGGAAAATT CCAGGAACTT TTTCACCTGA        3221
GCCTTTCTTC TGAGAAATGC TGCAGTCAGA AGGGTGTGCT GGTAAAGTAT TTTGGTGGCA        3281
GCTGCCATCA TGGTCATTGC CTTCATATAA CATGCTTCGT GCTCATGGTC ATTGCCTTCA        3341
TATAACATGC TTCGTGCCAT CATGATCCTT GCCTTCATAT AACAAACATG CTTCGTCAGA        3401
GGTGTTGGGG TTGAAAAAGG AGCTGCATGC TTCACTGGAG TTGAGGGCCT CTCCTGTCTG        3461
ACTTTAAGCC AGAACTTGTG GCTGGGCCAT GGAAGCTGTG ACTCCTCTGT GGACATGGTG        3521
GCAGCAGGGA ACCCCTAGAG AGAGGGGCCA CTGGGACCAG GCCTCCTGTT GTGGAGGGAC        3581
TCCTGGGACA GTCCTCCACC CTGTCCTGTG GTCCTGTGTA CAGGGTTGGC CTCTTCCTCC        3641
TCCCCTGCCA GGCCTCTGCC CATGCCCCTT CCTTCCTTCT CCTGGGACTG GTGAAGCTAG        3701
GCATCTGGAA GACTTCTTCC TAGCCTGGAA GCCCTGACCT CGGCCCATCT GCAGAATCTC        3761
CCAGTTCCTT CACAGCTGCC GAGTCCTCTC ACGGGTGCGG TGGAGGCGGC CTTGCGGTGG        3821
TGCTTTCTGG GCAGCCAGGG GTTCCTGGGT GGGAGGACTG TCCCTCTGGG GACGTGGCAC        3881
```

| | | | | | |
|---|---|---|---|---|---|
| TGAAGTGCCT | GCTGGCTTCA | TGTGGCCCTT | TGCCCTTTCC | CAGCCTGAGA | GATGCTCAAA | 3941 |
| GGTGGGGAGC | TGGGGAGCC | ACCCCTCGGC | CATTCCCTCC | ACCTCCAAGA | CAGGTGGCGG | 4001 |
| CCGGGCAGGC | ACTCTTAAGC | CCACCTCCCC | CTCTTGTTGC | CTTCGATTTC | GGCAAAGCCT | 4061 |
| GGGCAGGTGC | CACCGGGAAG | GAATGGCATC | GAGATGCTGG | GCGGGACGC | GGCGTGGCGA | 4121 |
| GGGGCTTGA | CGGCGTTGGC | GGGGCTGGGC | ACAGGGGCAG | CCGCAGGGAG | GCAGGGATGG | 4181 |
| CAAGGCGTGA | AGCCACCCTG | GAAGGAACTG | GACCAAGGTC | TTCAGAGGTG | CGACAGGGTC | 4241 |
| TGGAATCTGA | CCTTACTCTA | GCAGGAGTTT | TTGTAGACTC | TCCCTGATAG | TTTAGTTTTT | 4301 |
| GATAAAGCAT | GCTGGTAAAA | CCACTACCCT | CAGAGAGAGC | CAAAAATACA | GAAGAGGCGG | 4361 |
| AGAGCGCCCC | TCCAACCAGG | CTGTTATTCC | CCTGGACTCC | GTGACATCTG | TGGAATTTT | 4421 |
| TAGCTCTTTA | AAATCTGTAA | TTTGTTGTCT | ATTTTTCAT | TCTAAATAAA | ACTTCAGTTT | 4481 |
| GCACCTA | | | | | | 4488 |

( 2 ) INFORMATION FOR SEQ ID NO: 2:

( i ) SEQUENCE CHARACTERISTICS:
        ( A ) LENGTH: 2341 base pairs
        ( B ) TYPE: Nucleic Acid
        ( C ) STRANDEDNESS: Double stranded
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Homo sapiens ( v i i ) IMMEDIATE SOURCE:
        ( A ) LIBRARY: Human cDNA ( v i i i ) POSITION IN GENOME: (of corresponding genomic gene)
        ( A ) CHROMOSOME/SEGMENT: 9q
        ( B ) MAP POSITION: 22.3
        ( C ) UNITS:

( x ) SEQUENCE DESCRIPTION: SEQ ID NO: 2:

```
                              ACTGCTGACA CGTGTGCGCG CGCGCGGCTC CACTGCCGGG        40
CGACCGCGGG AAAATTCCAA AAAAACTCAA AAAGCCAATA CGAGGCAAAG CCAAATTTTC               100
AAGCCACAGA TCCCGGGCGG TGGCTTCCTT TCCGCCACTG CCCAAACTGC TGAAGCAGCT               160
CCCGCGAGGA CCACCCGATT TAATGTGTGC CGACCATTTC CTTCAGTGCT GGACAGGCTG               220
CTGTGAAGGG ACATCACCTT TTCGCTTTTT CCAAG ATG GCT CAA GAT TCA                       270
                                        Met Ala Gln Asp Ser
                                         1               5

GTA GAT CTT TCT TGT GAT TAT CAG TTT TGG ATG CAG AAG CTT TCT                     315
Val Asp Leu Ser Cys Asp Tyr Gln Phe Trp Met Gln Lys Leu Ser
             10                  15                  20

GTA TGG GAT CAG GCT TCC ACT TTG GAA ACC CAG CAA GAC ACC TGT                     360
Val Trp Asp Gln Ala Ser Thr Leu Glu Thr Gln Gln Asp Thr Cys
             25                  30                  35

CTT CAC GTG GCT CAG TTC CAG GAG TTC CTA AGG AAG ATG TAT GAA                     405
Leu His Val Ala Gln Phe Gln Glu Phe Leu Arg Lys Met Tyr Glu
             40                  45                  50

GCC TTG AAA GAG ATG GAT TCT AAT ACA GTC ATT GAA AGA TTC CCC                     450
Ala Leu Lys Glu Met Asp Ser Asn Thr Val Ile Glu Arg Phe Pro
             55                  60                  65

ACA ATT GGT CAA CTG TTG GCA AAA GCT TGT TGG AAT CCT TTT ATT                     495
```

|  |  |  |  |  |  |  |  |  |  |  |  |  |  |  |
|---|---|---|---|---|---|---|---|---|---|---|---|---|---|---|
| Thr | Ile | Gly | Gln | Leu | Leu | Ala | Lys | Ala | Cys | Trp | Asn | Pro | Phe | Ile |
|  |  |  | 70 |  |  |  | 75 |  |  |  |  |  | 80 |  |

| TTA | GCA | TAT | GAT | GAA | AGC | CAA | AAA | ATT | CTA | ATA | TGG | TGC | TTA | TGT | 540 |
|---|---|---|---|---|---|---|---|---|---|---|---|---|---|---|---|
| Leu | Ala | Tyr | Asp | Glu | Ser | Gln | Lys | Ile | Leu | Ile | Trp | Cys | Leu | Cys |  |
|  |  |  |  | 85 |  |  |  |  | 90 |  |  |  |  | 95 |  |

| TGT | CTA | ATT | AAC | AAA | GAA | CCA | CAG | AAT | TCT | GGA | CAA | TCA | AAA | CTT | 585 |
|---|---|---|---|---|---|---|---|---|---|---|---|---|---|---|---|
| Cys | Leu | Ile | Asn | Lys | Glu | Pro | Gln | Asn | Ser | Gly | Gln | Ser | Lys | Leu |  |
|  |  |  |  | 100 |  |  |  |  | 105 |  |  |  |  | 110 |  |

| AAC | TCC | TGG | ATA | CAG | GGT | GTA | TTA | TCT | CAT | ATA | CTT | TCA | GCA | CTC | 630 |
|---|---|---|---|---|---|---|---|---|---|---|---|---|---|---|---|
| Asn | Ser | Trp | Ile | Gln | Gly | Val | Leu | Ser | His | Ile | Leu | Ser | Ala | Leu |  |
|  |  |  |  | 115 |  |  |  |  | 120 |  |  |  |  | 125 |  |

| AGA | TTT | GAT | AAA | GAA | GTT | GCT | CTT | TTC | ACT | CAA | GGT | CTT | GGG | TAT | 675 |
|---|---|---|---|---|---|---|---|---|---|---|---|---|---|---|---|
| Arg | Phe | Asp | Lys | Glu | Val | Ala | Leu | Phe | Thr | Gln | Gly | Leu | Gly | Tyr |  |
|  |  |  |  | 130 |  |  |  |  | 135 |  |  |  |  | 140 |  |

| GCA | CCT | ATA | GAT | TAC | TAT | CCT | GGT | TTG | CTT | AAA | AAT | ATG | GTT | TTA | 720 |
|---|---|---|---|---|---|---|---|---|---|---|---|---|---|---|---|
| Ala | Pro | Ile | Asp | Tyr | Tyr | Pro | Gly | Leu | Leu | Lys | Asn | Met | Val | Leu |  |
|  |  |  |  | 145 |  |  |  |  | 150 |  |  |  |  | 155 |  |

| TCA | TTA | GCG | TCT | GAA | CTC | AGA | GAG | AAT | CAT | CTT | AAT | GGA | TTT | AAC | 765 |
|---|---|---|---|---|---|---|---|---|---|---|---|---|---|---|---|
| Ser | Leu | Ala | Ser | Glu | Leu | Arg | Glu | Asn | His | Leu | Asn | Gly | Phe | Asn |  |
|  |  |  |  | 160 |  |  |  |  | 165 |  |  |  |  | 170 |  |

| ACT | CAA | AGG | CGA | ATG | GCT | CCC | GAG | CGA | GTG | GCG | TCC | CTG | TCA | CGA | 810 |
|---|---|---|---|---|---|---|---|---|---|---|---|---|---|---|---|
| Thr | Gln | Arg | Arg | Met | Ala | Pro | Glu | Arg | Val | Ala | Ser | Leu | Ser | Arg |  |
|  |  |  |  | 175 |  |  |  |  | 180 |  |  |  |  | 185 |  |

| GTT | TGT | GTC | CCA | CTT | ATT | ACC | CTG | ACA | GAT | GTT | GAC | CCC | CTG | GTG | 855 |
|---|---|---|---|---|---|---|---|---|---|---|---|---|---|---|---|
| Val | Cys | Val | Pro | Leu | Ile | Thr | Leu | Thr | Asp | Val | Asp | Pro | Leu | Val |  |
|  |  |  |  | 190 |  |  |  |  | 195 |  |  |  |  | 200 |  |

| GAG | GCT | CTC | CTC | ATC | TGT | CAT | GGA | CGT | GAA | CCT | CAG | GAA | ATC | CTC | 900 |
|---|---|---|---|---|---|---|---|---|---|---|---|---|---|---|---|
| Glu | Ala | Leu | Leu | Ile | Cys | His | Gly | Arg | Glu | Pro | Gln | Glu | Ile | Leu |  |
|  |  |  |  | 205 |  |  |  |  | 210 |  |  |  |  | 215 |  |

| CAG | CCA | GAG | TTC | TTT | GAG | GCT | GTA | AAC | GAG | GCC | ATT | TTG | CTG | AAG | 945 |
|---|---|---|---|---|---|---|---|---|---|---|---|---|---|---|---|
| Gln | Pro | Glu | Phe | Phe | Glu | Ala | Val | Asn | Glu | Ala | Ile | Leu | Leu | Lys |  |
|  |  |  |  | 220 |  |  |  |  | 225 |  |  |  |  | 230 |  |

| AAG | ATT | TCT | CTC | CCC | ATG | TCA | GCT | GTA | GTC | TGC | CTC | TGG | CTT | CGG | 990 |
|---|---|---|---|---|---|---|---|---|---|---|---|---|---|---|---|
| Lys | Ile | Ser | Leu | Pro | Met | Ser | Ala | Val | Val | Cys | Leu | Trp | Leu | Arg |  |
|  |  |  |  | 235 |  |  |  |  | 240 |  |  |  |  | 245 |  |

| CAC | CTT | CCC | AGC | CTT | GAA | AAA | GCA | ATG | CTG | CAT | CTT | TTT | GAA | AAG | 1035 |
|---|---|---|---|---|---|---|---|---|---|---|---|---|---|---|---|
| His | Leu | Pro | Ser | Leu | Glu | Lys | Ala | Met | Leu | His | Leu | Phe | Glu | Lys |  |
|  |  |  |  | 250 |  |  |  |  | 255 |  |  |  |  | 260 |  |

| CTA | ATC | TCC | AGT | GAG | AGA | AAT | TGT | CTG | AGA | AGG | ATC | GAA | TGC | TTT | 1080 |
|---|---|---|---|---|---|---|---|---|---|---|---|---|---|---|---|
| Leu | Ile | Ser | Ser | Glu | Arg | Asn | Cys | Leu | Arg | Arg | Ile | Glu | Cys | Phe |  |
|  |  |  |  | 265 |  |  |  |  | 270 |  |  |  |  | 275 |  |

| ATA | AAA | GAT | TCA | TCG | CTG | CCT | CAA | GCA | GCC | TGC | CAC | CCT | GCC | ATA | 1125 |
|---|---|---|---|---|---|---|---|---|---|---|---|---|---|---|---|
| Ile | Lys | Asp | Ser | Ser | Leu | Pro | Gln | Ala | Ala | Cys | His | Pro | Ala | Ile |  |
|  |  |  |  | 280 |  |  |  |  | 285 |  |  |  |  | 290 |  |

| TTC | CGG | GTT | GTT | GAT | GAG | ATG | TTC | AGG | TGT | GCA | CTC | CTG | GAA | ACC | 1170 |
|---|---|---|---|---|---|---|---|---|---|---|---|---|---|---|---|
| Phe | Arg | Val | Val | Asp | Glu | Met | Phe | Arg | Cys | Ala | Leu | Leu | Glu | Thr |  |
|  |  |  |  | 295 |  |  |  |  | 300 |  |  |  |  | 305 |  |

| GAT | GGG | GCC | CTG | GAA | ATC | ATA | GCC | ACT | ATT | CAG | GTG | TTT | ACG | CAG | 1215 |
|---|---|---|---|---|---|---|---|---|---|---|---|---|---|---|---|
| Asp | Gly | Ala | Leu | Glu | Ile | Ile | Ala | Thr | Ile | Gln | Val | Phe | Thr | Gln |  |
|  |  |  |  | 310 |  |  |  |  | 315 |  |  |  |  | 320 |  |

| TGC | TTT | GTA | GAA | GCT | CTG | GAG | AAA | GCA | AGC | AAG | CAG | CTG | CGG | TTT | 1260 |
|---|---|---|---|---|---|---|---|---|---|---|---|---|---|---|---|
| Cys | Phe | Val | Glu | Ala | Leu | Glu | Lys | Ala | Ser | Lys | Gln | Leu | Arg | Phe |  |
|  |  |  |  | 325 |  |  |  |  | 330 |  |  |  |  | 335 |  |

| GCA | CTC | AAG | ACC | TAC | TTT | CCT | TAC | ACT | TCT | CCA | TCT | CTT | GCC | ATG | 1305 |
|---|---|---|---|---|---|---|---|---|---|---|---|---|---|---|---|
| Ala | Leu | Lys | Thr | Tyr | Phe | Pro | Tyr | Thr | Ser | Pro | Ser | Leu | Ala | Met |  |
|  |  |  |  | 340 |  |  |  |  | 345 |  |  |  |  | 350 |  |

| GTG | CTG | CTG | CAA | GAC | CCT | CAA | GAT | ATC | CCT | CGG | GGA | CAC | TGG | CTC | 1350 |
|---|---|---|---|---|---|---|---|---|---|---|---|---|---|---|---|
| Val | Leu | Leu | Gln | Asp | Pro | Gln | Asp | Ile | Pro | Arg | Gly | His | Trp | Leu |  |
|  |  |  |  | 355 |  |  |  |  | 360 |  |  |  |  | 365 |  |

| CAG | ACA | CTG | AAG | CAT | ATT | TCT | GAA | CTG | CTC | AGA | GAA | GCA | GTT | GAA | 1395 |
|---|---|---|---|---|---|---|---|---|---|---|---|---|---|---|---|

```
Gln Thr Leu Lys His Ile Ser Glu Leu Leu Arg Glu Ala Val Glu
            370             375             380

GAC CAG ACT CAT GGG TCC TGC GGA GGT CCC TTT GAG AGC TGG TTC         1440
Asp Gln Thr His Gly Ser Cys Gly Gly Pro Phe Glu Ser Trp Phe
            385             390             395

CTG TTC ATT CAC TTC GGA GGA TGG GCT GAG ATG GTG GCA GAG CAA         1485
Leu Phe Ile His Phe Gly Gly Trp Ala Glu Met Val Ala Glu Gln
            400             405             410

TTA CTG ATG TCG GCA GCC GAA CCC CCC ACG GCC CTG CTG TGG CTC         1530
Leu Leu Met Ser Ala Ala Glu Pro Pro Thr Ala Leu Leu Trp Leu
            415             420             425

TTG GCC TTC TAC TAC GGC CCC CGT GAT GGG AGG CAG CAG AGA GCA         1575
Leu Ala Phe Tyr Tyr Gly Pro Arg Asp Gly Arg Gln Gln Arg Ala
            430             435             440

CAG ACT ATG GTC CAG GTG AAG GCC GTG CTG GGC CAC CTC CTG GCA         1620
Gln Thr Met Val Gln Val Lys Ala Val Leu Gly His Leu Leu Ala
            445             450             455

ATG TCC AGA AGC AGC AGC CTC TCA GCC CAG GAC CTG CAG ACG GTA         1665
Met Ser Arg Ser Ser Ser Leu Ser Ala Gln Asp Leu Gln Thr Val
            460             465             470

GCA GGA CAG GGC ACA GAC ACA GAC CTC AGA GCT CCT GCA CAA CAG         1710
Ala Gly Gln Gly Thr Asp Thr Asp Leu Arg Ala Pro Ala Gln Gln
            475             480             485

CTG ATC AGG CAC CTT CTC CTC AAC TTC CTG CTC TGG GCT CCT GGA         1755
Leu Ile Arg His Leu Leu Leu Asn Phe Leu Leu Trp Ala Pro Gly
            490             495             500

GGC CAC ACG ATC GCC TGG GAT GTC ATC ACC CTG ATG GCT CAC ACT         1800
Gly His Thr Ile Ala Trp Asp Val Ile Thr Leu Met Ala His Thr
            505             510             515

GCT GAG ATA ACT CAC GAG ATC ATT GGC TTT CTT GAC CAG ACC TTG         1845
Ala Glu Ile Thr His Glu Ile Ile Gly Phe Leu Asp Gln Thr Leu
            520             525             530

TAC AGA TGG AAT CGT CTT GGC ATT GAA AGC CCT AGA TCA GAA AAA         1890
Tyr Arg Trp Asn Arg Leu Gly Ile Glu Ser Pro Arg Ser Glu Lys
            535             540             545

CTG GCC CGA GAG CTC CTT AAA GAG CTG CGA ACT CAA GTC TAG A           1933
Leu Ala Arg Glu Leu Leu Lys Glu Leu Arg Thr Gln Val
            550             555

AGGCACGCAG GCCGTGTGGG TGCCCGGCGT GAGGGATCAG GCTCGCCAGG       1983
GCCACAGGAC AGGTGATGAC CTGTGGCCAC GCATTTGTGG AGTAAGTGCC CTCGCTGGGC   2043
TGTGAGAATG AGCTGTACAC ATCTTGGGAC AATCTGCTAG TATCTATTTT ACAAAATGCA   2103
GAGCCAGGTC CCTCAGCCCA GACTCAGTCA GACATGTTCA CTAATGACTC AAGTGAGCTT   2163
CGGTACTCCT GGTGCCCGCC CGGCCAGACC GTCAGCTTGA TAATTACTAA AGCAAAGGCC   2223
TGGGTGGGAG AACAGGTTTC TAGTTTTTAC CCAAGTCAAG CTGCACATCT ATTATTTAAA   2283
AATTCAAAGT CTTAGAACCA AGAATTTGGT CATGAACCAT TAAAGAATTT AGAGAGAA    2341
```

( 2 ) INFORMATION FOR SEQ ID NO: 3:

( i ) SEQUENCE CHARACTERISTICS:
        ( A ) LENGTH: 3147 base pairs
        ( B ) TYPE: Nucleic Acid
        ( C ) STRANDEDNESS: Double stranded
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
  ( A ) ORGANISM: Homo sapiens ( v i i ) IMMEDIATE SOURCE:
  ( A ) LIBRARY: Human cDNA ( v i i i ) POSITION IN GENOME: (of corresponding genomic gene)
  ( A ) CHROMOSOME/SEGMENT: 9q
  ( B ) MAP POSITION: 22.3
  ( C ) UNITS:

( x ) SEQUENCE DESCRIPTION: SEQ ID NO: 3:

```
                              ACTGCTGACA CGTGTGCGCG CGCGCGGCTC CACTGCCGGG         40

CGACCGCGGG AAAATTCCAA AAAAACTCAA AAAGCCAATA CGAGGCAAAG CCAAATTTTC              100

AAGCCACAGA TCCCGGGCGG TGGCTTCCTT TCCGCCACTG CCCAAACTGC TGAAGCAGCT              160

CCCGCGAGGA CCACCCGATT TAATGTGTGC CGACCATTTC CTTCAGTGCT GGACAGGCTG              220

CTGTGAAGGG ACATCACCTT TTCGCTTTTT CCAAG ATG GCT CAA GAT TCA                    270
                                       Met Ala Gln Asp Ser
                                        1               5

GTA GAT CTT TCT TGT GAT TAT CAG TTT TGG ATG CAG AAG CTT TCT                   315
Val Asp Leu Ser Cys Asp Tyr Gln Phe Trp Met Gln Lys Leu Ser
             10                  15                      20

GTA TGG GAT CAG GCT TCC ACT TTG GAA ACC CAG CAA GAC ACC TGT                   360
Val Trp Asp Gln Ala Ser Thr Leu Glu Thr Gln Gln Asp Thr Cys
             25                  30                      35

CTT CAC GTG GCT CAG TTC CAG GAG TTC CTA AGG AAG ATG TAT GAA                   405
Leu His Val Ala Gln Phe Gln Glu Phe Leu Arg Lys Met Tyr Glu
             40                  45                      50

GCC TTG AAA GAG ATG GAT TCT AAT ACA GTC ATT GAA AGA TTC CCC                   450
Ala Leu Lys Glu Met Asp Ser Asn Thr Val Ile Glu Arg Phe Pro
             55                  60                      65

ACA ATT GGT CAA CTG TTG GCA AAA GCT TGT TGG AAT CCT TTT ATT                   495
Thr Ile Gly Gln Leu Leu Ala Lys Ala Cys Trp Asn Pro Phe Ile
             70                  75                      80

TTA GCA TAT GAT GAA AGC CAA AAA ATT CTA ATA TGG TGC TTA TGT                   540
Leu Ala Tyr Asp Glu Ser Gln Lys Ile Leu Ile Trp Cys Leu Cys
             85                  90                      95

TGT CTA ATT AAC AAA GAA CCA CAG AAT TCT GGA CAA TCA AAA CTT                   585
Cys Leu Ile Asn Lys Glu Pro Gln Asn Ser Gly Gln Ser Lys Leu
            100                 105                     110

AAC TCC TGG ATA CAG GGT GTA TTA TCT CAT ATA CTT TCA GCA CTC                   630
Asn Ser Trp Ile Gln Gly Val Leu Ser His Ile Leu Ser Ala Leu
            115                 120                     125

AGA TTT GAT AAA GAA GTT GCT CTT TTC ACT CAA GGT CTT GGG TAT                   675
Arg Phe Asp Lys Glu Val Ala Leu Phe Thr Gln Gly Leu Gly Tyr
            130                 135                     140

GCA CCT ATA GAT TAC TAT CCT GGT TTG CTT AAA AAT ATG GTT TTA                   720
Ala Pro Ile Asp Tyr Tyr Pro Gly Leu Leu Lys Asn Met Val Leu
            145                 150                     155

TCA TTA GCG TCT GAA CTC AGA GAG AAT CAT CTT AAT GGA TTT AAC                   765
Ser Leu Ala Ser Glu Leu Arg Glu Asn His Leu Asn Gly Phe Asn
            160                 165                     170

ACT CAA AGG CGA ATG GCT CCC GAG CGA GTG GCG TCC CTG TCA CGA                   810
Thr Gln Arg Arg Met Ala Pro Glu Arg Val Ala Ser Leu Ser Arg
            175                 180                     185

GTT TGT GTC CCA CTT ATT ACC CTG ACA GAT GTT GAC CCC CTG GTG                   855
Val Cys Val Pro Leu Ile Thr Leu Thr Asp Val Asp Pro Leu Val
            190                 195                     200

GAG GCT CTC CTC ATC TGT CAT GGA CGT GAA CCT CAG GAA ATC CTC                   900
Glu Ala Leu Leu Ile Cys His Gly Arg Glu Pro Gln Glu Ile Leu
            205                 210                     215
```

```
CAG CCA GAG TTC TTT GAG GCT GTA AAC GAG GCC ATT TTG CTG AAG        945
Gln Pro Glu Phe Phe Glu Ala Val Asn Glu Ala Ile Leu Leu Lys
        220             225                 230

AAG ATT TCT CTC CCC ATG TCA GCT GTA GTC TGC CTC TGG CTT CGG        990
Lys Ile Ser Leu Pro Met Ser Ala Val Val Cys Leu Trp Leu Arg
        235             240                 245

CAC CTT CCC AGC CTT GAA AAA GCA ATG CTG CAT CTT TTT GAA AAG       1035
His Leu Pro Ser Leu Glu Lys Ala Met Leu His Leu Phe Glu Lys
        250             255                 260

CTA ATC TCC AGT GAG AGA AAT TGT CTG AGA AGG ATC GAA TGC TTT       1080
Leu Ile Ser Ser Glu Arg Asn Cys Leu Arg Arg Ile Glu Cys Phe
        265             270                 275

ATA AAA GAT TCA TCG CTG CCT CAA GCA GCC TGC CAC CCT GCC ATA       1125
Ile Lys Asp Ser Ser Leu Pro Gln Ala Ala Cys His Pro Ala Ile
        280             285                 290

TTC CGG GTT GTT GAT GAG ATG TTC AGG TGT GCA CTC CTG GAA ACC       1170
Phe Arg Val Val Asp Glu Met Phe Arg Cys Ala Leu Leu Glu Thr
        295             300                 305

GAT GGG GCC CTG GAA ATC ATA GCC ACT ATT CAG GTG TTT ACG CAG       1215
Asp Gly Ala Leu Glu Ile Ile Ala Thr Ile Gln Val Phe Thr Gln
        310             315                 320

TGC TTT GTA GAA GCT CTG GAG AAA GCA AGC AAG CAG CTG CGG TTT       1260
Cys Phe Val Glu Ala Leu Glu Lys Ala Ser Lys Gln Leu Arg Phe
        325             330                 335

GCA CTC AAG ACC TAC TTT CCT TAC ACT TCT CCA TCT CTT GCC ATG       1305
Ala Leu Lys Thr Tyr Phe Pro Tyr Thr Ser Pro Ser Leu Ala Met
        340             345                 350

GTG CTG CTG CAA GAC CCT CAA GAT ATC CCT CGG GGA CAC TGG CTC       1350
Val Leu Leu Gln Asp Pro Gln Asp Ile Pro Arg Gly His Trp Leu
        355             360                 365

CAG ACA CTG AAG CAT ATT TCT GAA CTG CTC AGA GAA GCA GTT GAA       1395
Gln Thr Leu Lys His Ile Ser Glu Leu Leu Arg Glu Ala Val Glu
        370             375                 380

GAC CAG ACT CAT GGG TCC TGC GGA GGT CCC TTT GAG AGC TGG TTC       1440
Asp Gln Thr His Gly Ser Cys Gly Gly Pro Phe Glu Ser Trp Phe
        385             390                 395

CTG TTC ATT CAC TTC GGA GGA TGG GCT GAG ATG GTG GCA GAG CAA       1485
Leu Phe Ile His Phe Gly Gly Trp Ala Glu Met Val Ala Glu Gln
        400             405                 410

TTA CTG ATG TCG GCA GCC GAA CCC CCC ACG GCC CTG CTG TGG CTC       1530
Leu Leu Met Ser Ala Ala Glu Pro Pro Thr Ala Leu Leu Trp Leu
        415             420                 425

TTG GCC TTC TAC TAC GGC CCC CGT GAT GGG AGG CAG CAG AGA GCA       1575
Leu Ala Phe Tyr Tyr Gly Pro Arg Asp Gly Arg Gln Gln Arg Ala
        430             435                 440

CAG ACT ATG GTC CAG GTG AAG GCC GTG CTG GGC CAC CTC CTG GCA       1620
Gln Thr Met Val Gln Val Lys Ala Val Leu Gly His Leu Leu Ala
        445             450                 455

ATG TCC AGA AGC AGC AGC CTC TCA GCC CAG GAC CTG CAG ACG GTA       1665
Met Ser Arg Ser Ser Ser Leu Ser Ala Gln Asp Leu Gln Thr Val
        460             465                 470

GCA GGA CAG GGC ACA GAC ACA GAC CTC AGA GCT CCT GCA CAA CAG       1710
Ala Gly Gln Gly Thr Asp Thr Asp Leu Arg Ala Pro Ala Gln Gln
        475             480                 485

CTG ATC AGG CAC CTT CTC CTC AAC TTC CTG CTC TGG GCT CCT GGA       1755
Leu Ile Arg His Leu Leu Leu Asn Phe Leu Leu Trp Ala Pro Gly
        490             495                 500

GGC CAC ACG ATC GCC TGG GAT GTC ATC ACC CTG ATG GCT CAC ACT       1800
Gly His Thr Ile Ala Trp Asp Val Ile Thr Leu Met Ala His Thr
        505             510                 515
```

```
GCT GAG ATA ACT CAC GAG ATC ATT GGC TTT CTT GAC CAG ACC TTG        1845
Ala Glu Ile Thr His Glu Ile Ile Gly Phe Leu Asp Gln Thr Leu
                520             525             530

TAC AGA TGG AAT CGT CTT GGC ATT GAA AGC CCT AGA TCA GAA AAA        1890
Tyr Arg Trp Asn Arg Leu Gly Ile Glu Ser Pro Arg Ser Glu Lys
                535             540             545

CTG GCC CGA GAG CTC CTT AAA GAG CTG CGA ACT CAA GTC TAG A          1933
Leu Ala Arg Glu Leu Leu Lys Glu Leu Arg Thr Gln Val
                550             555

AGGCACGCAG GCCGTGTGGG TGCCCGGCGT GAGGGATCAG GCTCGCCAGG             1983

GCCACAGGAC AGGTGATGAC CTGTGGCCAC GCATTTGTGG AGTAAGTGCC CTCGCTGGGC  2043

TGTGAGAATG AGCTGTACAC ATCTTGGGAC AATCTGCTAG TATCTATTTT ACAAAATGCA  2103

GAGCCAGGTC CCTCAGCCCA GACTCAGTCA GACATGTTCA CTAATGACTC AAGTGAGCTT  2163

CGGTACTCCT GGTGCCCGCC CGGCCAGACC GTCAGCTTGA TAATTACTAA AGCAAAGGCC  2223

TGGGTGGGAG AACAGGTTTC TAGTTTTTAC CCAAGTCAAG CTGCACATCT ATTATTTAAA  2283

AATTCAAAGT CTTAGAACCA AGAATTTGGT CATGAACCAT TAAAGAATTT AGAGAGAACT  2343

TAGCTCTTTT TAGACTCTTT TTAGGAGTCA GGGATCTGGG ATAAAGCCAC ACTGTCTTGC  2403

TGTATGGAGA AATTCTTCAA GGGGAGTCAG GGTCCCTCAG GCTTCCCTTG TGTCTCCCTG  2463

GACCTGCCTG ACAGGCCACA GGAGCAGACA GCACACCCAA GCCCGGGCCT CCGGCACACT  2523

CTTTCCACTC TGTATTTGCT AAATGATGCT AACTGCTACC AAAAGGCCCT TGGGACATCA  2583

GAGGAGCCGG CAGCGAAGGT AGAGGATGTG TTCCAGAAAC ATTAGAAGGC AGGATTAATT  2643

CAGTTAGTTA GTCTCTTGTT AAATGGAAAT GGGAATTGGA AATTCCTGAT AAAGAATTGG  2703

CCTGGCTGGG TGCAGTGGCT CACACCTGTG ATCCCAGCAC TTTGGGAGGC CAAGGCAGGG  2763

GGATTACTTC AGCCCAGGAG TTCCAGACTG CCTGGCTAAC ATGGCAATAC CCTATCTCTA  2823

CTAAAAATAC AAAAATTATC GGGGTGCAAT GGCATGCATC TGTAACCCAG CTATTCAAGA  2883

GGCTGAGGCA TGAGGATCTC TTGAACCCGG GAGGTGGGAG TTGTAGTGAG CCGAGATCAT  2943

GACACTGCAC TCCAGCCTGG GCAACAGAGC GAGACCATCT CTTAAAAAAA GGCATTGTTA  3003

GTGTAACTCA AGGTTAACAT TTATTTCATG TCAGTACAGG GTGCTTTTTC CTTTCAGGGA  3063

CATTCTGGAA TTGTATTGGT TGTACATTCT TTTGTGTCTA TTCTGTTTGT CAAGTGAGTC  3123

AAGACTTGCT TTTGTCCATT TTGA                                        3147
```

( 2 ) INFORMATION FOR SEQ ID NO:4:

( i ) SEQUENCE CHARACTERISTICS:
        ( A ) LENGTH: 558 amino acids
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: yes ( i v ) ANTI-SENSE: no ( v ) FRAGMENT TYPE:

( v i ) ORIGINAL SOURCE:
        ( A ) ORGANISM: Homo sapiens ( x ) SEQUENCE DESCRIPTION: SEQ ID NO: 4:

```
Met Ala Gln Asp Ser Val Asp Leu Ser Cys Asp Tyr Gln Phe Trp
 1               5                  10                  15
```

| | | | | | | | | | | | | |
|---|---|---|---|---|---|---|---|---|---|---|---|---|
|Met|Gln|Lys|Leu|Ser 20|Val|Trp|Asp|Gln|Ala 25|Ser|Thr|Leu|Glu|Thr 30|
|Gln|Gln|Asp|Thr|Cys 35|Leu|His|Val|Ala|Gln 40|Phe|Gln|Glu|Phe|Leu 45|
|Arg|Lys|Met|Tyr|Glu 50|Ala|Leu|Lys|Glu|Met 55|Asp|Ser|Asn|Thr|Val 60|
|Ile|Glu|Arg|Phe|Pro 65|Thr|Ile|Gly|Gln|Leu 70|Leu|Ala|Lys|Ala|Cys 75|
|Trp|Asn|Pro|Phe|Ile 80|Leu|Ala|Tyr|Asp|Glu 85|Ser|Gln|Lys|Ile|Leu 90|
|Ile|Trp|Cys|Leu|Cys 95|Cys|Leu|Ile|Asn|Lys 100|Glu|Pro|Gln|Asn|Ser 105|
|Gly|Gln|Ser|Lys|Leu 110|Asn|Ser|Trp|Ile|Gln 115|Gly|Val|Leu|Ser|His 120|
|Ile|Leu|Ser|Ala|Leu 125|Arg|Phe|Asp|Lys|Glu 130|Val|Ala|Leu|Phe|Thr 135|
|Gln|Gly|Leu|Gly|Tyr 140|Ala|Pro|Ile|Asp|Tyr 145|Tyr|Pro|Gly|Leu|Leu 150|
|Lys|Asn|Met|Val|Leu 155|Ser|Leu|Ala|Ser|Glu 160|Leu|Arg|Glu|Asn|His 165|
|Leu|Asn|Gly|Phe|Asn 170|Thr|Gln|Arg|Arg|Met 175|Ala|Pro|Glu|Arg|Val 180|
|Ala|Ser|Leu|Ser|Arg 185|Val|Cys|Val|Pro|Leu 190|Ile|Thr|Leu|Thr|Asp 195|
|Val|Asp|Pro|Leu|Val 200|Glu|Ala|Leu|Leu|Ile 205|Cys|His|Gly|Arg|Glu 210|
|Pro|Gln|Glu|Ile|Leu 215|Gln|Pro|Glu|Phe|Phe 220|Glu|Ala|Val|Asn|Glu 225|
|Ala|Ile|Leu|Leu|Lys 230|Lys|Ile|Ser|Leu|Pro 235|Met|Ser|Ala|Val|Val 240|
|Cys|Leu|Cys|Val|Arg 245|His|Leu|Pro|Ser|Leu 250|Glu|Lys|Ala|Met|Leu 255|
|His|Leu|Phe|Glu|Lys 260|Leu|Ile|Ser|Ser|Glu 265|Arg|Asn|Cys|Leu|Arg 270|
|Arg|Ile|Glu|Cys|Phe 275|Ile|Lys|Asp|Ser|Ser 280|Leu|Pro|Gln|Ala|Ala 285|
|Cys|His|Pro|Ala|Ile 290|Phe|Arg|Val|Val|Asp 295|Glu|Met|Phe|Arg|Cys 300|
|Ala|Leu|Leu|Glu|Thr 305|Asp|Gly|Ala|Leu|Glu 310|Ile|Ile|Ala|Thr|Ile 315|
|Gln|Val|Phe|Thr|Gln 320|Cys|Phe|Val|Glu|Ala 325|Leu|Glu|Lys|Ala|Ser 330|
|Lys|Gln|Leu|Arg|Phe 335|Ala|Leu|Lys|Thr|Tyr 340|Phe|Pro|Tyr|Thr|Ser 345|
|Pro|Ser|Leu|Ala|Met 350|Val|Leu|Leu|Gln|Asp 355|Pro|Gln|Asp|Ile|Pro 360|
|Arg|Gly|His|Trp|Leu 365|Gln|Thr|Leu|Lys|His 370|Ile|Ser|Glu|Leu|Leu 375|
|Arg|Glu|Ala|Val|Glu 380|Asp|Gln|Thr|His|Gly 385|Ser|Cys|Gly|Gly|Pro 390|
|Phe|Glu|Ser|Trp|Phe 395|Leu|Phe|Ile|His|Phe 400|Gly|Gly|Trp|Ala|Glu 405|
|Met|Val|Ala|Glu|Gln|Leu|Leu|Met|Ser|Ala|Ala|Glu|Pro|Pro|Thr|

|     |     |     |     | 410 |     |     |     | 415 |     |     |     | 420 |
|---|---|---|---|---|---|---|---|---|---|---|---|---|

Ala Leu Leu Trp Leu Leu Ala Phe Tyr Tyr Gly Pro Arg Asp Gly
                425                     430                 435

Arg Gln Gln Arg Ala Gln Thr Met Val Gln Val Lys Ala Val Leu
                440                     445                 450

Gly His Leu Leu Ala Met Ser Arg Ser Ser Ser Leu Ser Ala Gln
                455                     460                 465

Asp Leu Gln Thr Val Ala Gly Gln Gly Thr Asp Thr Asp Leu Arg
                470                     475                 480

Ala Pro Ala Gln Gln Leu Ile Arg His Leu Leu Leu Asn Phe Leu
                485                     490                 495

Leu Trp Ala Pro Gly Gly His Thr Ile Ala Trp Asp Val Ile Thr
                500                     505                 510

Leu Met Ala His Thr Ala Glu Ile Thr His Glu Ile Ile Gly Phe
                515                     520                 525

Leu Asp Gln Thr Leu Tyr Arg Trp Asn Arg Leu Gly Ile Glu Ser
                530                     535                 540

Pro Arg Ser Glu Lys Leu Ala Arg Glu Leu Leu Lys Glu Leu Arg
                545                     550                 555

Thr Gln Val ( 2 ) INFORMATION FOR SEQ ID NO: 5:

( i ) SEQUENCE CHARACTERISTICS:
        ( A ) LENGTH: 98 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 5:

```
GTAAGTAGTG GACCAGAATA ATGAAATTAT TTCTGACTT CAGGGACTCT                    50
ACCAGATTTC ACCAAGACAG AATGCCACCC AGAATCGGGA CTTGTGGT                    98
```

( 2 ) INFORMATION FOR SEQ ID NO: 6:

( i ) SEQUENCE CHARACTERISTICS:
        ( A ) LENGTH: 81 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 6:

```
TTCCCTCAAT CTATAATGTC AGTTCAGTAT TTCTAAGTTG CATAATGCCT                    50
TTACTGACCA AAATTTATTT TTCTTTCACA G                                       81
```

( 2 ) INFORMATION FOR SEQ ID NO: 7:

( i ) SEQUENCE CHARACTERISTICS:
        ( A ) LENGTH: 69 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 7:

```
GTAAGAATCA AAAACGTGTC CTCTCAAAAA TGGCTATTTT AATCTTTGCA        50

TTGTTTCACA GAGGCTTAC                                          69
```

( 2 ) INFORMATION FOR SEQ ID NO: 8:

( i ) SEQUENCE CHARACTERISTICS:
        ( A ) LENGTH: 98 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 8:

```
TAGTAGTTTG AGATTTTCCT AAATATAATG TTTACAGTGT TTTTTATATT        50

AATGATTTTT TCTGCTTGAT AAAACTTATT AAGTTTCCT TTTTGTAG           98
```

( 2 ) INFORMATION FOR SEQ ID NO: 9:

( i ) SEQUENCE CHARACTERISTICS:
        ( A ) LENGTH: 70 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 9:

```
GTAAGAGAGT AAATCTTGCT CTGCACTTCT TTGAATTAAA TTGATTATTT        50

AAAAGTGCTG CTTAAAAAAA                                         70
```

( 2 ) INFORMATION FOR SEQ ID NO: 10:

( i ) SEQUENCE CHARACTERISTICS:
        ( A ) LENGTH: 78 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
    ( A ) ORGANISM: Homo sapiens ( x ) SEQUENCE DESCRIPTION: SEQ ID NO: 10:

| | | | | | |
|---|---|---|---|---|---|
| TAAATTGTAG | GCATTGTACA | TAAAAGGCAC | TTGCATTTAC | TTTTAAAGAA | 50 |
| GTTAACTTTT | TCTGTTTATG | TTTTTAG | | | 78 |

( 2 ) INFORMATION FOR SEQ ID NO: 11:

( i ) SEQUENCE CHARACTERISTICS:
        ( A ) LENGTH: 52 base pairs
        ( B ) TYPE: Nucleic Acid
        ( C ) STRANDEDNESS: Double stranded
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 11:

| | | | | | |
|---|---|---|---|---|---|
| GTGAGTATTT | AATATTTATC | ACTTTGAAA | TGTTAATGC | TGAATGTGCC | 50 |
| AT | | | | | 52 |

( 2 ) INFORMATION FOR SEQ ID NO: 12:

( i ) SEQUENCE CHARACTERISTICS:
        ( A ) LENGTH: 60 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 12:

| | | | | | |
|---|---|---|---|---|---|
| TAGAACTGAT | GTAATCCTGT | TTGCAGCGTG | AGTTAACCTG | CAACTGATTT | 50 |
| TGTTTTACAG | | | | | 60 |

( 2 ) INFORMATION FOR SEQ ID NO: 13:

( i ) SEQUENCE CHARACTERISTICS:
        ( A ) LENGTH: 72 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 13:

GTAGGTGTTA AACTAAACAT CCTTCTTCTC AGGTTTCAAA ATGTATCAGT      50

TTGGTTATGA GAGGAAAATT TT      72

( 2 ) INFORMATION FOR SEQ ID NO: 14:

( i ) SEQUENCE CHARACTERISTICS:
        ( A ) LENGTH: 61 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 14:

ATATGTCCTT AATTATGCAT GGCTCTTAGA TTTGAGTGAT TATTTCTTAT      50

TTCTTCCATA G      61

( 2 ) INFORMATION FOR SEQ ID NO: 15:

( i ) SEQUENCE CHARACTERISTICS:
        ( A ) LENGTH: 71 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 15:

GTAAGTGGCA AATGTTTCCT GTCATCCTGC GTCGTTTTTC CTTTCTTAG      50

AAGGCTGTGG TGTGTTGGAA A      71

( 2 ) INFORMATION FOR SEQ ID NO: 16:

( i ) SEQUENCE CHARACTERISTICS:
        ( A ) LENGTH: 53 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 16:

TTTTTTCAGT GAGCCATTTC TGTTTAAAAT TTGTTTATT TCTTTCTGAA      50

AAG      53

( 2 ) INFORMATION FOR SEQ ID NO: 17:

( i ) SEQUENCE CHARACTERISTICS:
        ( A ) LENGTH: 63 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 17:

```
GTACGTACTG  GGTTTTGATG  AAGGGAAAAA  TCCTTGAAGG  ACATGCTTGG      50
ACTCATTTCT  TTT                                                 63
```

( 2 ) INFORMATION FOR SEQ ID NO: 18:

( i ) SEQUENCE CHARACTERISTICS:
        ( A ) LENGTH: 80 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 18:

```
AACTCCTTTG  GCTGATAATA  GCAAGTTT Y T  GAGAAAGTGC  TTGTGATATT    50
TCACATTCTC  ATGGTCTTCT  CCTTTTACAG                              80
```

( 2 ) INFORMATION FOR SEQ ID NO: 19:

( i ) SEQUENCE CHARACTERISTICS:
        ( A ) LENGTH: 101 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 19:

```
GTAAACGTTA  CACTGTTTCT  TCTAGTAATT  GATGTAAAAA  AGGTTCCATT      50
TCCAAGCATG  AATCAGAAAA  TGTTGTGGTA  GTCTCTGGCT  GTATCATGGG     100
G                                                              101
```

( 2 ) INFORMATION FOR SEQ ID NO: 20:

( i ) SEQUENCE CHARACTERISTICS:
        ( A ) LENGTH: 110 base pairs
        ( B ) TYPE: Nucleic Acid
        ( C ) STRANDEDNESS: Double stranded ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
            ( A ) ORGANISM: Homo sapiens ( x ) SEQUENCE DESCRIPTION: SEQ ID NO: 20:

AAGCTTATGG CACAAAAAAA GTGTTTCTAC TTTTCCCTTA TACAGTGCAG        50

GTTTTCATGT TTGCCGGATT ACTTGTTAAA CGTGTTCTGA TCTGACTTTG        100

CATTGTTCAG        110

( 2 ) INFORMATION FOR SEQ ID NO: 21:

( i ) SEQUENCE CHARACTERISTICS:
            ( A ) LENGTH: 105 base pairs
            ( B ) TYPE: Nucleic Acid
            ( C ) STRANDEDNESS: Double stranded
            ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
            ( A ) ORGANISM: Homo sapiens ( x ) SEQUENCE DESCRIPTION: SEQ ID NO: 21:

GTTTGTTATA TCACATATAT TACTCATTCA CCCAGAGAAT AAGACGCTGT        50

TGAGAGTATT TGGACAAGA GCACTTTATT TTCAATAATT TTGATGGACT        100

GTTTT        105

( 2 ) INFORMATION FOR SEQ ID NO: 22:

( i ) SEQUENCE CHARACTERISTICS:
            ( A ) LENGTH: 72 base pairs
            ( B ) TYPE: Nucleic Acid
            ( C ) STRANDEDNESS: Double stranded
            ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
            ( A ) ORGANISM: Homo sapiens ( x ) SEQUENCE DESCRIPTION: SEQ ID NO: 22:

AGAGTTTTGT ATTTTCCTGA CCCCGTTTCA ATCTTAATGT TCATGCTCTT        50

TGGATTTTCC ATCCTGTGGC AG        72

( 2 ) INFORMATION FOR SEQ ID NO: 23:

( i ) SEQUENCE CHARACTERISTICS:
            ( A ) LENGTH: 64 base pairs
            ( B ) TYPE: Nucleic Acid
            ( C ) STRANDEDNESS: Double stranded
            ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
    ( A ) ORGANISM: Homo sapiens ( x ) SEQUENCE DESCRIPTION: SEQ ID NO: 23:

| | | | | |
|---|---|---|---|---|
| GTGAGTTAGG | GTTGACTTGC | CCACATCAGA | ATGANNTCCT | GGGAAGAGCA | 50 |
| TTGTCAAATT | ATGA | | | | 64 |

( 2 ) INFORMATION FOR SEQ ID NO: 24:

( i ) SEQUENCE CHARACTERISTICS:
    ( A ) LENGTH: 116 base pairs
    ( B ) TYPE: Nucleic Acid
    ( C ) STRANDEDNESS: Double stranded
    ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
    ( A ) ORGANISM: Homo sapiens ( x ) SEQUENCE DESCRIPTION: SEQ ID NO: 24:

| | | | | |
|---|---|---|---|---|
| GTGAACCAGA | AGTAAAGGGC | GTCTCCCAAA | GACTCTTCAG | GTCATCCCTG | 50 |
| CAGGTGGTTC | CTCATGGGGT | TGACATTTCC | TCAGTTGCCC | TCTGACGTAT | 100 |
| CTCTCTCCAC | CCGCAG | | | | 116 |

( 2 ) INFORMATION FOR SEQ ID NO: 25:

( i ) SEQUENCE CHARACTERISTICS:
    ( A ) LENGTH: 56 base pairs
    ( B ) TYPE: Nucleic Acid
    ( C ) STRANDEDNESS: Double stranded
    ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
    ( A ) ORGANISM: Homo sapiens ( x ) SEQUENCE DESCRIPTION: SEQ ID NO: 25:

| | | | | |
|---|---|---|---|---|
| GTGAGCAAAC | ACTGACCACT | CCCAAATCTG | CTTCACACAT | GGTTTCCCTA | 50 |
| GATCCT | | | | | 56 |

( 2 ) INFORMATION FOR SEQ ID NO: 26:

( i ) SEQUENCE CHARACTERISTICS:
    ( A ) LENGTH: 61 base pairs
    ( B ) TYPE: Nucleic Acid
    ( C ) STRANDEDNESS: Double stranded
    ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
    ( A ) ORGANISM: Homo sapiens ( x ) SEQUENCE DESCRIPTION: SEQ ID NO: 26:

AAAAACCCAA AGGAAGAAGA ATTTAGGTTG TCAACTGCCA TGTGTTCTGC  50

CTCTGTTCCA G  61

( 2 ) INFORMATION FOR SEQ ID NO: 27:

( i ) SEQUENCE CHARACTERISTICS:
        ( A ) LENGTH: 66 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 27:

GTGGGTAGCA TTCCCCACTG CATGTGTTTG GGGNNGGCTC TGGGGGGCTA  50

GAGGAGCAAG GAGAGG  66

( 2 ) INFORMATION FOR SEQ ID NO: 28:

( i ) SEQUENCE CHARACTERISTICS:
        ( A ) LENGTH: 63 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 28:

AATCCTAGAA GTATGTCTGT CCTGNNTCTC CTAACCTCTC CCCTGTGAAA  50

TACTATTGCC CAG  63

( 2 ) INFORMATION FOR SEQ ID NO: 29:

( i ) SEQUENCE CHARACTERISTICS:
        ( A ) LENGTH: 46 base pairs
        ( B ) TYPE: Nucleic Acid
        ( C ) STRANDEDNESS: Double stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 29:

GTAAGTCTCC CTGTGGTCCA GCATCCTAGT CAAGGAGAGG ACAGCA  46

( 2 ) INFORMATION FOR SEQ ID NO: 30:

5,681,942

-continued ( i ) SEQUENCE CHARACTERISTICS:
  ( A ) LENGTH: 117 base pairs
  ( B ) TYPE: Nucleic Acid
  ( C ) STRANDEDNESS: Double stranded
  ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
  ( A ) ORGANISM: Homo sapiens ( x ) SEQUENCE DESCRIPTION: SEQ ID NO: 30:

| | | | | | |
|---|---|---|---|---|---|
| TGGAAATGCT | GGATAGGGCT | TCTTTCAGGG | ACTGGGTGGT | TATGGTCCGT | 50 |
| CCCTGGACAA | AGGACAAATC | TGTCTGGAAA | GTGTTTTAAT | TTGCCTTCTC | 100 |
| TTCTGTCCTG | ATTGCAG | | | | 117 |

( 2 ) INFORMATION FOR SEQ ID NO: 31:

( i ) SEQUENCE CHARACTERISTICS:
  ( A ) LENGTH: 2896 base pairs
  ( B ) TYPE: Nucleic Acid
  ( C ) STRANDEDNESS: Double stranded
  ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
  ( A ) ORGANISM: Mouse ( x ) SEQUENCE DESCRIPTION: SEQ ID NO: 31:

| | | | | | |
|---|---|---|---|---|---|
| AATTCCCGCA | CGCGCAGTGC | ACTCCCTTGC | GGCCGCGGGA | AAATTCCAAA | CACGTCAAAA | 60 |
| CAAAAAAGGT | TCCGTGAGCT | GTGCCAAGTT | TTCAAGCCGC | AGAAGCCGGG | CGGTGGCTTC | 120 |
| TTTTCCGCCG | CAGCCCAGTC | TGCTGAGGCA | GCTCTGGGTG | AGGACCACCC | GGGAAGACCG | 180 |
| CCGTTTCCTG | CTAGGGCAGA | GAAGACTCGC | GAGAACGTGC | GCCCGAGTCT | CAACGTGGGC | 240 |
| GAGCCGCGCT | CCCGGGGGGT | GGAGCTGAGG | CAGGACGGCT | GCTGTGAAGG | GACAGTGCTG | 300 |

```
CTCTCAGAG ATG GCT CAG GAG TCT GCA GAC CTT GCT TCT GAC TGT              345
          Met Ala Gln Glu Ser Ala Asp Leu Ala Ser Asp Cys
           1               5                  10

CAG TCT TGG CTG CAG AAG CTT TCT GCA TGG GAA CAG GCC TCT TCT            390
Gln Ser Trp Leu Gln Lys Leu Ser Ala Trp Glu Gln Ala Ser Ser
         15                  20                  25

GAG GAA ACC CAG AAG GAC ACT TGT CTT CAC TTG TCC GGG TTC CAG            435
Glu Glu Thr Gln Lys Asp Thr Cys Leu His Leu Ser Gly Phe Gln
         30                  35                  40

GAG TTC CTG AGG CAG ATG TAT GAA ATC TTG AAG GAG ATG GAT TCT            480
Glu Phe Leu Arg Gln Met Tyr Glu Ile Leu Lys Glu Met Asp Ser
         45                  50                  55

GAT GCA ATC CTG GAA AGG TTC CCC ACA ATT GGT CAA CTG TTG GCA            525
Asp Ala Ile Leu Glu Arg Phe Pro Thr Ile Gly Gln Leu Leu Ala
         60                  65                  70

AAA GCT TGT TGG AAT CCT CTC ATC TTA GCA TAT GAT GAA AGC CAA            570
Lys Ala Cys Trp Asn Pro Leu Ile Leu Ala Tyr Asp Glu Ser Gln
         75                  80                  85

AAA ATT GTA ATA TGG TGC TTA TGT TGT CTG ATG AAC AAA GAA CCT            615
Lys Ile Val Ile Trp Cys Leu Cys Cys Leu Met Asn Lys Glu Pro
```

-continued

|  |  |  |  |  | 90 |  |  |  | 95 |  |  |  | 100 |  |  |
|---|---|---|---|---|---|---|---|---|---|---|---|---|---|---|---|
| CGG | ACT | TCT | GCA | GAG | TCA | GGA | CTT | AAC | TCG | TGG | ATC | CGG | GGT | TTG | 660 |
| Arg | Thr | Ser | Ala | Glu | Ser | Gly | Leu | Asn | Ser | Trp | Ile | Arg | Gly | Leu | |
|  |  | 105 |  |  |  |  | 110 |  |  |  |  | 115 |  |  | |
| TTA | TCT | CAT | GTA | CTT | TCT | GCA | TTC | AGA | TTC | GAC | ATG | AAA | GAA | GTT | 705 |
| Leu | Ser | His | Val | Leu | Ser | Ala | Phe | Arg | Phe | Asp | Met | Lys | Glu | Val | |
|  |  | 120 |  |  |  |  | 125 |  |  |  |  | 130 |  |  | |
| TGT | CTT | TTT | ACC | AAA | AGT | CTT | GGA | TAT | GAG | TCT | ATT | GAT | TAC | TAT | 750 |
| Cys | Leu | Phe | Thr | Lys | Ser | Leu | Gly | Tyr | Glu | Ser | Ile | Asp | Tyr | Tyr | |
|  |  | 135 |  |  |  |  | 140 |  |  |  |  | 145 |  |  | |
| CCT | AGT | TTG | CTT | AAA | AAT | ATG | GTT | TTG | TCA | TTA | GTG | TCT | GAG | CTC | 795 |
| Pro | Ser | Leu | Leu | Lys | Asn | Met | Val | Leu | Ser | Leu | Val | Ser | Glu | Leu | |
|  |  | 150 |  |  |  |  | 155 |  |  |  |  | 160 |  |  | |
| AGA | GAG | AGT | CAT | CTT | AAT | GGA | CTG | AGC | ACT | CAA | AGT | CGG | ATG | GCT | 840 |
| Arg | Glu | Ser | His | Leu | Asn | Gly | Leu | Ser | Thr | Gln | Ser | Arg | Met | Ala | |
|  |  | 165 |  |  |  |  | 170 |  |  |  |  | 175 |  |  | |
| CCT | GAG | CGC | ATG | ATG | TCC | CTG | TCA | GAA | GTT | TGT | GTC | CCT | CTT | GTC | 885 |
| Pro | Glu | Arg | Met | Met | Ser | Leu | Ser | Glu | Val | Cys | Val | Pro | Leu | Val | |
|  |  | 180 |  |  |  |  | 185 |  |  |  |  | 190 |  |  | |
| ACT | CTG | CCT | GAT | ATG | GAA | CCC | CTG | GTA | GAG | GCT | CTA | CTC | ACC | TAC | 930 |
| Thr | Leu | Pro | Asp | Met | Glu | Pro | Leu | Val | Glu | Ala | Leu | Leu | Thr | Tyr | |
|  |  | 195 |  |  |  |  | 200 |  |  |  |  | 205 |  |  | |
| CAT | GGA | CAT | GAG | CCC | CAG | GAA | GTC | CTG | GCT | CCT | GAG | TTC | TTC | GAA | 975 |
| His | Gly | His | Glu | Pro | Gln | Glu | Val | Leu | Ala | Pro | Glu | Phe | Phe | Glu | |
|  |  | 210 |  |  |  |  | 215 |  |  |  |  | 220 |  |  | |
| GCT | GTA | AAT | GAG | GCC | TTC | TTG | TCG | GAA | AAA | ATT | GTT | GTA | CCC | ACG | 1020 |
| Ala | Val | Asn | Glu | Ala | Phe | Leu | Ser | Glu | Lys | Ile | Val | Val | Pro | Thr | |
|  |  | 225 |  |  |  |  | 230 |  |  |  |  | 235 |  |  | |
| TCC | TCT | GTG | GTC | AGC | CTC | TGG | TTT | CGG | CAT | CTC | CCC | AGT | CTT | GAA | 1065 |
| Ser | Ser | Val | Val | Ser | Leu | Trp | Phe | Arg | His | Leu | Pro | Ser | Leu | Glu | |
|  |  | 240 |  |  |  |  | 245 |  |  |  |  | 250 |  |  | |
| AAA | GCA | ACG | CTG | CAT | CTT | TTT | GAA | AAG | CTT | TTC | TCC | AGC | AAG | ATA | 1110 |
| Lys | Ala | Thr | Leu | His | Leu | Phe | Glu | Lys | Leu | Phe | Ser | Ser | Lys | Ile | |
|  |  | 255 |  |  |  |  | 260 |  |  |  |  | 265 |  |  | |
| ATT | TGC | CTG | AGA | AGG | ATG | GAG | TGC | TGT | ATA | AGA | GAG | TCA | TTC | CTG | 1155 |
| Ile | Cys | Leu | Arg | Arg | Met | Glu | Cys | Cys | Ile | Arg | Glu | Ser | Phe | Leu | |
|  |  | 270 |  |  |  |  | 275 |  |  |  |  | 280 |  |  | |
| CCT | CAA | GCA | GCC | TGC | CAA | CCT | GCC | ATC | TTC | AGA | ATT | GTT | CAT | GAA | 1200 |
| Pro | Gln | Ala | Ala | Cys | Gln | Pro | Ala | Ile | Phe | Arg | Ile | Val | His | Glu | |
|  |  | 285 |  |  |  |  | 290 |  |  |  |  | 295 |  |  | |
| ATG | TTC | AGG | TTT | GTG | CTG | CTG | AAA | ACT | GAC | GGA | GCC | CCA | GAA | GTA | 1245 |
| Met | Phe | Arg | Phe | Val | Leu | Leu | Lys | Thr | Asp | Gly | Ala | Pro | Glu | Val | |
|  |  | 300 |  |  |  |  | 305 |  |  |  |  | 310 |  |  | |
| CTA | GCT | GCT | CTT | CAG | GTT | TTC | ACA | TCG | TGC | TTG | GTA | GAA | GCT | CTG | 1290 |
| Leu | Ala | Ala | Leu | Gln | Val | Phe | Thr | Ser | Cys | Leu | Val | Glu | Ala | Leu | |
|  |  | 315 |  |  |  |  | 320 |  |  |  |  | 325 |  |  | |
| AAA | AAA | GAA | AAC | AAG | CAG | CTG | ACG | TTT | GCC | CTC | AGG | ACC | TAC | TTT | 1335 |
| Lys | Lys | Glu | Asn | Lys | Gln | Leu | Thr | Phe | Ala | Leu | Arg | Thr | Tyr | Phe | |
|  |  | 330 |  |  |  |  | 335 |  |  |  |  | 340 |  |  | |
| CCT | TAC | GGT | GCT | CCA | TGT | CTT | GCT | GCA | GCG | CTG | TCC | CAG | CAC | CCT | 1380 |
| Pro | Tyr | Gly | Ala | Pro | Cys | Leu | Ala | Ala | Ala | Leu | Ser | Gln | His | Pro | |
|  |  | 345 |  |  |  |  | 350 |  |  |  |  | 355 |  |  | |
| GAA | GCA | ATC | CCA | CAG | GGA | CAC | CGG | CTC | CAG | CCT | CTG | CTG | CAC | ATT | 1425 |
| Glu | Ala | Ile | Pro | Gln | Gly | His | Arg | Leu | Gln | Pro | Leu | Leu | His | Ile | |
|  |  | 360 |  |  |  |  | 365 |  |  |  |  | 370 |  |  | |
| TCC | CAA | CTC | CTC | AGA | GAA | GCA | GTT | GAA | GAC | TGT | ACT | CGT | GGG | TCT | 1470 |
| Ser | Gln | Leu | Leu | Arg | Glu | Ala | Val | Glu | Asp | Cys | Thr | Arg | Gly | Ser | |
|  |  | 375 |  |  |  |  | 380 |  |  |  |  | 385 |  |  | |
| CCG | CGA | AAT | CCC | TTT | GAG | AGC | TGG | TTT | TTG | TTT | GTT | CAC | TTT | GGA | 1515 |
| Pro | Arg | Asn | Pro | Phe | Glu | Ser | Trp | Phe | Leu | Phe | Val | His | Phe | Gly | |

|   |   |   |   |   |   |   |   |   |   |   |   |   |   |   |   |
|---|---|---|---|---|---|---|---|---|---|---|---|---|---|---|---|
|   |   |   | 390 |   |   |   |   |   | 395 |   |   |   |   | 400 |   |
| GGA | TGG | GTT | GAC | CTG | GCT | GTG | GCA | GAG | TTA | CTG | CTG | AGG | GAG | GAA | 1560 |
| Gly | Trp | Val<br>405 | Asp | Leu | Ala | Val | Ala<br>410 | Glu | Leu | Leu | Leu | Arg<br>415 | Glu | Glu |   |
| GCT | GAG | CCT | CCT | GCT | GGC | CTG | CTG | TGG | CTC | TTG | GTG | TTC | TAT | TAC | 1605 |
| Ala | Glu | Pro<br>420 | Pro | Ala | Gly | Leu | Leu<br>425 | Trp | Leu | Leu | Val | Phe<br>430 | Tyr | Tyr |   |
| AGC | CCA | CAG | GAT | GGG | AGT | CAG | CAG | AGA | GAG | CAG | AGC | ATG | GTG | GAG | 1650 |
| Ser | Pro | Gln<br>435 | Asp | Gly | Ser | Gln | Gln<br>440 | Arg | Glu | Gln | Ser | Met<br>445 | Val | Glu |   |
| CTG | AAG | GTA | TTA | ATC | AAC | CGT | CTC | CTG | ATG | CTG | CTC | AGA | AGC | GGC | 1695 |
| Leu | Lys | Val<br>450 | Leu | Ile | Asn | Arg | Leu<br>455 | Leu | Met | Leu | Leu | Arg<br>460 | Ser | Gly |   |
| CCC | CTC | TCA | GCT | ACT | GAT | CTG | CAG | GAA | GCA | GCT | GAG | AGT | CCC | AGT | 1740 |
| Pro | Leu | Ser<br>465 | Ala | Thr | Asp | Leu | Gln<br>470 | Glu | Ala | Ala | Glu | Ser<br>475 | Pro | Ser |   |
| GGA | GAC | CCC | AGA | CCA | CCT | GTA | TGT | GGA | CAG | CTG | GTC | AGA | CGC | CTT | 1785 |
| Gly | Asp | Pro<br>480 | Arg | Pro | Pro | Val | Cys<br>485 | Gly | Gln | Leu | Val | Arg<br>490 | Arg | Leu |   |
| CTT | CTT | AGT | CTC | TTG | CTC | TGG | ACC | CCA | GAA | GGC | CAT | GCA | ATT | GTC | 1830 |
| Leu | Leu | Ser<br>495 | Leu | Leu | Leu | Trp | Thr<br>500 | Pro | Glu | Gly | His | Ala<br>505 | Ile | Val |   |
| TGG | GAA | GCT | GTC | ACC | CAT | ATG | GCC | CAC | ACG | GAT | GCT | GTA | ATC | CAT | 1875 |
| Trp | Glu | Ala<br>510 | Val | Thr | His | Met | Ala<br>515 | His | Thr | Asp | Ala | Val<br>520 | Ile | His |   |
| GAG | ATT | ATT | GGT | TTT | CTT | GAC | CAG | ACC | TTG | TAC | AGA | TCA | CAA | CAT | 1920 |
| Glu | Ile | Ile<br>525 | Gly | Phe | Leu | Asp | Gln<br>530 | Thr | Leu | Tyr | Arg | Ser<br>535 | Gln | His |   |
| CTT | TGT | GTT | GAA | GCC | TCG | AGA | AAA | CTG | GCC | AGA | GAC | CTC | CTA | AAG | 1965 |
| Leu | Cys | Val<br>540 | Glu | Ala | Ser | Arg | Lys<br>545 | Leu | Ala | Arg | Asp | Leu<br>550 | Leu | Lys |   |
| GAG | CTG | CAA | GCC | CAG | GTC | TAG | CAGGTAGTAC |   | AGAATGTGGG |   |   |   |   |   | 2006 |
| Glu | Leu | Gln<br>555 | Ala | Gln | Val |   |   |   |   |   |   |   |   |   |   |

```
CACCTGCGGT GAAGCTCCCT CAGTGGATGA GATGCTGTTT CTGAGGCAAG AACAAGTGAG   2066
AGTGGTTGAA CATATTCGTG CCTTGGCCTG ATGGAGTGAT GTGTACCACC TCCCACGCTG   2126
TACTGCCTGG CCCCGGCGGT CCATGAGTAT TATGAAGGGA AGGGCCCAGA CTGCCTGTTA   2186
GGTTCCAGCC ATTCATAAGA GCTAGCACTG GCTGGTGTGC TGACTCTCTT TATCCTTCCC   2246
TCTCTAGTGA AGGTGTGGGG GATGCCCAGT AGCAGGAGAC ATGAGCCCTG TAGTGGATGA   2306
GGCTGTACCG TACAGATGAG CACCTGNCTC ACCGGTGACT GTCGCTCAGT GAGGCCTTTG   2366
TTCCTCAGTG CAGAAATGCT GCAAGGCACC ACTATAGTGG AAGGAATGAG AGGTGGCCAG   2426
AGAAGGGTCA TTCCTTCCTC CTCCTCTAAA CCCCCAAAAG GCAAAACACA TCTGCTTCCC   2486
TATGTCTAGT AAACAGGATT TGGAAACTGA GAGTGAGTCC TTGTCCTCCT GCACTTGCTG   2546
TGGGTGGGGA TGACGGGCAT GGCTGTTGTT TTCTAGTGAG AATATATACA AGTGAGCAGT   2606
GTGTGGGCTG TGACCCTCCT GCACATCTGC TATGAGAACC CTTGCCCCAT GTGAAATCAG   2666
CTTCAATTCT CACAGTAGGA CATTTGATGA CTGCACTCAG GCTGTCTAGG GGGGTTGTGG   2726
CATAAAGTCA TGAAGGCCTG GGTTTTCTCT TGCATCTGCA CATCCAGGCT TTGCCGGGCA   2786
AACACTGACT GGCAGTGGAT TCGTCTTTTA CCCACCTGCT GATGGGCTCA CAGTGGAGTG   2846
GAGCTGGACT TTCTACTTTT TCATTCTGAA TAAAAAGTTG TACTTAATTT              2896
```

( 2 ) INFORMATION FOR SEQ ID NO: 32:

( i ) SEQUENCE CHARACTERISTICS:

( A ) LENGTH: 2995 base pairs
( B ) TYPE: Nucleic Acid
( C ) STRANDEDNESS: Double stranded
( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
( A ) ORGANISM: Mouse ( x ) SEQUENCE DESCRIPTION: SEQ ID NO: 32:

```
AATTCCCGCA CGCGCAGTGC ACTCCCTTGC GGCCGCGGGA AAATTCCAAA CACGTCAAAA      60

CAAAAAAGGT TCCGTGAGCT GTGCCAAGTT TTCAAGCCGC AGAAGCCGGG CGGTGGCTTC     120

TTTTCCGCCG CAGCCCAGTC TGCTGAGGCA GCTCTGGGTG AGGACCACCC GGGAAGACCG     180

CCGTTTCCTG CTAGGGCAGA GAAGACTCGC GAGAACGTGC GCCCGAGTCT CAACGTGGGC     240

GAGCCGCGCT CCCGGGGGGT GGAGCTGAGG CAGGACGGCT GCTGTGAAGG GACAGTGCTG     300

CTCTCAGAG  ATG GCT CAG GAG TCT GCA GAC CTT GCT TCT GAC TGT           345
           Met Ala Gln Glu Ser Ala Asp Leu Ala Ser Asp Cys
            1              5                  10

CAG TCT TGG CTG CAG AAG CTT TCT GCA TGG GAA CAG GCC TCT TCT          390
Gln Ser Trp Leu Gln Lys Leu Ser Ala Trp Glu Gln Ala Ser Ser
         15                  20                  25

GAG GAA ACC CAG AAG GAC ACT TGT CTT CAC TTG TCC GGG TTC CAG          435
Glu Glu Thr Gln Lys Asp Thr Cys Leu His Leu Ser Gly Phe Gln
         30                  35                  40

GAG TTC CTG AGG CAG ATG TAT GAA ATC TTG AAG GAG ATG GAT TCT          480
Glu Phe Leu Arg Gln Met Tyr Glu Ile Leu Lys Glu Met Asp Ser
         45                  50                  55

GAT GCA ATC CTG GAA AGG TTC CCC ACA ATT GGT CAA CTG TTG GCA          525
Asp Ala Ile Leu Glu Arg Phe Pro Thr Ile Gly Gln Leu Leu Ala
         60                  65                  70

AAA GCT TGT TGG AAT CCT CTC ATC TTA GCA TAT GAT GAA AGC CAA          570
Lys Ala Cys Trp Asn Pro Leu Ile Leu Ala Tyr Asp Glu Ser Gln
         75                  80                  85

AAA ATT GTA ATA TGG TGC TTA TGT TGT CTG ATG AAC AAA GAA CCT          615
Lys Ile Val Ile Trp Cys Leu Cys Cys Leu Met Asn Lys Glu Pro
         90                  95                 100

CGG ACT TCT GCA GAG TCA GGA CTT AAC TCG TGG ATC CGG GGT TTG          660
Arg Thr Ser Ala Glu Ser Gly Leu Asn Ser Trp Ile Arg Gly Leu
        105                 110                 115

TTA TCT CAT GTA CTT TCT GCA TTC AGA TTC GAC ATG AAA GAA GTT          705
Leu Ser His Val Leu Ser Ala Phe Arg Phe Asp Met Lys Glu Val
        120                 125                 130

TGT CTT TTT ACC AAA AGT CTT GGA TAT GAG TCT ATT GAT TAC TAT          750
Cys Leu Phe Thr Lys Ser Leu Gly Tyr Glu Ser Ile Asp Tyr Tyr
        135                 140                 145

CCT AGT TTG CTT AAA AAT ATG GTT TTG TCA TTA GTG TCT GAG CTC          795
Pro Ser Leu Leu Lys Asn Met Val Leu Ser Leu Val Ser Glu Leu
        150                 155                 160

AGA GAG AGT CAT CTT AAT GGA CTG AGC ACT CAA AGT CGG ATG GCT          840
Arg Glu Ser His Leu Asn Gly Leu Ser Thr Gln Ser Arg Met Ala
        165                 170                 175

CCT GAG CGC ATG ATG TCC CTG TCA GAA GTT TGT GTC CCT CTT GTC          885
Pro Glu Arg Met Met Ser Leu Ser Glu Val Cys Val Pro Leu Val
        180                 185                 190

ACT CTG CCT GAT ATG GAA CCC CTG GTA GAG GCT CTA CTC ACC TAC          930
Thr Leu Pro Asp Met Glu Pro Leu Val Glu Ala Leu Leu Thr Tyr
```

|   |   |   |   |   |   |   |   |   |   |   |   |   |   |   |
|---|---|---|---|---|---|---|---|---|---|---|---|---|---|---|
|   |   | 195 |   |   |   |   | 200 |   |   |   |   | 205 |   |   |
| CAT | GGA | CAT | GAG | CCC | CAG | GAA | GTC | CTG | GCT | CCT | GAG | TTC | TTC | GAA | 975 |
| His | Gly | His<br>210 | Glu | Pro | Gln | Glu | Val<br>215 | Leu | Ala | Pro | Glu | Phe<br>220 | Phe | Glu |
| GCT | GTA | AAT | GAG | GCC | TTC | TTG | TCG | GAA | AAA | ATT | GTT | GTA | CCC | ACG | 1020 |
| Ala | Val | Asn<br>225 | Glu | Ala | Phe | Leu | Ser<br>230 | Glu | Lys | Ile | Val | Val<br>235 | Pro | Thr |
| TCC | TCT | GTG | GTC | AGC | CTC | TGG | TTT | CGG | CAT | CTC | CCC | AGT | CTT | GAA | 1065 |
| Ser | Ser | Val<br>240 | Val | Ser | Leu | Trp | Phe<br>245 | Arg | His | Leu | Pro | Ser<br>250 | Leu | Glu |
| AAA | GCA | ACG | CTG | CAT | CTT | TTT | GAA | AAG | CTT | TTC | TCC | AGC | AAG | ATA | 1110 |
| Lys | Ala | Thr<br>255 | Leu | His | Leu | Phe | Glu<br>260 | Lys | Leu | Phe | Ser | Ser<br>265 | Lys | Ile |
| ATT | TGC | CTG | AGA | AGG | ATG | GAG | TGC | TGT | ATA | AGA | GAG | TCA | TTC | CTG | 1155 |
| Ile | Cys | Leu<br>270 | Arg | Arg | Met | Glu | Cys<br>275 | Cys | Ile | Arg | Glu | Ser<br>280 | Phe | Leu |
| CCT | CAA | GCA | GCC | TGC | CAA | CCT | GCC | ATC | TTC | AGA | ATT | GTT | CAT | GAA | 1200 |
| Pro | Gln | Ala<br>285 | Ala | Cys | Gln | Pro | Ala<br>290 | Ile | Phe | Arg | Ile | Val<br>295 | His | Glu |
| ATG | TTC | AGG | TTT | GTG | CTG | CTG | AAA | ACT | GAC | GGA | GCC | CCA | GAA | GTA | 1245 |
| Met | Phe | Arg<br>300 | Phe | Val | Leu | Leu | Lys<br>305 | Thr | Asp | Gly | Ala | Pro<br>310 | Glu | Val |
| CTA | GCT | GCT | CTT | CAG | GTT | TTC | ACA | TCG | TGC | TTG | GTA | GAA | GCT | CTG | 1290 |
| Leu | Ala | Ala<br>315 | Leu | Gln | Val | Phe | Thr<br>320 | Ser | Cys | Leu | Val | Glu<br>325 | Ala | Leu |
| AAA | AAA | GAA | AAC | AAG | CAG | CTG | ACG | TTT | GCC | CTC | AGG | ACC | TAC | TTT | 1335 |
| Lys | Lys | Glu<br>330 | Asn | Lys | Gln | Leu | Thr<br>335 | Phe | Ala | Leu | Arg | Thr<br>340 | Tyr | Phe |
| CCT | TAC | GGT | GCT | CCA | TGT | CTT | GCT | GCA | GCG | CTG | TCC | CAG | CAC | CCT | 1380 |
| Pro | Tyr | Gly<br>345 | Ala | Pro | Cys | Leu | Ala<br>350 | Ala | Ala | Leu | Ser | Gln<br>355 | His | Pro |
| GAA | GCA | ATC | CCA | CAG | GGA | CAC | CGG | CTC | CAG | CCT | CTG | CTG | CAC | ATT | 1425 |
| Glu | Ala | Ile<br>360 | Pro | Gln | Gly | His | Arg<br>365 | Leu | Gln | Pro | Leu | Leu<br>370 | His | Ile |
| TCC | CAA | CTC | CTC | AGA | GAA | GCA | GTT | GAA | GAC | TGT | ACT | CGT | GGG | TCT | 1470 |
| Ser | Gln | Leu<br>375 | Leu | Arg | Glu | Ala | Val<br>380 | Glu | Asp | Cys | Thr | Arg<br>385 | Gly | Ser |
| CCG | CGA | AAT | CCC | TTT | GAG | AGC | TGG | TTT | TTG | TTT | GTT | CAC | TTT | GGA | 1515 |
| Pro | Arg | Asn<br>390 | Pro | Phe | Glu | Ser | Trp<br>395 | Phe | Leu | Phe | Val | His<br>400 | Phe | Gly |
| GGA | TGG | GTT | GAC | CTG | GCT | GTG | GCA | GAG | TTA | CTG | CTG | AGG | GAG | GAA | 1560 |
| Gly | Trp | Val<br>405 | Asp | Leu | Ala | Val | Ala<br>410 | Glu | Leu | Leu | Leu | Arg<br>415 | Glu | Glu |
| GCT | GAG | CCT | CCT | GCT | GGC | CTG | CTG | TGG | CTC | TTG | GTG | TTC | TAT | TAC | 1605 |
| Ala | Glu | Pro<br>420 | Pro | Ala | Gly | Leu | Leu<br>425 | Trp | Leu | Leu | Val | Phe<br>430 | Tyr | Tyr |
| AGC | CCA | CAG | GAT | GGG | AGT | CAG | CAG | AGA | GAG | CAG | AGC | ATG | GTG | GAG | 1650 |
| Ser | Pro | Gln<br>435 | Asp | Gly | Ser | Gln | Gln<br>440 | Arg | Glu | Gln | Ser | Met<br>445 | Val | Glu |
| CTG | AAG | GTA | TTA | ATC | AAC | CGT | CTC | CTG | ATG | CTG | CTC | AGA | AGC | GGC | 1695 |
| Leu | Lys | Val<br>450 | Leu | Ile | Asn | Arg | Leu<br>455 | Leu | Met | Leu | Leu | Arg<br>460 | Ser | Gly |
| CCC | CTC | TCA | GCT | ACT | GAT | CTG | CAG | GAA | GCA | GCT | GAG | AGT | CCC | AGT | 1740 |
| Pro | Leu | Ser<br>465 | Ala | Thr | Asp | Leu | Gln<br>470 | Glu | Ala | Ala | Glu | Ser<br>475 | Pro | Ser |
| GGA | GAC | CCC | AGA | CCA | CCT | GTA | TGT | GGA | CAG | CTG | GTC | AGA | CGC | CTT | 1785 |
| Gly | Asp | Pro<br>480 | Arg | Pro | Pro | Val | Cys<br>485 | Gly | Gln | Leu | Val | Arg<br>490 | Arg | Leu |
| CTT | CTT | AGT | CTC | TTG | CTC | TGG | ACC | CCA | GAA | GGC | CAT | GCA | ATT | GTC | 1830 |
| Leu | Leu | Ser | Leu | Leu | Leu | Trp | Thr | Pro | Glu | Gly | His | Ala | Ile | Val |

|  |  |  |  |  |  |  |  |  |  |  |  |  |  |  |
|---|---|---|---|---|---|---|---|---|---|---|---|---|---|---|
|  | 495 |  |  |  |  | 500 |  |  |  |  | 505 |  |  |  |
| TGG | GAA | GCT | GTC | ACC | CAT | GGT | CCG | ACT | TTT | GAG | ATC | ACA | GGC | CCA | 1875
| Trp | Glu | Ala | Val | Thr | His | Gly | Pro | Thr | Phe | Glu | Ile | Thr | Gly | Pro |
|  | 510 |  |  |  |  | 515 |  |  |  |  | 520 |  |  |  |
| GGA | TGC | TGC | CCC | AGG | ATA | TGG | AGA | TCC | ACA | AAG | CCA | CAG | CAC | AGA | 1920
| Gly | Cys | Cys | Pro | Arg | Ile | Trp | Arg | Ser | Thr | Lys | Pro | Gln | His | Arg |
|  | 525 |  |  |  |  | 530 |  |  |  |  | 535 |  |  |  |
| CCC | AGA | GCC | CAC | CTG | TGC | TGT | ACA | GAG | ATG | GCC | CAC | ACG | GAT | GCT | 1965
| Pro | Arg | Ala | His | Leu | Cys | Cys | Thr | Glu | Met | Ala | His | Thr | Asp | Ala |
|  | 540 |  |  |  |  | 545 |  |  |  |  | 550 |  |  |  |
| GTA | ATC | CAT | GAG | ATT | ATT | GGT | TTT | CTT | GAC | CAG | ACC | TTG | TAC | AGA | 2010
| Val | Ile | His | Glu | Ile | Ile | Gly | Phe | Leu | Asp | Gln | Thr | Leu | Tyr | Arg |
|  | 555 |  |  |  |  | 560 |  |  |  |  | 565 |  |  |  |
| TCA | CAA | CAT | CTT | TGT | GTT | GAA | GCC | TCG | AGA | AAA | CTG | GCC | AGA | GAC | 2055
| Ser | Gln | His | Leu | Cys | Val | Glu | Ala | Ser | Arg | Lys | Leu | Ala | Arg | Asp |
|  | 570 |  |  |  |  | 575 |  |  |  |  | 580 |  |  |  |
| CTC | CTA | AAG | GAG | CTG | CAA | GCC | CAG | GTC | TAG | CAGGTAGTAC | AGAATGTGGG |  |  |  | 2105
| Leu | Leu | Lys | Glu | Leu | Gln | Ala | Gln | Val |  |  |  |  |  |  |
|  | 585 |  |  |  |  | 590 |  |  |  |  |  |  |  |  |

| | | | | |
|---|---|---|---|---|
| CACCTGCGGT | GAAGCTCCCT | CAGTGGATGA | GATGCTGTTT | CTGAGGCAAG | AACAAGTGAG | 2165
| AGTGGTTGAA | CATATTCGTG | CCTTGGCCTG | ATGGAGTGAT | GTGTACCACC | TCCCACGCTG | 2225
| TACTGCCTGG | CCCCGGCGGT | CCATGAGTAT | TATGAAGGGA | AGGGCCCAGA | CTGCCTGTTA | 2285
| GGTTCCAGCC | ATTCATAAGA | GCTAGCACTG | GCTGGTGTGC | TGACTCTCTT | TATCCTTCCC | 2345
| TCTCTAGTGA | AGGTGTGGGG | GATGCCCAGT | AGCAGGAGAC | ATGAGCCCTG | TAGTGGATGA | 2405
| GGCTGTACCG | TACAGATGAG | CACCTGNCTC | ACCGGTGACT | GTCGCTCAGT | GAGGCCTTTG | 2465
| TTCCTCAGTG | CAGAAATGCT | GCAAGGCACC | ACTATAGTGG | AAGGAATGAG | AGGTGGCCAG | 2525
| AGAAGGGTCA | TTCCTTCCTC | CTCCTCTAAA | CCCCCAAAAG | GCAAAACACA | TCTGCTTCCC | 2585
| TATGTCTAGT | AAACAGGATT | TGGAAACTGA | GAGTGAGTCC | TTGTCCTCCT | GCACTTGCTG | 2645
| TGGGTGGGGA | TGACGGGCAT | GGCTGTTGTT | TTCTAGTGAG | AATATATACA | AGTGAGCAGT | 2705
| GTGTGGGCTG | TGACCCTCCT | GCACATCTGC | TATGAGAACC | CTTGCCCCAT | GTGAAATCAG | 2765
| CTTCAATTCT | CACAGTAGGA | CATTTGATGA | CTGCACTCAG | GCTGTCTAGG | GGGGTTGTGG | 2825
| CATAAAGTCA | TGAAGGCCTG | GGTTTTCTCT | TGCATCTGCA | CATCCAGGCT | TTGCCGGGCA | 2885
| AACACTGACT | GGCAGTGGAT | TCGTCTTTTA | CCCACCTGCT | GATGGGCTCA | CAGTGGAGTG | 2945
| GAGCTGGACT | TTCTACTTTT | TCATTCTGAA | TAAAAAGTTG | TACTTAATTT |  | 2995

( 2 ) INFORMATION FOR SEQ ID NO: 33:

( i ) SEQUENCE CHARACTERISTICS:
        ( A ) LENGTH: 30 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 33:

GAGCCCCCGG AGAGGCGGGA GCGGTGTTGG                                                                                                                 30

( 2 ) INFORMATION FOR SEQ ID NO: 34:

(i) SEQUENCE CHARACTERISTICS:
   (A) LENGTH: 30 base pairs
   (B) TYPE: Nucleic Acid
   (C) STRANDEDNESS: Single stranded
   (D) TOPOLOGY: Linear (ii) MOLECULE TYPE: Genomic DNA (iii) HYPOTHETICAL: No (iv) ANTI-SENSE: No (vi) ORIGINAL SOURCE:
   (A) ORGANISM: Homo sapiens (x) SEQUENCE DESCRIPTION: SEQ ID NO: 34:

AGGTGCAAAC TGAAGTTTTA TTTAGAATGA                    30

(2) INFORMATION FOR SEQ ID NO: 35:

(i) SEQUENCE CHARACTERISTICS:
   (A) LENGTH: 30 base pairs
   (B) TYPE: Nucleic Acid
   (C) STRANDEDNESS: Single stranded
   (D) TOPOLOGY: Linear (ii) MOLECULE TYPE: Genomic DNA (iii) HYPOTHETICAL: No (iv) ANTI-SENSE: No (vi) ORIGINAL SOURCE:
   (A) ORGANISM: Homo sapiens (x) SEQUENCE DESCRIPTION: SEQ ID NO: 35:

ACTGCTGACA CGTGTGCGCG CGCGCGGCTC                    30

(2) INFORMATION FOR SEQ ID NO: 36:

(i) SEQUENCE CHARACTERISTICS:
   (A) LENGTH: 30 base pairs
   (B) TYPE: Nucleic Acid
   (C) STRANDEDNESS: Single stranded
   (D) TOPOLOGY: Linear (ii) MOLECULE TYPE: Genomic DNA (iii) HYPOTHETICAL: No (iv) ANTI-SENSE: No (vi) ORIGINAL SOURCE:
   (A) ORGANISM: Homo sapiens (x) SEQUENCE DESCRIPTION: SEQ ID NO: 36:

CTCTCTAAAT TCTTTAATGG TTCATGACCA                    30

(2) INFORMATION FOR SEQ ID NO: 37:

(i) SEQUENCE CHARACTERISTICS:
   (A) LENGTH: 30 base pairs
   (B) TYPE: Nucleic Acid
   (C) STRANDEDNESS: Single stranded
   (D) TOPOLOGY: Linear (ii) MOLECULE TYPE: Genomic DNA (iii) HYPOTHETICAL: No (iv) ANTI-SENSE: No (vi) ORIGINAL SOURCE:

(A) ORGANISM: Homo sapiens (x) SEQUENCE DESCRIPTION: SEQ ID NO: 37:

ACTGCTGACA CGTGTGCGCG CGCGCGGCTC                                      30

(2) INFORMATION FOR SEQ ID NO: 38:

(i) SEQUENCE CHARACTERISTICS:
  (A) LENGTH: 30 base pairs
  (B) TYPE: Nucleic Acid
  (C) STRANDEDNESS: Single stranded
  (D) TOPOLOGY: Linear (ii) MOLECULE TYPE: Genomic DNA (iii) HYPOTHETICAL: No (iv) ANTI-SENSE: No (vi) ORIGINAL SOURCE:
  (A) ORGANISM: Homo sapiens (x) SEQUENCE DESCRIPTION: SEQ ID NO: 38:

CAAAATGGAC AAAAGCAAGT CTTGACTCAC                                      30

(2) INFORMATION FOR SEQ ID NO: 39:

(i) SEQUENCE CHARACTERISTICS:
  (A) LENGTH: 20 base pairs
  (B) TYPE: Nucleic Acid
  (C) STRANDEDNESS: Single stranded
  (D) TOPOLOGY: Linear (ii) MOLECULE TYPE: Genomic DNA (iii) HYPOTHETICAL: No (iv) ANTI-SENSE: No (vi) ORIGINAL SOURCE:
  (A) ORGANISM: Homo sapiens (x) SEQUENCE DESCRIPTION: SEQ ID NO: 39:

GCATAATGCC TTTACTGACC                                                 20

(2) INFORMATION FOR SEQ ID NO: 40:

(i) SEQUENCE CHARACTERISTICS:
  (A) LENGTH: 19 base pairs
  (B) TYPE: Nucleic Acid
  (C) STRANDEDNESS: Single stranded
  (D) TOPOLOGY: Linear (ii) MOLECULE TYPE: Genomic DNA (iii) HYPOTHETICAL: No (iv) ANTI-SENSE: No (vi) ORIGINAL SOURCE:
  (A) ORGANISM: Homo sapiens (x) SEQUENCE DESCRIPTION: SEQ ID NO: 40:

CACCTACCGC CTTTGAGTG                                                  19

(2) INFORMATION FOR SEQ ID NO: 41:

(i) SEQUENCE CHARACTERISTICS:
  (A) LENGTH: 20 base pairs
  (B) TYPE: Nucleic Acid
  (C) STRANDEDNESS: Single stranded
  (D) TOPOLOGY: Linear (i i) MOLECULE TYPE: Genomic DNA (i i i) HYPOTHETICAL: No (i v) ANTI-SENSE: No (v i) ORIGINAL SOURCE:
    (A) ORGANISM: Homo sapiens (x) SEQUENCE DESCRIPTION: SEQ ID NO: 41:

CAGCCAGAGA CTACCACAAC 20

(2) INFORMATION FOR SEQ ID NO: 42:

(i) SEQUENCE CHARACTERISTICS:
        (A) LENGTH: 20 base pairs
        (B) TYPE: Nucleic Acid
        (C) STRANDEDNESS: Single stranded
        (D) TOPOLOGY: Linear (i i) MOLECULE TYPE: Genomic DNA (i i i) HYPOTHETICAL: No (i v) ANTI-SENSE: No (v i) ORIGINAL SOURCE:
    (A) ORGANISM: Homo sapiens (x) SEQUENCE DESCRIPTION: SEQ ID NO: 42:

CTCTCCACCC GCAGATATCC 20

(2) INFORMATION FOR SEQ ID NO: 43:

(i) SEQUENCE CHARACTERISTICS:
        (A) LENGTH: 21 base pairs
        (B) TYPE: Nucleic Acid
        (C) STRANDEDNESS: Single stranded
        (D) TOPOLOGY: Linear (i i) MOLECULE TYPE: Genomic DNA (i i i) HYPOTHETICAL: No (i v) ANTI-SENSE: No (v i) ORIGINAL SOURCE:
    (A) ORGANISM: Homo sapiens (x) SEQUENCE DESCRIPTION: SEQ ID NO: 43:

GTCCGTCCCT GGACAAAGGA C 21

(2) INFORMATION FOR SEQ ID NO: 44:

(i) SEQUENCE CHARACTERISTICS:
        (A) LENGTH: 20 base pairs
        (B) TYPE: Nucleic Acid
        (C) STRANDEDNESS: Single stranded
        (D) TOPOLOGY: Linear (i i) MOLECULE TYPE: Genomic DNA (i i i) HYPOTHETICAL: No (i v) ANTI-SENSE: No (v i) ORIGINAL SOURCE:
    (A) ORGANISM: Homo sapiens (x) SEQUENCE DESCRIPTION: SEQ ID NO: 44:

ACCATTTCCT TCAGTGCTGG 20

( 2 ) INFORMATION FOR SEQ ID NO: 45:

( i ) SEQUENCE CHARACTERISTICS:
    ( A ) LENGTH: 21 base pairs
    ( B ) TYPE: Nucleic Acid
    ( C ) STRANDEDNESS: Single stranded
    ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
    ( A ) ORGANISM: Homo sapiens ( x ) SEQUENCE DESCRIPTION: SEQ ID NO: 45:

ACCACAAGTC CCGATTCTGG G                    21

( 2 ) INFORMATION FOR SEQ ID NO: 46:

( i ) SEQUENCE CHARACTERISTICS:
    ( A ) LENGTH: 20 base pairs
    ( B ) TYPE: Nucleic Acid
    ( C ) STRANDEDNESS: Single stranded
    ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
    ( A ) ORGANISM: Homo sapiens ( x ) SEQUENCE DESCRIPTION: SEQ ID NO: 46:

CCCTCAATCT ATAATGTCAG                      20

( 2 ) INFORMATION FOR SEQ ID NO: 47:

( i ) SEQUENCE CHARACTERISTICS:
    ( A ) LENGTH: 21 base pairs
    ( B ) TYPE: Nucleic Acid
    ( C ) STRANDEDNESS: Single stranded
    ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
    ( A ) ORGANISM: Homo sapiens ( x ) SEQUENCE DESCRIPTION: SEQ ID NO: 47:

GTAAGCCTCT GTGAAACAAT G                    21

( 2 ) INFORMATION FOR SEQ ID NO: 48:

( i ) SEQUENCE CHARACTERISTICS:
    ( A ) LENGTH: 19 base pairs
    ( B ) TYPE: Nucleic Acid
    ( C ) STRANDEDNESS: Single stranded
    ( D ) TOPOLOGY: Linear ( i i ) MOLECULE TYPE: Genomic DNA ( i i i ) HYPOTHETICAL: No ( i v ) ANTI-SENSE: No (v i) ORIGINAL SOURCE:
    (A) ORGANISM: Homo sapiens (x) SEQUENCE DESCRIPTION: SEQ ID NO: 48:

TAGTAGTTTG AGATTTTCC                                                    19

(2) INFORMATION FOR SEQ ID NO: 49:

(i) SEQUENCE CHARACTERISTICS:
      (A) LENGTH: 19 base pairs
      (B) TYPE: Nucleic Acid
      (C) STRANDEDNESS: Single stranded
      (D) TOPOLOGY: Linear (ii) MOLECULE TYPE: Genomic DNA (iii) HYPOTHETICAL: No (iv) ANTI-SENSE: No (vi) ORIGINAL SOURCE:
      (A) ORGANISM: Homo sapiens (x) SEQUENCE DESCRIPTION: SEQ ID NO: 49:

GCAGCACTTT TAAATAATC                                                    19

(2) INFORMATION FOR SEQ ID NO: 50:

(i) SEQUENCE CHARACTERISTICS:
      (A) LENGTH: 20 base pairs
      (B) TYPE: Nucleic Acid
      (C) STRANDEDNESS: Single stranded
      (D) TOPOLOGY: Linear (ii) MOLECULE TYPE: Genomic DNA (iii) HYPOTHETICAL: No (iv) ANTI-SENSE: No (vi) ORIGINAL SOURCE:
      (A) ORGANISM: Homo sapiens (x) SEQUENCE DESCRIPTION: SEQ ID NO: 50:

GTAGGCATTG TACATAAAAG                                                   20

(2) INFORMATION FOR SEQ ID NO: 51:

(i) SEQUENCE CHARACTERISTICS:
      (A) LENGTH: 20 base pairs
      (B) TYPE: Nucleic Acid
      (C) STRANDEDNESS: Single stranded
      (D) TOPOLOGY: Linear (ii) MOLECULE TYPE: Genomic DNA (iii) HYPOTHETICAL: No (iv) ANTI-SENSE: No (vi) ORIGINAL SOURCE:
      (A) ORGANISM: Homo sapiens (x) SEQUENCE DESCRIPTION: SEQ ID NO: 51:

TGGCACATTC AGCATTAAAC                                                   20

(2) INFORMATION FOR SEQ ID NO: 52:

(i) SEQUENCE CHARACTERISTICS:
      (A) LENGTH: 21 base pairs
      (B) TYPE: Nucleic Acid ( C ) STRANDEDNESS: Single stranded
                ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
                ( A ) ORGANISM: Homo sapiens ( x ) SEQUENCE DESCRIPTION: SEQ ID NO: 52:

CTGATGTAAT CCTGTTTGCA G                     21

( 2 ) INFORMATION FOR SEQ ID NO: 53:

( i ) SEQUENCE CHARACTERISTICS:
                ( A ) LENGTH: 22 base pairs
                ( B ) TYPE: Nucleic Acid
                ( C ) STRANDEDNESS: Single stranded
                ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
                ( A ) ORGANISM: Homo sapiens ( x ) SEQUENCE DESCRIPTION: SEQ ID NO: 53:

CCTCTCATAA CCAAACTGAT AC                    22

( 2 ) INFORMATION FOR SEQ ID NO: 54:

( i ) SEQUENCE CHARACTERISTICS:
                ( A ) LENGTH: 21 base pairs
                ( B ) TYPE: Nucleic Acid
                ( C ) STRANDEDNESS: Single stranded
                ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
                ( A ) ORGANISM: Homo sapiens ( x ) SEQUENCE DESCRIPTION: SEQ ID NO: 54:

GTCCTTAATT ATGCATGGCT C                     21

( 2 ) INFORMATION FOR SEQ ID NO: 55:

( i ) SEQUENCE CHARACTERISTICS:
                ( A ) LENGTH: 22 base pairs
                ( B ) TYPE: Nucleic Acid
                ( C ) STRANDEDNESS: Single stranded
                ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
                ( A ) ORGANISM: Homo sapiens ( x ) SEQUENCE DESCRIPTION: SEQ ID NO: 55:

CAACACACCA CAGCCTTCTA AG                                                                                       22

( 2 ) INFORMATION FOR SEQ ID NO: 56:

( i ) SEQUENCE CHARACTERISTICS:
        ( A ) LENGTH: 20 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 56:

TTTTCAGTGA GCCATTTCTG                                                                                           20

( 2 ) INFORMATION FOR SEQ ID NO: 57:

( i ) SEQUENCE CHARACTERISTICS:
        ( A ) LENGTH: 20 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 57:

AAATGAGTCC AAGCATGTCC                                                                                           20

( 2 ) INFORMATION FOR SEQ ID NO: 58:

( i ) SEQUENCE CHARACTERISTICS:
        ( A ) LENGTH: 20 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 58:

CTCCTTTGGC TGATAATAGC                                                                                           20

( 2 ) INFORMATION FOR SEQ ID NO: 59:

( i ) SEQUENCE CHARACTERISTICS:
        ( A ) LENGTH: 20 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
    ( A ) ORGANISM: Homo sapiens ( x ) SEQUENCE DESCRIPTION: SEQ ID NO: 59:

CCCATGATAC AGCCAGAGAC    20

( 2 ) INFORMATION FOR SEQ ID NO: 60:

( i ) SEQUENCE CHARACTERISTICS:
        ( A ) LENGTH: 20 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 60:

TTTCCCTTAT ACAGTGCAGG    20

( 2 ) INFORMATION FOR SEQ ID NO: 61:

( i ) SEQUENCE CHARACTERISTICS:
        ( A ) LENGTH: 21 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 61:

GTGCTCTTGT CCAAAATACT C    21

( 2 ) INFORMATION FOR SEQ ID NO: 62:

( i ) SEQUENCE CHARACTERISTICS:
        ( A ) LENGTH: 20 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 62:

TTCCTGACCC CGTTTCAATC    20

( 2 ) INFORMATION FOR SEQ ID NO: 63:

( i ) SEQUENCE CHARACTERISTICS:

( A ) LENGTH: 20 base pairs
( B ) TYPE: Nucleic Acid
( C ) STRANDEDNESS: Single stranded
( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
( A ) ORGANISM: Homo sapiens ( x ) SEQUENCE DESCRIPTION: SEQ ID NO: 63:

TTGACAATGC TCTTCCCAGG 20

( 2 ) INFORMATION FOR SEQ ID NO: 64:

( i ) SEQUENCE CHARACTERISTICS:
( A ) LENGTH: 20 base pairs
( B ) TYPE: Nucleic Acid
( C ) STRANDEDNESS: Single stranded
( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
( A ) ORGANISM: Homo sapiens ( x ) SEQUENCE DESCRIPTION: SEQ ID NO: 64:

GTGAACCAGA AGTAAAGGGC 20

( 2 ) INFORMATION FOR SEQ ID NO: 65:

( i ) SEQUENCE CHARACTERISTICS:
( A ) LENGTH: 19 base pairs
( B ) TYPE: Nucleic Acid
( C ) STRANDEDNESS: Single stranded
( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
( A ) ORGANISM: Homo sapiens ( x ) SEQUENCE DESCRIPTION: SEQ ID NO: 65:

AGGATCTAGG GAAACCATG 19

( 2 ) INFORMATION FOR SEQ ID NO: 66:

( i ) SEQUENCE CHARACTERISTICS:
( A ) LENGTH: 21 base pairs
( B ) TYPE: Nucleic Acid
( C ) STRANDEDNESS: Single stranded
( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
( A ) ORGANISM: Homo sapiens ( x ) SEQUENCE DESCRIPTION: SEQ ID NO: 66:

CCCAAAGGAA GAAGAATTTA G  21

( 2 ) INFORMATION FOR SEQ ID NO: 67:

( i ) SEQUENCE CHARACTERISTICS:
        ( A ) LENGTH: 20 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 67:

CCTCTCCTTG CTCCTCTCAG  20

( 2 ) INFORMATION FOR SEQ ID NO: 68:

( i ) SEQUENCE CHARACTERISTICS:
        ( A ) LENGTH: 21 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 68:

CCTAGAAGTA TGTCTGTCCT G  21

( 2 ) INFORMATION FOR SEQ ID NO: 69:

( i ) SEQUENCE CHARACTERISTICS:
        ( A ) LENGTH: 21 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 69:

CTCTCCTTGA CTAGGATGCT G  21

( 2 ) INFORMATION FOR SEQ ID NO: 70:

( i ) SEQUENCE CHARACTERISTICS:
        ( A ) LENGTH: 20 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA (  i i i  ) HYPOTHETICAL: No (  i v  ) ANTI-SENSE: No (  v i  ) ORIGINAL SOURCE:
    ( A ) ORGANISM: Homo sapiens ( x ) SEQUENCE DESCRIPTION: SEQ ID NO: 70:

GGATAGGGCT TCTTTCAGGG                        20

( 2 ) INFORMATION FOR SEQ ID NO: 71:

( i ) SEQUENCE CHARACTERISTICS:
        ( A ) LENGTH: 20 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 71:

TCCCAAGATG TGTACAGCTC                        20

( 2 ) INFORMATION FOR SEQ ID NO: 72:

( i ) SEQUENCE CHARACTERISTICS:
        ( A ) LENGTH: 18 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 72:

TACTAGCTGC TCTTCAGG                          18

( 2 ) INFORMATION FOR SEQ ID NO: 73:

( i ) SEQUENCE CHARACTERISTICS:
        ( A ) LENGTH: 18 base pairs
        ( B ) TYPE: Nucleic Acid
        ( C ) STRANDEDNESS: Single stranded
        ( D ) TOPOLOGY: Linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Homo sapiens ( x ) SEQUENCE DESCRIPTION: SEQ ID NO: 73:

AGCATCAGGA GACGGTTG                          18

FANCONI ANEMIA TYPE C GENE

This application is a continuation of U.S. patent application Ser. No. 08/003,963, filed Jan. 15, 1993, now abandoned, which is a continuation-in-part of U.S. patent applicaton Ser. No. 07/918,313, filed Jul. 21, 1992, now abandoned which is a continuation-in-part of U.S. patent application Ser. No. 07/876,285, filed Apr. 29, 1992 now abandoned.

FIELD OF THE INVENTION

The present invention relates generally to a gene associated with the human Fanconi Anemia (FA) disease process, and, more particularly, to the identification, isolation and cloning of this gene. The present invention also identifies the murine homolog of the human cDNA sequence corresponding to this gene. The present invention also relates to methods of screening for and detection of FA carriers, FA diagnosis, prenatal FA screening and diagnosis, and gene therapy utilizing recombinant DNA technologies.

BACKGROUND OF THE INVENTION

Fanconi Anemia (FA) is a rare and usually fatal human disorder of DNA repair characterized by progressive bone marrow failure, increased risk of malignancy and multiple congenital abnormalities mostly associated with developmental hypoplasia. It affects approximately one in 300,000 individuals (Swift, 1971).

The disorder may be associated with a variety of overt congenital somatic anomalies, such as hypoplasia or other malformations of the kidney, cutaneous hyperpigmentation, and bony abnormalities, particularly hypoplastic or absent thumbs and radii (Glanz and Fraser, 1982). However, these clinical manifestations of FA are extremely variable, both in type and severity, and so diagnosis of the disease on this basis alone is difficult and unreliable.

Affected individuals also show a range of gross hematological and immunological abnormalities: progressive pancytopenia with bone marrow hypoplasia (aplastic anemia), raised fetal hemoglobin and lymphopenia accompanied by defective mitogenic response to phytohaemagglutinin, and low natural killer cell function. Cells from FA patients exhibit a high level of spontaneous chromosomal aberrations when compared to cells of unaffected individuals. This cellular FA phenotype is even more apparent when DNA cross-linking agents such as mitomycin C (MMC) or diepoxybutane (DEB) are used to induce chromosome damage. Tests for prenatal and postnatal diagnoses of Fanconi Anemia have been developed based upon these cellular FA phenotypes. Schroeder et al. (1964, 1976) first suggested the use of spontaneous chromosomal breakage as a cellular marker for FA; however, longitudinal studies of chromosome instability in FA patients have shown a wide variation in the frequency of baseline breakage within the same individual, ranging from no baseline breakage to high levels (Schroeder et al., 1976; McIntosh et al., 1979). However, chromosome breakage in response to DNA cross-linking agents has been found to be a more reliable indicator of FA. Tests based on demonstrating an increased frequency of induced chromosomal breakage after exposure of cultured cells to a variety of DNA cross-linking agents such as MMC are in use in some laboratories (Berger et al., 1980; Cervenka et al., 1981), as are tests based on the differential inhibition of cell growth when FA and normal lymphocytes are cultured in a medium containing MMC (Arwert and Kwee, 1989). Prenatal and postnatal diagnoses of FA are also made based upon an analysis of DEB-induced chromosomal breakage as described by Auerbach et al. (1989a). This DEB hypersensitivity is now a widely accepted criterion in the diagnosis of FA.

The finding of a positive diagnosis of FA is critically important in determining an appropriate treatment regime. Data from the International Fanconi Anemia Registry (IFAR) show that at least 25% of FA patients have no congenital malformations (Auerbach et al., 1989b). Thus, individuals with aplastic anemia or leukemia but with no overt clinical manifestations of FA may be FA suffers. Bone marrow transplantation is frequently used to treat aplastic anemia and, as part of this treatment, cyclophosphamide (a neoplastic suppressant) may be administered; FA patients are hypersensitive to this agent because of their susceptibility to DNA cross-linking agents, and so routine administration of cyclophosphamide to FA patients may be dangerous. Similarly, FA patients are hypersensitive to the chemotherapeutic agents that may be employed in treating leukemia. It has therefore been suggested that all young patients with aplastic anemia or leukemia of unknown etiology should be tested for sensitivity to DEB in order to rule out a diagnosis of FA (Auerbach et al., 1989a).

Studies have shown that FA is a recessive autosomal disorder. That is, it is an inherited disease which results from the presence of a mutated gene in both parents. Briefly put, a gene which, when mutated, gives rise to FA in an individual may be referred to as an FA gene. Human cells are diploid, meaning that each cell has two copies of each chromosome and therefore two copies of each gene including each FA gene, one contributed from each parent. The recessive nature of the FA disorder means that both copies of a particular FA gene must be mutated in order for an individual to exhibit symptoms. Thus, it is assumed that FA sufferers carry one (or more) mutation(s) in both copies of a particular FA gene. A non-mutated, normal version of this gene encodes a protein that plays a role in a particular biochemical pathway of the cell. The normal protein is therefore required for overall normal cell function. The mutated FA gene encodes either a defective protein or no protein at all, and so the specific biochemical pathway for which the portion is required is changed, and thereby normal cell function is disrupted. Individuals who have one copy of an FA gene which is "normal" and one copy which is mutated do not exhibit FA symptoms but rather, are FA carriers. FA carriers may also be described as FA heterozygotes. It is thus proposed that FA heterozygotes do not manifest clinical FA symptoms because they have one normal copy and one mutant copy of a particular FA gene, and that the protein produced by the one normal gene is sufficient for normal cell function (or at least sufficiently normal cell function so that no overt clinical abnormalities are presented). The offspring of two FA carriers who carry mutations in the same FA gene have a 25 percent chance of inheriting the FA disease and a 50 percent chance of being FA carriers themselves.

Parental heterozygotes of FA patients are superficially normal in appearance and lack overt laboratory abnormalities. Various attempts have been made to correlate FA heterozygote status to definite clinical symptoms and also to provide a direct laboratory test for heterozygosity. A reliable test for FA carrier status (FA heterozygotes) would be of great benefit for genetic counseling generally and most particularly for families with a history of Fanconi Anemia. A reliable test for heterozygotes would also greatly aid the development of treatment regimes for FA sufferers. Left to follow its natural course, FA is always fatal, with death caused by progressive marrow aplasia or, less frequently, by development of acute leukemia.

Bone marrow transplantation (BMT) has the potential to correct the stem cell defect and offers a reasonable chance of cure if a tissue-matched healthy donor can be located. It is mandatory to assess potential donors with respect to their FA status. The determination that a potential donor is an FA heterozygote may direct against the selection of tissues from this donor if alternative donors are available. Tissue-matched donors are most likely to be found among close family members of the patient, and there is clearly an increased risk that potential donors who are family members will be either FA sufferers or FA heterozygotes.

Auerbach and Wolman (1978) proposed the use of the DEB test to detect heterozygotes. However, as described by Dallapiccola and Porfirio (1989), the DEB-induced chromosomal breakage rate has been shown to be similar in FA heterozygotes and normal individuals, severely limiting the use of this test. Berger et al. (1980) have proposed the use of Sister Chromatid Exchange Analysis (SCE) in conjunction with exposure to nitrogen mustard gas, although the reliability of this test has also been questioned (Dallapiccola and Porfirio, 1989). Petridou and Barrett (1990) have suggested that FA heterozygotes show minor physical and hematological abnormalities perhaps consistent with partial expression of an FA gene in the heterozygote. However, the subtlety and inherent variation of these "symptoms" may make a clinically reliable diagnosis of FA heterozygosity based on these abnormalities difficult.

As the foregoing description illustrates, it has not been possible to satisfactorily identify heterozygote carriers of the FA gene either at the clinical level or through direct laboratory tests. There is a widely recognized need for such a test, which has been articulated by researchers in this area. Dallapiccola and Porfirio (1989), for example, remarked that:

In the last decade, efforts to develop in vitro tests for the identification of FA heterozygotes have not been successful. No study has provided accurate and reliable tests with obligate heterozygotes. Even the DEB test— which gives reproducible results in the diagnosis of FA homozygotes and also shows a rather distinct clastogenic effect in a proportion of heterozygotes—does not meet widely accepted criteria for a screening test in the population. The other laboratory tests, which are also based upon the presumed ability of different chemicals to induce differential yields of breaks and/or in FA heterozygotes and controls, provide even less satisfactory results. There is an urgent need to improve laboratory tests for the study of FA heterozygotes.

Intensive research has been in progress to find a suitable laboratory test to fill the need.

Although the heritable characteristics of the disease are recognized, the exact underlying basis for FA is unknown. Genes responsible for the disease have not been characterized to date, and it has been difficult to identify a specific biochemical defect responsible for the physical and cellular features of FA. The determination of the exact underlying defect in FA is complicated by the widely varying symptoms of the disease. Two hypotheses have been proposed for the possible biochemical defect based upon the observation of increased sensitivity to DNA cross-linking agents of FA cells. The first proposes that FA cells cannot repair damaged DNA because the defective protein is directly involved in recognizing, modifying or repairing cross links. The alternative hypothesis is that the cell is unable to respond to the oxidative stress caused by DNA cross-linking agents because of a defect in one of the detoxification mechanisms that remove free radicals or oxygen byproducts. It is possible that mutations in several genes may give rise to what is clinically described as FA, and that both of the hypotheses above may hold true. The issue may only be resolved following the cloning and characterization of FA genes.

The determination that mutations in multiple genes may give rise to a particular disease (also known as locus heterogeneity) has been made in other DNA repair disorders, notably, xeroderma pigmentosum (XP) (Vermeulen et al., 1991) and ataxia telangiectasia (AT) (Jaspers et al., 1988). Research has also been directed toward determining the number of genes which, when mutated, can give rise to FA. Duckworth-Rysiecki et al. (1985) utilized somatic cell hybridization studies to assess the number of potential FA genes. In this work, the ability of one FA cell line to complement an FA mutation present in a second cell line was assessed. Briefly put, assuming multiple FA genes, if a first FA cell line is homozygous for a mutation in FA gene #1, it will produce a corresponding defective FA protein #1 and be unable to perform the biochemical function normally provided by FA protein #1. Similarly, if a second FA cell line is homozygous for a mutation in FA gene #2, it will produce a corresponding defective FA protein #2 and be unable to perform the biochemical function normally provided by FA protein #2. Both of these cell lines will therefore exhibit sensitivity to DNA cross-linking agents characteristic of FA cell lines.

When these two cell lines are then fused together (a process known as somatic cell hybridization), the resulting somatic cell hybrid will contain functional FA protein #1 (from FA cell line #2) and functional FA protein #2 (from FA cell line #1). This somatic hybrid will therefore be able to perform both biochemical functions and will exhibit the characteristics of normal cells rather than the characteristics of FA cells. Thus, FA gene #1 and FA gene #2 are said to "complement" each other and to belong to different "complementation groups." Duckworth-Rysiecki et al. (1985) fused lymphoblast cell lines derived from different FA patients together to create such somatic cell hybrids. These somatic cell hybrids were then examined for their sensitivity to DNA cross-linking agents. It was found that when lymphocytes from certain FA patients were fused together, the resulting somatic cell hybrids exhibited a sensitivity to DNA cross-linking agents similar to that of "normal" cells.

The explanation proposed for this observation was that the FA defects in the cell lines which when fused gave this result were at different, complementing genetic loci. One interpretation of this result is that at least two different genes, when mutated, can give rise to FA. However, the possibility of intragenic complementation has not been ruled out. The two complementation groups were designated FA(A) and non-FA(A) with respect to the ability to complement the FA phenotype of a standard FA(A) cell line (Duckworth-Rysiecki et al., 1985).

These two complementation groups have been suggested to correspond to phenotypically different classes of cells exhibiting different rates of recovery of semi-conservative DNA synthesis after treatment with DNA cross-linking agents in culture (Moustacchi et al., 1987) and different rates of removal of DNA cross-links as shown by electron microscopy (Rousset et al., 1990). However, these biochemical assays do not provide a reliable method for determining the complementation group of a given patient, nor is there any apparent correlation between clinical phenotype and genetic class.

A number of genes in both prokaryotes and eukaryotes have been cloned following the identification of the specific gene product. In FA, in common with several other human genetic diseases, the lack of an identified gene product prevents cloning of the gene through this approach. Recently, human genetic disease genes have been cloned using a positional cloning strategy. Examples of genes cloned by this method include genes underlying Cystic Fibrosis (CF), as described in International Patent Application No. WO 91/10734, and Neurofibromatosis (NF), as described in International Patent Application No. WO 92/00387. The cloning of human genetic disease genes such as these facilitates identification of the gene products and the underlying biochemical defects of the disease. Moreover, through interaction with a defective product and the pathway in which this gene product is involved, therapy through normal gene product supplementation and gene manipulation and delivery are now made possible. The cloning of genes underlying FA could make such gene therapy for FA sufferers feasible. Gene therapy for FA might, for example, involve the introduction of functional FA genes into bone marrow cells removed from the patient followed by the reintroduction into the patient.

The positional cloning approach successfully utilized for CF and NF requires that the genetic location of a gene on the human genome be determined by genetic linkage analysis. Extensive locus heterogeneity complicates the use of this approach to identify genes (Tsui and Estevill, 1991); the finding of at least two complementation groups for FA may prevent the successful utilization of this method for cloning FA genes. Mann et al. (1991) have reported localization of one FA gene to chromosome 20q by linkage analysis. Significant LOD scores (Log of the ODds, a measure of the likelihood of the gene placement being correct) were obtained only under the assumption of locus heterogeneity, although the families used were not classified as to complementation group. Further use of this method requires subdividing the family collection, leading to much smaller sets and increasing the difficulty in performing linkage analysis. To date, no progress has been reported in cloning genes underlying FA through a positional cloning approach.

In addition to somatic cell hybrid complementation studies, a number of reports have demonstrated that the characteristic DNA cross-linking agent sensitivity exhibited by FA cells may be complemented by the introduction of DNA or cell extracts from normal cells. These reports raise the possibility that FA genes could be identified by their ability to complement the FA characteristic in FA cell lines. In this way, a gene which is able to complement the characteristic ultra violet light sensitivity of cells from xeroderma pigmentosum (XP) patients has been cloned (Tanaka et al., 1989). Tanaka et al. (1989) transfected mouse genomic DNA into a human XP cell line. Following two rounds of selection for complementation, mouse DNA was extracted from the complemented human XP cells, and a gene responsible for complementation was identified.

Approaches similar to this have been attempted in efforts to clone genes underlying FA; however, these attempts have been uniformly unsuccessful. Several factors may contribute to the difficulty of isolating FA genes by this method. Among these, the low competence of human cell lines for DNA transfection and the high spontaneous reversion frequency (for MMC sensitivity) of SV40-transformed cell lines selected for higher transfection efficiencies (Buchwald et al., 1987) have been recognized. An additional problem may be that FA genes could simply be too large to clone by such genomic DNA transfection methods. Human genes (for instance, the gene underlying CF) may span many tens or hundreds of kilobases of DNA. Large genomic fragments carrying entire genes may therefore be absent from genomic libraries where the average insert size is much smaller than the size of the target gene.

To date, then, despite significant research efforts, the actual biochemical defect which causes FA has not been determined. Efforts to clone genes underlying the disease have also been unsuccessful. It is therefore an object of this invention to provide a novel method for isolating FA genes.

It is a further object of this invention to identify a DNA sequence derived from normal human cells which complements the FA defect in specific FA cell lines, and thereby to provide a human gene sequence which, when mutated, leads to the development of FA.

Based upon this gene sequence, it is a further object of this invention to provide improved methods for diagnosing FA and determining FA heterozygote status.

It is also an object of this invention to enable the production of an animal model for FA. A further object of this invention is to enable human gene therapy methods for FA.

SUMMARY OF THE INVENTION

The foregoing objects have been achieved by providing an isolated human cDNA molecule which is able specifically to correct the cellular defect characteristic of one particular type of Fanconi Anemia. Evidence is provided that the gene from which this cDNA molecule is derived is an FA gene. This genomic FA gene (from which the cDNA molecule is derived) is also provided by the present invention, as is the mouse homolog of the human cDNA molecule.

The inventors have determined that the non(A) Fanconi Anemia complementation group comprises at least three previously unrecognized complementation groups, herein named B, C and D. Thus FA is now subdivided, by complementation groups into FA(A), FA(B), FA(C) and FA(D). This finding indicates that at least four genes, when mutated, may give rise to FA.

Specifically, the invention provides, for the first time, three isolated DNA molecules which, when transfected into cells derived from a patient with FA of complementation group C are able to complement the hypersensitivity to DNA cross-linking agents exhibited by these cells. The DNA molecules are cDNA molecules derived from healthy (non-FA) human cells.

Also provided by the present invention are the nucleotide sequences of these molecules. Analysis of these sequences shows that the three cDNA molecules isolated are cellular variants of a single cDNA transcribed from the same gene. The three cDNAs are herein named collectively as the Fanconi Anemia Group C Complementing cDNA, or FACC cDNA. The three cDNA molecules each contain an identical open reading frame encoding a protein that is herein named the FACC protein. The amino acid sequence of the FACC protein is derived by theoretical translation of the FACC cDNA coding region and is another aspect of this invention.

Having herein provided the nucleotide sequence of the FACC cDNA, correspondingly provided are the complementary DNA strands of the cDNA molecule and DNA molecules which hybridize under stringent conditions to the FACC cDNA molecule or its complementary strand. Such hybridizing molecules include DNA molecules differing only by minor sequence changes, including nucleotide substitutions, deletions and additions. Also comprehended by this invention are isolated oligonucleotides comprising at least a segment of the cDNA molecule or its complementary strand, such as oligonucleotides which may be employed as effective DNA hybridization probes or primers useful in the polymerase chain reaction. Hybridizing DNA molecules and variants on the FACC cDNA may readily be created by standard molecular biology techniques.

Hybridization techniques also allow the cloning of homologous DNA sequences from other species. The present invention provides the nucleotide sequence of the murine homolog of the human FACC cDNA. This mouse cDNA which is herein referred to as the Facc cDNA encodes a protein (referred to as the Facc protein) that shares 79 percent amino acid sequence similarity with the human gene product. Furthermore, the expression of the mouse cDNA in human FA(C) cells lowers the cellular drug sensitivity to normal levels. Thus, the function of this protein has been conserved despite the significant sequence divergence. The cloning of the mouse Facc cDNA should facilitate the development of a mouse model for Fanconi anemia which may be used to develop and test strategies for clinical intervention and to investigate the possibility of gene replacement therapy in the bone marrow. A Fanconi anemia mouse will also facilitate the study of the affects of epigenetic factors in the development of Fanconi anemia and the investigation of the abnormal developmental processes that occur in the absence of the FACC/Facc protein.

Through the manipulation of the nucleotide sequence of the human or murine cDNAs provided by this invention by standard molecular biology techniques, variants of the FACC and Facc proteins may be made which differ in precise amino acid sequence from the disclosed proteins yet which maintain the essential characteristics of the FACC and Facc proteins or which are selected to differ in some characteristics from these proteins. Such variants are another aspect of the present invention.

Also provided by the present invention are recombinant DNA vectors comprising the disclosed DNA molecules, and transgenic host cells containing such recombinant vectors.

Having provided the isolated human FACC cDNA sequence and the mouse homolog of this sequence, also comprehended by this invention are the genomic genes from which these cDNAs are derived. The present invention also provides a yeast artificial chromosome clone containing the human genomic gene from which the FACC cDNA is derived. The genomic gene is termed the FA(C) gene. The exon structure of this gene is provided and the nucleotide sequences of the exon regions immediately flanking intron/exon boundaries are given. Cloning of the mouse genomic FA(C) gene homolog is made possible by the mouse Facc cDNA sequence information provided by this invention in conjunction with standard molecular biology procedures.

Having provided the isolated human FACC cDNA and FA(C) gene and the murine Facc cDNA and FA(C) gene and the purified proteins encoded by these genes, the present invention also provides for the use of the cDNAs, the genomic genes and derivatives thereof, and of the proteins, and derivatives thereof, in aspects of diagnosis and treatment of FA(C).

An embodiment of the present invention is a method for screening a subject to determine if said subject carries a mutant FA(C) gene. The method comprises the steps of: providing a biological sample obtained from the subject, which sample includes DNA or RNA, and providing an assay for detecting in the biological sample the presence of at least one member from the group consisting of a mutant FA(C) gene and a mutant FA(C) RNA. A preferred embodiment of this method is described wherein the assay comprises a method selected from the group consisting of: hybridization with oligonucleotides; PCR amplification of the FA(C) gene or a part thereof using oligonucleotide primers; RT-PCR amplification of the FA(C) RNA or a part thereof using oligonucleotide primers, and direct sequencing of the FA(C) gene of the subject's genome using oligonucleotide primers. When the availability of intron sequence data from the splice sites of the human FA(C) gene and polymerase chain reactions for the amplification of these sequences from genomic DNA, as provided by this invention, will permit the analysis of these regions for potential splice site mutations. Furthermore, the efficiency of these molecular genetic methods should permit a more rapid classification of FA patients than is possible with the labor intensive method of classical complementation analysis.

A further aspect of the present invention is a method for screening a subject to assay for the presence of a mutant FA(C) gene comprising the steps of: providing a biological sample of the subject which sample contains cellular proteins and providing an immunoassay for quantitating the level of FACC protein in the biological sample.

Another aspect to the present invention is an antibody preparation comprising antibodies that specifically detect the FACC protein, wherein the antibodies are selected from the group consisting of monoclonal antibodies and polyclonal antibodies.

Those skilled in the art will appreciate the utility of this invention which is not limited to the specific experimental modes and materials described herein.

The foregoing and other features and advantages of the invention will become more apparent from the following detailed description and accompanying drawings.

BRIEF DESCRIPTION OF DRAWINGS

FIG. 6 shows the nucleotide sequences of several disclosed FACC cDNA molecules and a corresponding translation product.

FIG. 11 shows the nucleotide sequence and protein translation of the mouse Facc gene from the clone pmfac2.

FIG. 12 shows the nucelotide sequence and protein translation of the mouse Facc gene with the sequence of the additional exon from pmfac7 inserted at the arrowhead.

FIG. 13 shows a comparison of the 5' UTR of clone pmfac2 (mouse) and the human FACC cDNA, showing exon 1 of the human gene. The arrowheads mark the first bases of exon 2 and the start of the coding region, also indicated by the initating methonine in both sequences.

FIG. 14 shows a sequence comparision of the human FACC and mouse Facc cDNA open reading frames. Matches between the sequences are marked by a bar, with conserved amino acids marked with two dots.

SEQUENCE LISTING

The nucleotide sequences of 3 disclosed human FACC cDNA molecules and their corresponding translation product are presented in Seq. I.D. Nos. 1–3 of the Sequence Listing. Seq. I.D. No. 4 shows the human amino acid sequence of the FACC protein. Seq. I.D. Nos. 5–31 show partial nucleotide sequences of the introns from the human genomic FA(C) gene. Seq. I.D. Nos. 32–37 show primers suitable for amplifying cDNA molecules corresponding to clones pFAC3 (Seq. I.D. Nos. 33 and 34), pPAC4 (Seq. I.D. Nos. 35 and 36), and pFAC8 (Seq. I.D. Nos. 37 and 38). Seq. I.D. Nos. 39–43 show primer sequences used to amplify introns as noted in Table 6. Seq. I.D. Nos. 44–71 show the primer sequences used to amplify the coding exons from the FA(C) gene set forth in Table 9. Seq. I.D. Nos. 72 and 73 set forth primer sequences RAC9 and RAC16.

Definitions

In order to facilitate review of the various embodiments of the invention and an understanding of various embodiments and constituents used in making the invention, the following definition of terms is provided:

BMT: bone marrow transplantation.

Figure 1:
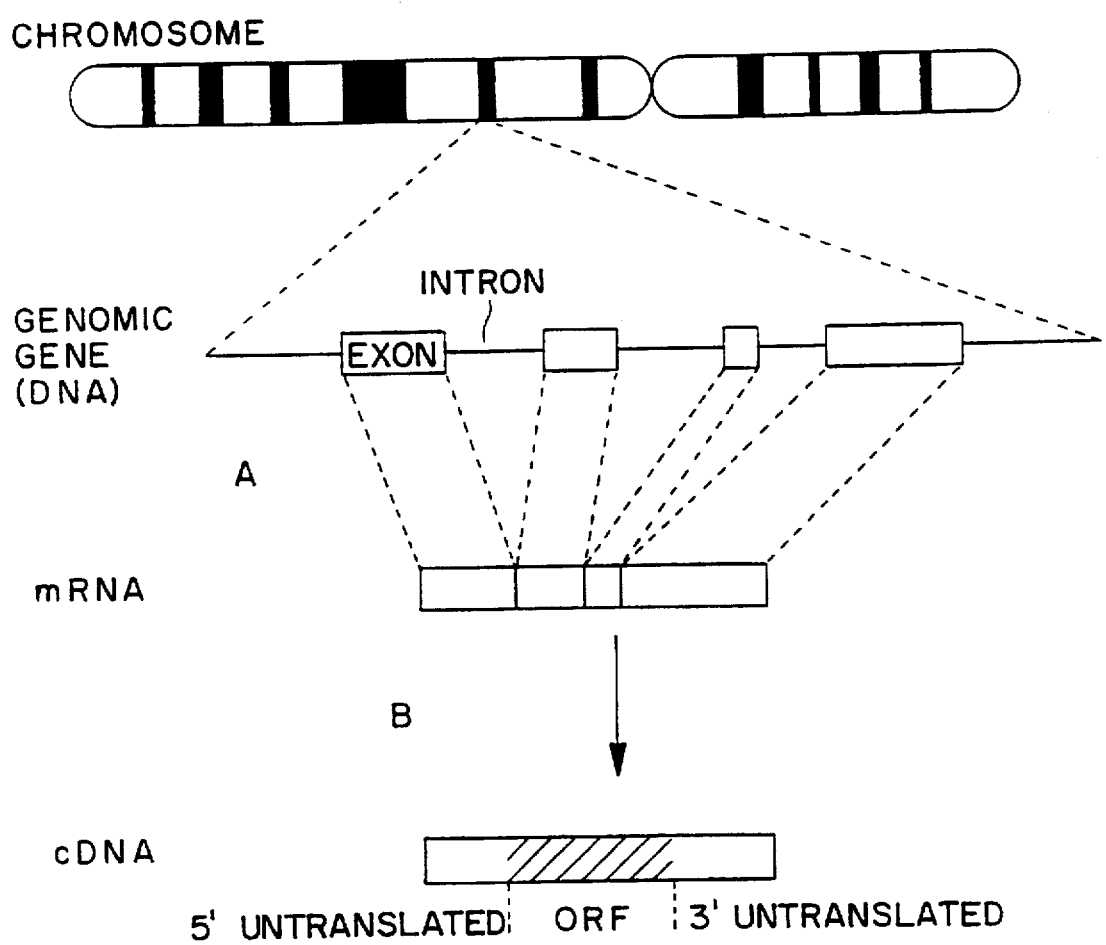
FIG. 1 is a schematic diagram illustrating the progression from chromosome to gene to mRNA to cDNA.

DNA: deoxyribonucleic acid. DNA is a long chain polymer which comprises the genetic material of most living organisms (some viruses have genes comprising ribonucleic acid [RNA]). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed. The nomenclature for DNA bases as set forth at 37 CFR § 1.822 is used.

cDNA (complementary DNA): a piece of DNA lacking internal, non-coding segments (introns) and regulatory sequences which determine transcription. cDNA is synthesized in the laboratory by reverse transcription from messenger RNA extracted from cells. The transcription of a genomic gene into messenger RNA and the processing thereof is illustrated in FIG. 1. Also illustrated in FIG. 1 is the derivation of a cDNA from mRNA.

FA: Fanconi Anemia.

FA carrier or FA heterozygote: a person who does not exhibit apparent signs and symptoms of FA but whose chromosomes contain a mutant FA gene that may be transmitted to that person's offspring.

FA gene: a gene, the mutant forms of which are associated with the disease Fanconi Anemia. This definition is understood to include the various sequence polymorphisms that exist, wherein nucleotide substitutions in the gene sequence do not affect the essential functions of the gene product. This term relates primarily to an isolated coding sequence, but can also include some or all of the flanking regulatory elements and/or intron sequences. The mouse homolog of this gene is referred to as the murine FA(C) gene.

FA patient: a person who carries a mutant FA gene on each chromosome, such that the person exhibits clinical signs and/or symptoms of FA.

FA(C): Fanconi Anemia of complementation group C.

FA(C) carrier or FA(C) heterozygote: a person who does not exhibit signs or symptoms of FA but whose chromosomes contain a mutant FA(C) gene that may be transmitted to that person's offspring.

FA(C) gene: the gene, present in the human genome, mutant forms of which are associated with Fanconi Anemia of complementation group C. This definition is understood to include the various sequence polymorphisms that exist, wherein nucelotide substitutions in the gene sequence do not affect the essential functions of the gene product. This term relates primarily to an isolated coding sequence, but can also include some or all of the flanking regulatory elements and/or intron sequences. The mouse homolog of this gene is referred to as the murine FA(C) gene.

FA(C) patient: a person who carries a mutant FA(C) gene on each chromosome, such that the person exhibits clinical symptoms of FA(C).

FACC cDNA: a human cDNA molecule which, when transfected into FA(C) cells, is able to complement the hypersensitivity of those cells to DNA crosslinking agents. The FACC cDNA is derived by reverse transcription from the mRNA encoded by the FA(C) gene and lacks internal non-coding segments and transcription regulatory sequences present in the FA(C) gene.

Facc cDNA: the mouse homolog of the human FACC cDNA.

FACC protein: the protein encoded by the human FACC cDNA. This definition is understood to include the various sequence polymorphisms that exist, wherein amino acid substitutions in the protein sequence do not affect the essential functions of the protein.

Facc protein: the protein encoded by the mouse Facc cDNA. This definition is understood to include the various sequence polymorphisms that exist, wherein amino acid substitutions in the protein sequence do not affect the essential functions of the protein.

Isolated: requires that the material be removed from its original environment. For example, a naturally occurring DNA molecule present in a living animal is not isolated, but the same DNA molecule, separated from some or all of the coexisting materials in the natural system, is isolated.

Mutant FA(C) gene: a mutant form of the FA(C) gene which is associated with Fanconi Anemia of complementation group C.

Mutant FA(C) RNA: the RNA transcribed from a mutant FA(C) gene.

ORF: open reading frame. Contains a series of nucleotide triplets (codons) coding for amino acids without any termination codons. These sequences are usually translatable into protein.

PCR: polymerase chain reaction. Describes a technique in which cycles of denaturation, annealing with primer, and then extension with DNA polymerase are used to amplify the number of copies of a target DNA sequence.

Protein: a biological molecule expressed by a gene and comprised of amino acids. The standard three-letter nomenclature (as set forth at 37 C.F.R. § 1.822) is used to identify the amino acids.

Purified: the term "purified" does not require absolute purity; rather, it is intended as a relative definition. Thus, for example, a purified protein preparation is one in which the specific protein referred to is more pure than the protein in its natural environment within a cell.

VNTR probes: Variable Number of Tandem Repeat probes. These are highly polymorphic DNA markers for human chromosomes. The polymorphism is due to variation in the number of tandem repeats of a short DNA sequence. Use of these probes enables the DNA of an individual to be distinguished from that derived from another individual.

Additional definitions of common terms in molecular biology may be found in Lewin, B. "Genes IV" published by Oxford University Press.

Detailed Description of the Invention

The present invention identifies three new complementation groups for Fanconi Anemia, designated FA(B), FA(C) and FA(D). These complementation groups are a further subdivision of the non-FA(A) complementation group previously described. This finding may be interpreted to mean that mutations in at least four different genes lead to FA, a degree of locus heterogeneity comparable to other DNA repair disorders.

A novel method was developed to clone DNA molecules which would complement the FA(C) mutation. The technique devised includes constructing a cDNA library in an autonomously replicating Epstein-Barr virus (EBV)-derived vector. The efficiency of cDNA cloning in the library was enhanced by a vector priming strategy. Lymphoblast cells derived from an FA(C) patient were transfected with antibiotic marker genes and transfectants were selected; these transfected cells provided a population of cells with high-efficiency secondary transfection characteristics. This population of cells was then transfected with the cDNA library.

Transfectants were selected for their resistance to the DNA cross-linking agents DEB and MMC. In this way, cells which carried a cDNA which complemented the FA(C) mutation were obtained. Because the EBV cloning vector replicates autonomously in cells, it was then possible to extract cDNA clones from the complemented cells. The cDNA clones which provided such complementation were distinguished from passenger (non-complementing cDNA clones) by a statistical selection procedure. Selected cDNA clones were also tested for their ability to specifically complement the FA(C) mutation by transfection into FA(A), FA(B), FA(C) and FA(D) cells.

Three versions of a single cDNA (designated the FA group C Complementing or FACC cDNA) which specifically complemented only the FA(C) mutation were isolated through this selection procedure. DNA sequence analysis revealed that the three cDNAs varied in size and untranslated 3' regions, suggestive of alternative splice sites and alternative transcription termination points. The cDNAs contained a conserved open reading frame (ORF) encoding a protein (designated the FACC protein) of 558 amino acid residues.

The polymerase chain reaction was then used to amplify the FACC ORF from various FA cell lines. Sequence analyses of these ORFs revealed sequence polymorphisms (mutations) in the ORF of the confirmed FA(C) cell line and in two FA cell lines which were unclassified with regard to complementation groups. No sequence polymorphisms were detected in the FACC ORFs of two normal and five non-group C FA cell lines.

Using the sequence information obtained from the FACC cDNA, a hybridization probe from this cDNA was used to isolate a yeast artificial chromosome clone containing the human genomic FA(C) gene. The vectorette PCR method was then used to define exon boundaries and to determine intron sequences adjacent to intron/exon boundaries within this gene. These experiments indicated that the human FA(C) gene contains 14 exons.

The sequence information produced from these experiments makes possible a genetically based diagnosis of both FA(C) heterozygotes [FA(C) carriers] and sufferers. The present invention also facilitates the study of the FA(C) disease process and should lead to the determination of the underlying biochemical defect of this disease. The invention also enables the development of gene therapy treatments for FA(C) sufferers.

As a means to study the expression of FA(C) gene during development and as a first step in the development of a mouse model for Fanconi Anemia, the mouse homolog of the human FACC cDNA was also isolated. A mouse liver cDNA library was screened under conditions of reduced stringency, using a fragment of the coding region of the human cDNA as a probe. Three positive clones were identified, purified and subcloned into a plasmid vector. The restriction maps of the these three clones overlap and the nucleotide sequence of the entire open reading frame of one of them was determined. In order to ensure that this mouse cDNA (designated Facc cDNA) is indeed the homologous gene to the human FACC cDNA and not simply a related one, the mouse cDNA was assayed for complementation of the MMC sensitivity of human FA(C) cells. The mouse Facc cDNA was found capable of correcting the MMC sensitive phenotypes of FA group C cells and was thus confirmed as the murine homolog of the FACC cDNA.

More particularly, Example 1 is directed to the determination of at least four human FA complementation groups. Example 2 is directed to the isolation of the human FACC cDNA through genetic complementation studies and the characterization of the isolated cDNA. Example 3 is directed to the cloning of the human FACC cDNA coding regions from diagnosed FA patients, and Example 4 relates to the genomic mapping of the human FACC cDNA. Example 5 relates generally to a preferred polymerase chain reaction-based method of making the FACC cDNA clones. Example 6 describes the isolation of a yeast artifical chromosome clone containg the human genomic FA(C) gene and the characterization of the exon structure of this gene by vectorette PCR. Example 7 provides, for the first time, a method for determining if FA sufferers have FA attributable specifically to FA complementation group C. Example 8 is directed generally to variants of the FA(C) gene and the FACC protein that may be obtained through mutagenesis of the nucleotide sequence and DNA molecules presented herein. Example 9 relates to the expression of FACC cDNA sequences and the production of FACC protein in both prokaryotic and eukaryotic cells. Example 10 relates to the production of antibodies to the FACC protein produced by the expression systems described in Example 9. Example 11 relates to novel DNA-based diagnostic procedures for the determination of FA status, and Example 12 relates to the quantitation of FACC protein in cells of patients. Example 13 relates to novel gene therapies for FA(C) which are made possible for the first time by the present invention. Example 14 is directed to the isolation of the murine Facc cDNA by hybridization studies and the characterization of the isolated cDNA clones. Example 15 describes the confirmation of the identity of the murine cDNA clones as the homolog of the human FACC cDNA by complementation studies. Example 16 relates to hybridization studies to determine cross species conservation of the murine cDNA and Example 17 is related to the determination of tissue and developmental specific expression of the murine cDNA by polymerase chain reaction amplification. Example 18 describes in situ RNA hybridization experiments to determine expression of the murine FA(C) gene homolog in mouse embryos.

EXAMPLE 1

Evidence for at Least Four Fanconi Anemia Complementation Groups

Human lymphoblast lines were derived from peripheral blood lymphocytes using the method of Glade and Broder (1971). Three such lymphoblast cell lines (HSC62, HSC230 and HSC536) were derived from FA patients diagnosed on the basis of clinical symptoms as well as increased sensitivity to mitomycin C-induced chromosomal aberrations, and were previously demonstrated to belong to the non-FA (A) complementation group (Duckworth-Rysiecki et al., 1985; Buchwald et al., 1989). The clinical features of the three patients are described in Buchwald et al. (1989) and in Table 1 below where the HSC62 cell line was derived from patient FA2, the HSC230 cell line was derived from patient FA3, and the HSC536 cell line was derived from patient FA8.

TABLE 1

CLINICAL CHARACTERISTICS OF PATIENTS WITH FA
AND PROPERTIES OF CELLS FROM THESE PATIENTS

|  | FA 2 | FA 3 | FA 8 | Normal |
|---|---|---|---|---|
| A. Clinical characteristics | | | | |
| Age of onset (years) | 2 | 3 | 4 | – |
| Birth weight (g) | 1800 | 3000 | – | 3300 |
| Stature (percentile) | <3 | <3 | 50 | |
| Abnormal Pigmentation | – | + | + | – |
| Hand abnormalities | + | – | + | – |
| Kidney abnormalities | – | + | + | – |

TABLE 1-continued

CLINICAL CHARACTERISTICS OF PATIENTS WITH FA
AND PROPERTIES OF CELLS FROM THESE PATIENTS

|  | FA 2 | FA 3 | FA 8 | Normal |
|---|---|---|---|---|
| Bone marrow failure | – | + | + | – |
| Chromosome breakage (%); (lymphocytes) | 10 | <5 | 18 | <1 |
| B. Properties of cells | | | | |
| $D_{10}$ MMC (μg/ml; fibroblasts) | 7.0 | 3.3 | – | 20–24 |
| $EC_{50}$ MMC (nM; lymphoblasts) | 6.9 | 2.9 | 1.1 | 30–50 |

Gene transfer was used to introduce stable selectable markers for cellular resistance to G418 and hygromycin, encoded in the plasmids pSV2neo (Southern and Berg, 1982) or pSV2hph (Santerre et al., 1984), respectively, into each of these cell lines. These plasmids were introduced into the cell lines through transfection of plasmid DNA using Lipofectin (BRL, Gaithersberg, Md.). Briefly, $2 \times 10^7$ lymphoblast cells in logarithmic growth phase were pelleted, washed twice in serum-free medium (SFM) (alpha-MEM, Flow Laboratories, McLean, Va. (Stanners et al., 1971), and resuspended in 3 ml of SFM containing 30 μg of plasmid DNA and 100 μg of Lipofectin. Following incubation for 5 to 7 hours, the reaction was stopped by adding 7 ml of complete medium. The next morning the culture was diluted to 30 ml; selection in 500 μg/ml G418 (BRL) or 400 μg/ml hygromycin B (Sigma, St. Louis, Mo.) was started 48 hrs later. Dead cells were removed over a Ficoll cushion (Nycomed, Oslo, Norway) after 7 days; cells in 5 ml SFM were centrifuged onto a 5 ml cushion of Ficoll at 800×g for 15 mins. The cells were collected from the interphase by removal with a pipette, then washed twice in SFM. Survivors were grown under continuous selection.

A panel of three hybrids, representing the possible crosses of these cells, was constructed. In creating hybrids, one parent cell line was transfected with pSV2neo, the other with pSV2hph, such that true hybrids could be selected by their ability to grow in the presence of both G418 and hygromycin. The cell hybrids were constructed using PEG-mediated cell fusion. Briefly, $10^7$ cells in logarithmic growth phase from each parental cell line were mixed together, washed twice in SFM, and resuspended in a final volume of 0.5 ml. A total of 1.5 ml of a 50% solution of polyethylene glycol (PEG) 1500 in SFM was added dropwise to the pellet over 1 min., followed by 10 ml of SFM added over 5 min. The cells were pelleted and resuspended in 10 ml of complete medium. Desired hybrids were selected by their tolerance to both hygromycin and G418, as described for gene transfer, including removal of dead cells over Ficoll cushions. Southern blot analysis using the variable number of tandem repeats (VNTR) probe D244 (Nakamura et al., 1987) was used to confirm the presence of DNA from both parental lines in each hybrid line.

Figure 2:
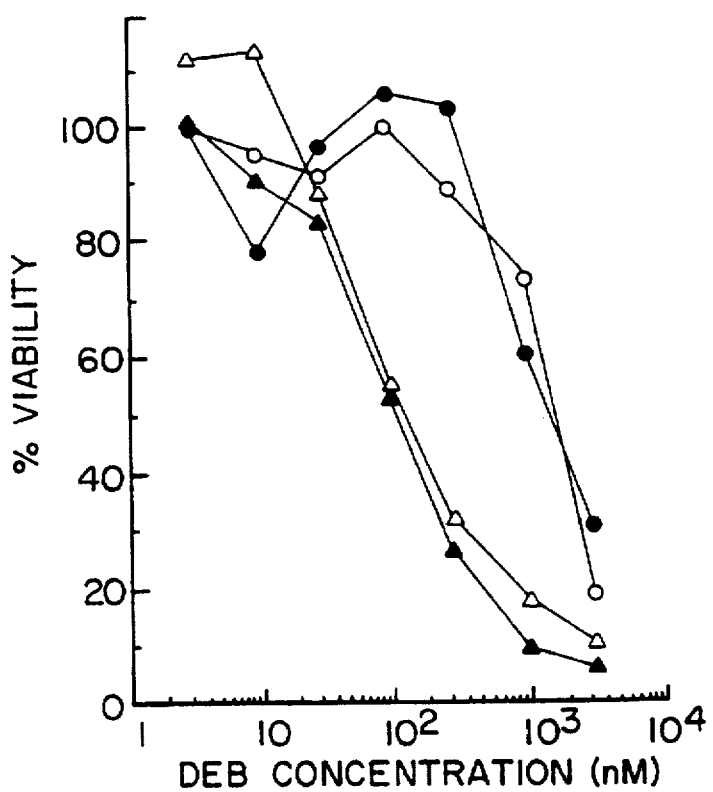
FIG. 2 shows a representative plot of cellular viability with respect to untreated cells following growth in DEB for parental and hybrid fusion cell lines.

Hybrid and parental lines were then assayed for cellular sensitivity to diepoxybutane (DEB) and mitomycin C (MMC). To assay cellular sensitivity, cells in logarithmic growth were plated at a density of $1.5 \times 10^5$/ml in 96 well microtitre plates, and increasing concentrations of either MMC (Sigma) or DEB (Sigma) were added in replicates of 8 wells. After incubation for 5 to 7 days, cellular viability was assayed using 2',7'-bis-(2-carboxyethyl)-5(and 6)-carboxyfluorescein acetoxymethylester (BCECF-AM) (Molecular Probes, Eugene, Oreg.) as a probe specific for intracellular pH (Leeder et al., 1989). The data were fitted to a dose-response curve from which the drug concentration giving a 50% reduction in cell viability (i.e., $EC_{50}$) was calculated. FIG. 2 shows a typical plot of cellular viability with respect to untreated cells following growth in DEB for the HSC62N230H hybrid (open circles), HSC62N (closed triangles), HSC230N (open triangles), and HSC93 normal control (closed circles) cell lines. Table 2 below shows compiled results for assays of cellular DEB and MMC sensitivity for control, parental and hybrid cell lines.

TABLE 2

ASSAYS FOR CELLULAR DEB AND MMC SENSITIVITY

| Cell Line | $EC_{50}$DEB (nM) | | $Ec_{50}$MMC (nM) | |
|---|---|---|---|---|
| HSC93 | 1600 ± 200 | | 360 ± 60 | |
| HSC62N | 120 ± 20 | (0.072) | 29 ± 3 | (0.082) |
| HSC230N | 130 ± 20 | (0.081) | 31 ± 6 | (0.086) |
| HSC536N | 20 ± 3 | (0.011) | 8 ± 2 | (0.021) |
| HSC62N230H | 1600 ± 400 | (0.99) | 200 ± 40 | (0.56) |
| HSC62N536H | 1400 ± 200 | (0.86) | 550 ± 60 | (1.54) |
| HSC230N536H | 1500 ± 300 | (0.90) | 450 ± 70 | (1.27) |

The $EC_{50}$ and associated ± standard deviations for each cell line are indicated in the table. The numbers in parentheses are the normalized values derived by dividing the $EC_{50}$ of a particular cell line by that of the normal control cell line HSC93. The N and H associated with each cell line refer to the presence of a transfected pSV2neo or pSV2hph marker, respectively. The $EC_{50}$ values of each hybrid for both drugs are significantly higher than those of the parental cell lines and are either equivalent to or greater than those of the HSC93 control. The hybrid lines thus reflect specific complementation of the FA defect, rather than a non-specific increase in cellular resistance to DEB or MMC, because cellular sensitivities to both drugs have been corrected to the same degree. In defining the FA(A) complementation group, Duckworth-Rysiecki et al. (1985) examined three different features of FA cell lines with respect to functional complementation (growth inhibition by MMC, spontaneous chromosomal breakage, and MMC-induced chromosomal breakage), and found concordance for all three parameters in all the crosses examined. Similarly, the present data denotes concordance between DEB and MMC hypersensitivities, and leads to the conclusion that the three cell lines described here belong to three new complementation groups, hereby designated FA(B) (defined by HSC230), FA(C) (defined by HSC536), and FA(D) (defined by HSC62), thus extending the total number of FA complementation groups to four. These complementation groups may represent four individual genes, although the possibility of intragenic complementation must also be considered.

EXAMPLE 2

A. Human cDNA Library

Figure 3:
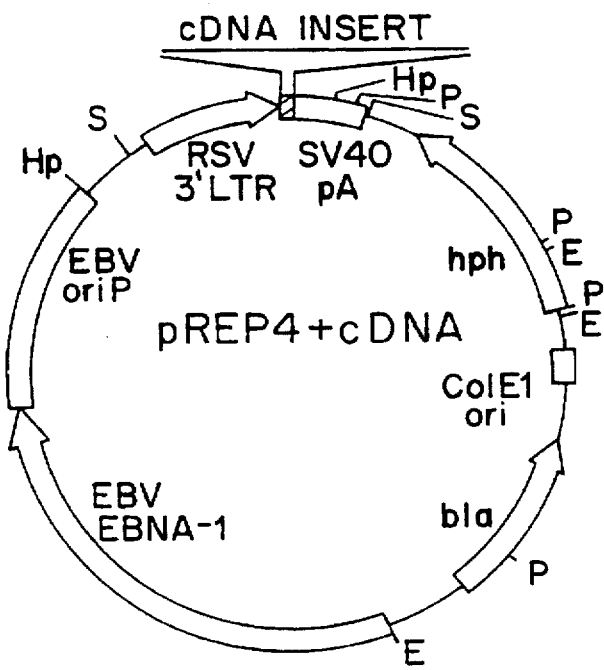
FIG. 3 shows a restriction map of the pREP4 EBV shuttle vector used to construct a cDNA expression library.

A human cDNA library was constructed in pREP4 (Groger et al., 1989) using the Moloney Murine Leukemia Virus-RNaseH reverse transcriptass (BRL) in conjunction with vector primed synthesis to enhance the yield of full-length inserts oriented with respect to the Rous Sarcoma Virus (RSV)-3'Long Terminal Repeat (LTR) promoter and SV40 polyadenylation signal. FIG. 3 shows a restriction map of the pREP4 EBV shuttle vector used to construct the cDNA expression library. The open boxes indicate the orientation of the EBV origin of replication (oriP) and nuclear antigen (EBNA-1), the hygromycin (hph) and ampicillin resistance genes (bla), and the bacterial origin of replication (ColE1 ori) required for selection and replication, as well as the RSV-3'LTR and SV40 polyadenylation signal used to drive cDNA expression. The hatched box indicates the cDNA cloning site. Restriction sites shown on the figure are abbreviated as follows: E, EcoRI; $H_p$, HpaI; P, PstI; S, SalI.

To prepare the vector, 20 μg of a phosphorylated HindIII/poly(T) oligonucleotide primer $(AGCT(T)_{50})$ was ligated to 50 μg of HindIII digested pREP4. The vector was digested with PvuII to generate a 5' blunt end and then purified by chromatography, first over Sephacryl S-200 (Pharmacia, Piscataway, N.J.) to remove unreacted primers as well as the short PvuII-primer fragment and then over oligo(dA) cellulose to purify the poly(T)-tailed vector. Poly(A)$^+$ RNA for the library was isolated through two rounds of oligo(dT) cellulose chromatography from HSC93 lymphoblast cells which were grown in media containing a sublethal dose of 500 nM DEB (Bradley et al., 1988). To prime cDNA synthesis, 5 μg of tailed vector was annealed with 1 μg of RNA, and first and second strand cDNA synthesis was performed using standard methods (Sambrook et al., 1989). The cDNA was blunt-ended with T4 DNA polymerase, and hemi-phosphorylated BamHI-NotI adaptors (Pharmacia) were ligated onto the ends, phosphorylated, and the completed cDNA/vector recircularized. An aliquot of the ligation mixture was electroporated into *E. coli* DH10B, and the resulting library amplified in semi-solid agarose to minimize skewed representation of clones (Kriegler, 1990).

B. Transfection of HSC536N Cell Line and Selection of Complemented Clones.

As described in Example 1, the cell line HSC536N has an integrated PSV2neo marker (Southern and Berg, 1982) introduced through transfection with subsequent selection. Such cells appeared to have a greater efficiency in the uptake of DNA, and therefore serve as more efficient recipients in subsequent transfections. As described in Example 1 and Table 2, HSC536N cells are approximately 20- to 30-fold more sensitive to MMC and DEB than normal cell lines, and approximately 2- to 3-fold more than other FA cell lines. Three independent pools of HSC536N cells were transfected with the cDNA expression library and selected through continuous exposure first to MMC and, after outgrowth of survivors, to DEB. This dual selection strategy takes advantage of the fact that MMC and DEB are metabolized through different pathways during cellular intoxication (Szybalski and Iyer, 1967; Van Duuren, 1969) and facilitates a highly stringent selection. The pREP4-cDNA library was transfected into three independent pools of HSC536N cells using Lipofectin (BRL). Briefly, 2×10$^7$ lymphoblast cells in logarithmic growth phase were pelleted, washed twice in serum-free medium (SFM), and resuspended in 3 ml of SFM containing 30 μg of plasmid DNA and 100 μg of Lipofectin. Following incubation for 5 to 7 hours, the reaction was stopped by adding 7 ml of complete medium. The next morning the culture was diluted to 30 ml; selection in 200 μg/ml hygromycin B (Sigma) was started 48 hours later. Dead cells were removed over a Ficoll cushion (Nycomed) after 7 days, and survivors were grown under continuous selection, minimizing the chance of spontaneous resistance. The pools of cells were then selected continuously in 100 nm MMC until outgrowth of survivors was apparent (about 4 weeks). The cells were washed free of MMC and further selected in 1 μM DEB until outgrowth (about 2 weeks).

C. Isolation and Characterization of cDNAs

Following the selections described above, plasmid DNA was extracted from the MMC and DEB resistant cell lines through alkaline lysis and transfected into *E. coli* DH10B. Plasmids from individual colonies were characterized by restriction enzyme mapping. Many of the plasmids recovered from the selected cells were merely passengers and did not confer resistance to either MMC or DEB, since the EBV replicon in the pREP4 cloning vector is highly efficient, and plasmids may be maintained in lymphoblasts even in the absence of direct selection (Belt et al., 1989). Passengers and complementing cDNAs were distinguished from each other because three independent pools of cells had been maintained during the selection. Only plasmids present at elevated levels in one pool and/or represented in more than one pool were considered to encode candidate FACC cDNAs (FA group C Complementing). Eight candidates were identified after restriction mapping 216 plasmids recovered from the selected cells; the distribution of the frequency of plasmids at the selection of pools is shown in Table 3 below.

TABLE 3

Distribution of the Frequency of Plasmids After Selection of Pools

| Pool | Selective Agent | Plasmid Identification Number | | | | | | | | Others | Total |
|------|-----------------|---|---|---|---|---|---|---|---|--------|-------|
|      |                 | 1 | 2 | 3 | 4 | 5 | 8 | 12 | 14 |       |       |
| 1    | MMC             | 10 | 6 | 2 | 1 | 1 | — | 2 | — | 14 | 36 |
|      | DEB             | 8 | — | 11 | — | — | — | 8 | — | 9 | 36 |
| 2    | MMC             | — | 3 | 16 | — | — | — | — | 2 | 15 | 36 |
|      | DEB             | — | — | 25 | — | — | — | — | 3 | 8 | 36 |
| 3    | MMC             | — | 2 | 2 | 7 | 3 | 11 | — | — | 11 | 36 |
|      | DEB             | — | — | — | 5 | 2 | 26 | — | — | 3 | 36 |
| Complementation | | — | — | + | + | — | + | — | — | | 216 |

The number of times each plasmid was recovered from each pool of selected cells is indicated; "—" means that the plasmid was not recovered in that pool. For complementation, "+" and "—" refer to complementation of the MMC and DEB hypersensitivity of HSC536N cells as described below.

To determine which of the eight candidate plasmids conferred resistance to MMC and/or DEB, representative plasmids were transfected into HSC536N cells using Lipofectin as described above. Cellular sensitivity to DEB and MMC was assayed by plating cells in logarithmic growth at a density of $1.5 \times 10^5$/ml in 96 well microtitre plates. Increasing concentrations of either MMC or DEB were added in replicates of 8 wells and, after incubation for 5 to 7 days, cellular viability was assayed using 2',7'-bis-(2-carboxyethyl)-5(and-6)-carboxyfluorescein acetoxymethylester (BCECF-AM)(Molecular Probes) as a probe specific for intracellular pH (Leeder et al., 1989). The data was fitted to a dose-response curve from which the drug concentration giving a 50% reduction in cell viability (i.e., $EC_{50}$) was calculated.

Figure 4:
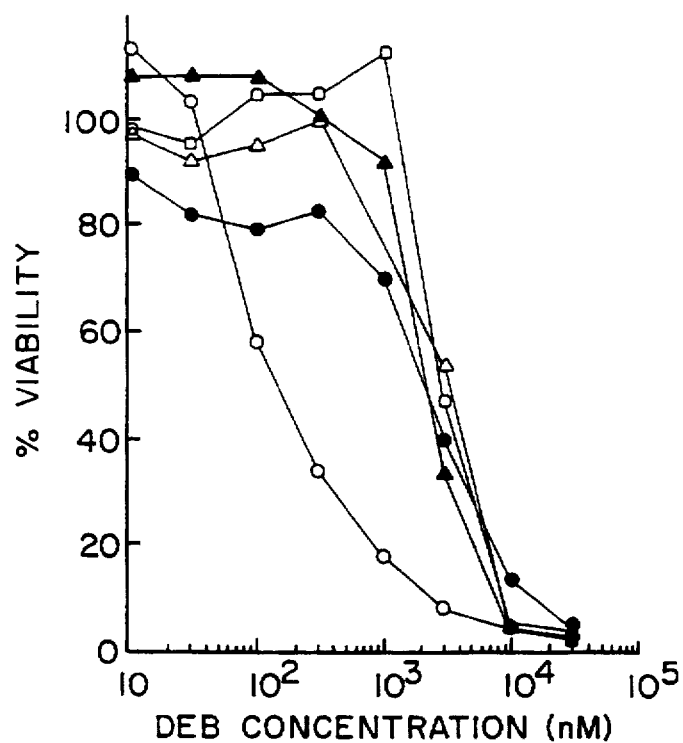
FIG. 4 is a graph showing an analysis of cellular DEB sensitivity for cells transfected with control and candidate plasmids.

Sensitivities to both MMC and DEB were corrected to normal levels with only three of the eight candidate plasmids as indicated in Table 3. These plasmids were designated pFAC3, pFAC4 and pFAC8. FIG. 4 shows an analysis of cellular DEB sensitivity for cells transfected with control and candidate plasmids. The figure is a plot of cellular viability with respect to untreated cells following growth in DEB for the normal control cell line HSC93 transfected with pREP4 vector plasmid alone (closed circles), and HSC536N transfected with either pREP4 (open circles), pFAC3 (closed triangles), pFAC4 (open triangles), or pFAC8 (open boxes). Table 4 gives quantitative data for assays of cellular DEB and MMC sensitivity in transfected HSC536N cells.

TABLE 4

Assays for Cellular DEB and MMC Sensitivity

| Cell Line/ Plasmid | FA Group | $EC_{50}$ | |
|--------------------|----------|-----------|---|
|                    |          | DEB (nM) | MMC (nM) |
| a HSC93/pREP4      |          | 2900 ± 700 | 160 ± 30 |
| HSC536N/pREP4      | C        | 150 ± 20   | 19 ± 3   |
| /pFAC3             | C        | 3000 ± 400 | 260 ± 40 |
| /pFAC4             | C        | 2500 ± 400 | 130 ± 20 |
| /pFAC8             | C        | 3000 ± 600 | 180 ± 30 |

D. Characterization of Plasmids

Figure 5:
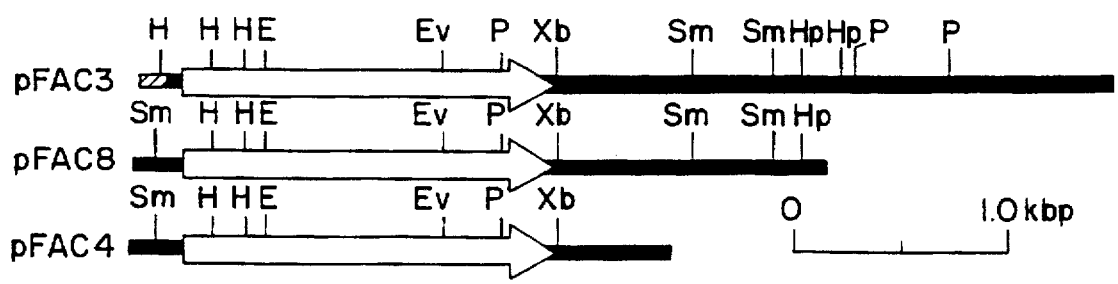
FIG. 5 shows restriction maps of three cDNA molecules extracted from complemented human FA cells.

Detailed restriction mapping of pFAC3, pFAC4 and pFAC8 revealed that they contain 4.6, 3.2, and 2.3 kbp cDNA inserts, respectively. Restriction mapping and subsequent DNA sequence determination indicated that the three cDNAs represent alternatively processed transcripts of the same gene. FIG. 5 shows restriction maps of the insert cDNAs from the indicated plasmids. The open box indicates the location of the common ORF, the closed box indicates common flanking sequences, and the hatched box indicates an alternatively spliced sequence. Restriction sites on the figure are abbreviated as follows: Ev, EcoRV; H, HindIII; Hp, HpaI; P, PstI; S, SalI; Sm, SmaI; Xb, XbaI.

To sequence individual cDNAs, the inserts from each plasmid were first subcloned in their entirety into pBluescript (Stratagene, La Jolla, Calif.) as NotI or BamHI fragments. Both strands of the coding region were sequenced by the Sanger dideoxy method (Sanger et al., 1977) either as further subclones using internal restriction enzyme sites or using FACC specific oligonucleotide primers. The entire sequence of the FACC cDNA and its corresponding translation product (the FACC protein) are presented in FIG. 6. The cDNA is 4569 bp in length, and contains an ORF of 1677 bp encoding a predicted protein of 558 amino acids starting at base 256. Although this is the first in frame ATG (start codon) with a good consensus ribosome binding site (Kozak, 1987), several other downstream in frame ATG codons, if utilized, would yield polypeptides starting at residues 16, 48, or 55 of the indicated FACC protein.

Alternatively processed forms of the cDNA are encoded on pFAC3, pFAC4, and pFAC8 (FIGS. 5 and 6). Sequences of the cDNAs present in pFAC3, pFAC4 and pFAC8 are presented in sequence I.D. Nos. 1, 2 and 3, respectively. Sequence I.D. No. 4 gives the amino acid sequence of the FACC protein. FIG. 6 is a composite sequence showing all three nucleotide sequences and the amino acid sequence. Two different 5' untranslated regions (UTRs) were identified, converging 77 bases upstream of the initiation codon. Sequence analysis does not reveal any conserved splice acceptor or donor sites surrounding this location (Shapiro and Senapathy, 1986), suggesting that the two different 5' UTRs are not artifacts of cDNA synthesis attributable to the presence of unprocessed introns. Rather, the different 5' UTRs likely represent alternatively spliced exons, and these are identified in FIG. 6 as Exon 1 (as found on pFAC 4 and pFAC8) and Exon 1A (as found on pFAC3). To probe the extent of heterogeneity within each exon, the 5' UTR sequence of 24 clones picked at random from those recovered from each independently selected pool of HSC536N cells (Table 3) was determined. Five clones contained Exon 1A, and all five originated at the same base. The remainder of the clones contained Exon 1 and were heterogeneous in length, with the different 5' ends shown as asterisks in FIG. 6. The 3' UTRs of each cDNA also differ in length, and contain identical sequences which are truncated at different points to generate the 2.3, 3.2, and 4.6 kbp cDNAs (FIGS. 5, 6).

Figure 7:
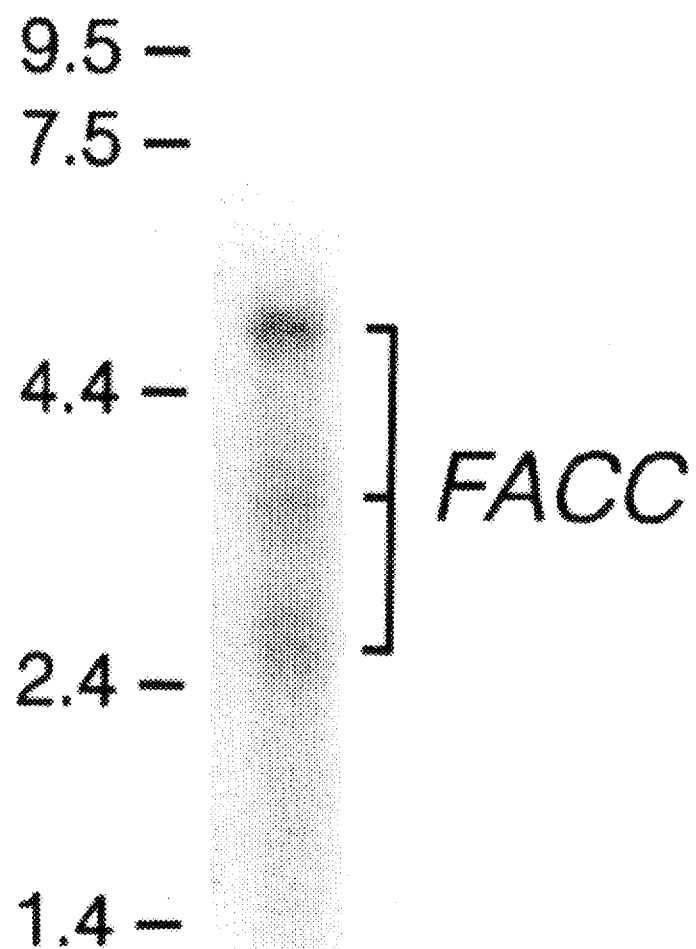
FIG. 7 shows Northern blot analyses of FACC RNA expression in human cells.

Northern blot analyses were used to detect three mRNAs of 2.3, 3.2 and 4.6 kbp in lymphoblasts as shown in FIG. 7. Five µg aliquots of the poly(A)$^+$ RNA purified for the cDNA library construction as described above were electrophoresed through a 1.2% agarose-formaldehyde gel and transferred to a Hybond N$^+$ membrane (Amersham) according to manufacturer's recommendations. The BamHI fragment of pFAC4 was labelled with [α-$^{32}$P]dCTP through random priming for use as a probe (Sambrook et al., 1989). Sequence analysis did not reveal any extensive internal poly(A) tracts which would facilitate misprimed cDNA synthesis, confirming that the different cDNAs represent actual transcripts of the FA(C) gene and are not artifacts of library construction. The longest 3' UTR has a perfect consensus polyadenylation signal (Proudfoot, 1991), located at base 4548, whereas the two shorter 3' UTR have only poor matches, suggesting that the size differences are the result of transcriptional read-through of the first two polyadenylation signals rather than alternative splicing. Interestingly, the longest transcript also appears to be the most abundant (FIG. 7), and contains a series of direct 35 bp repeats preceded by a 12 bp palindrome starting at base 3359 (FIG. 6).

The variations among the FACC transcripts as described above are confined entirely to untranslated regions, with no differences detected throughout the coding sequences for each of the cDNAs examined (FIG. 6). Given the prediction from the cDNA sequence, the FACC protein is about 63 kDa and contains a preponderance of hydrophobic amino acid residues (average hydrophobicity=0.17) (Shapiro and Senapathy, 1986) although no identifiable transmembrane domains are present (Eisenberg, 1984). The theoretical amino acid sequence of the FACC protein is presented in sequence I.D. No. 4.

To confirm the predicted molecular weight of the protein, the entire cDNA was transcribed and translated in vitro. Linearized pFAC (the entire FAC transcript subcloned in pBluescript II (KS-)) (Strategene, La Jolla, Calif.) was used for in vitro transcription. The resulting purified complementary RNA was translated in a reticulocyte lysate translation system (supplied by Promega, Madison, Wis.) according to the manufacturer's instructions. Proteins were labeled with [$^{35}$S]-L-Methionine (Amersham, Arlington Heights, Ill.). Translation products were separated by SDS-PAGE (using 10% polyacrylomide gels), Western blotted onto nitrocellulose membrane (BioRad, 0.45 mm, BioRad, Richmond, Calif.) and autoradiographed. The results of this experiment indicated that the cDNA encodes a protein with an apparent molecular mass of 60 kDa as judged by SDS-PAGE analysis of the in vitro transcribed and translated cDNA.

The cDNA sequence and the translated protein were tested for homology to sequences in the GenBank (Release 70) or EMBL (Release 25) databases and their translated counterparts. No significant homologies were detected. Further, a search through the NBRF-PIR (Release 29), Swiss-Prot (Release 17) and EMBL-Prosite (Release 6.0) databases using the predicted amino acid sequence did not uncover homologies or reveal functional motifs. FACC therefore represents a novel gene involved in the cellular response to DNA damage.

E. Confirmation of Specific Complementation

To further demonstrate that plasmids pFAC3, pFAC4 and pFAC8 specifically complement the FA(C) defect and do not merely confer non-specific resistance to MMC and DEB, each was transfected into lymphoblast lines representative of the other FA complementation groups. These transfections and determinations of cellular sensitivities were performed as described above. The results of these studies are summarized in Table 5.

TABLE 5

| Assays for Cellular DEB and MMC Sensitivity | | | |
|---|---|---|---|
| Cell Line/ | FA | EC$_{50}$ | |
| Plasmid | Group | DEB (nM) | MMC (nM) |
| b HSC93/pREP4 | | 1600 ± 300 | 150 ± 30 |
| HSC720T/pREP4 | A | 46 ± 5 | 6 ± 1 |
| /pFAC3 | A | 61 ± 6 | 13 ± 6 |
| HSC230N/pREP4 | B | 130 ± 20 | 13 ± 1 |
| /pFAC3 | B | 50 ± 9 | 26 ± 4 |
| HSC536N/pREP4 | C | 11 ± 2 | 11 ± 1 |
| /pFAC3 | C | 2100 ± 300 | 240 ± 30 |
| HSC62N/pFAC4 | D | 110 ± 10 | 8 ± 1 |
| /pFAC3 | D | 420 ± 50 | 19 ± 3 |

The EC$_{50}$ and associated±standard deviation for each cell line are indicated. HSC93 is a normal control cell line. pFAC3, pFAC4 and pFAC8 were separately introduced into each cell line; the results were similar for all three plasmids, but only the data for pFAC3 is presented. Full correction of the FA defect was manifested only in HSC536N, leading to the conclusion that the three plasmids confer specific complementation and are the FACC cDNA. Thus, the cloned cDNA molecules contained within plasmids pFAC3, pFAC4 and pFAC8 when transfected into cells from patients with Fanconi Anemia of complementation group C, complement the hypersensitivity to DEB and MMC exhibited by these cells.

EXAMPLE 3

Cloning of FACC cDNA from FA(C) Patients

In order to confirm that aberrant expression of FACC causes the defect in FA(C) patients, the coding regions of FACC cDNA from FA(C) patients were analyzed for the presence of mutations. This was achieved by the polymerase chain reaction amplification of reverse transcribed RNA (RT-PCR) (Veres et al., 1987; Kawasaki et al., 1990). RT-PCR was performed with the oligonucleotides FAC-A1 (CGCTCGAGTGTGCCGACCATTTCCTTC corresponding to base 184 [5' end of the cDNA] and FAC-A4 (CCTGTTCTCCCACCCAGGCCTTTGC corresponding to base 2239 [3' end of the cDNA]) to amplify the FACC coding region from poly(A)$^+$ RNA derived from the FA(C) cell lines. The thermal profile used was 96°, 20s; 72°, 120s for 40 cycles. PCR products from 4 independent amplifications were pooled, residual primers removed, and then sequenced directly (McCabe, 1990) using nested internal primers spaced at 250 bp intervals.

Figure 8:
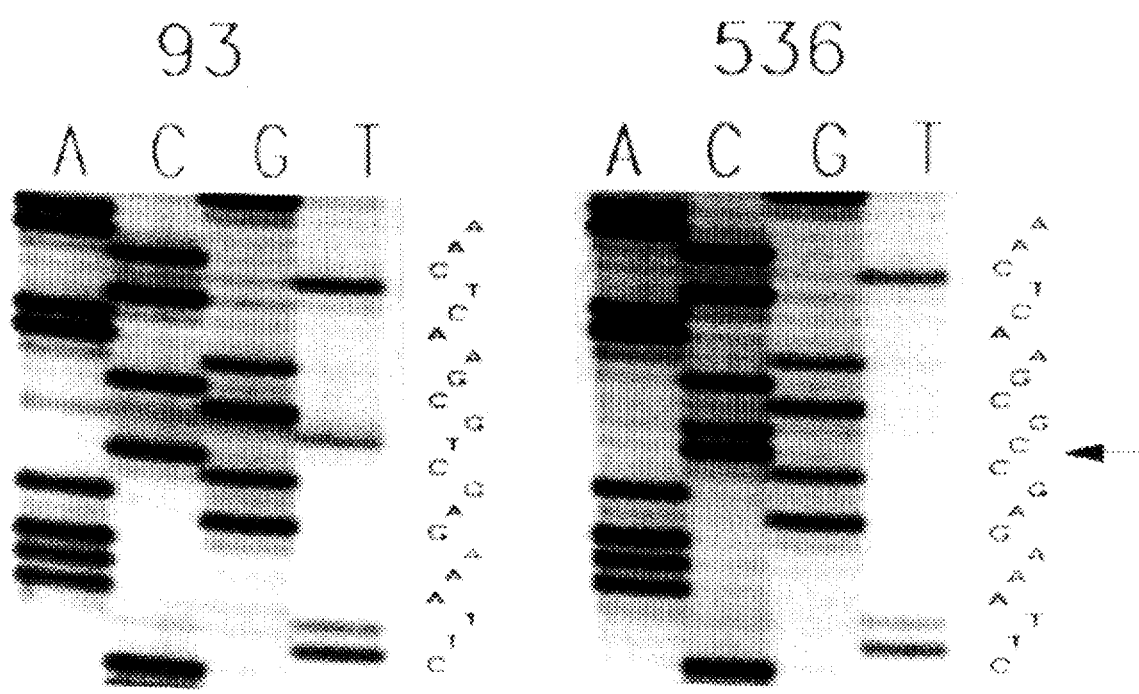
FIG. 8 shows DNA sequencing reactions for the FACC cDNAs amplified from the cell lines HSC93 and HSC536N.

The strategy of pooling PCR products from 4 independent amplifications and then directly sequencing these products was used to eliminate Taq polymerase errors as a source of sequence variation. HSC536N cells, which represent the sole confirmed FA(C) cell line, have a T to C transition at base 1916 of the cDNA molecule numbered as shown in FIG. 6. This transition changes codon 554 from leucine to proline (L554P) compared with the control cell line HSC93 as shown in FIG. 8. In FIG. 8, the respective cell lines and sequencing reactions are shown along the top of the autoradiogram. The FACC cDNA sequence and the location of the mutation are indicated down at the side of each figure. Because L554P leads to the loss of a BbvI site, it was possible to determine that the patient is heterozygous for L554P and that this mutation is maternally inherited. The inherited paternal mutation must therefore lead to a non-expressed allele. Subsequent experiments using in vitro mutagenesis and complementation tests have revealed that this sequence leucine to proline change completely abolishes the activity of the FACC protein as analyzed by the functional complementation assay.

No sequence polymorphisms were detected in the FACC coding region of two normal and five non-group C FA cell lines that constitute the other three FA complementation groups. However, in two out of four unclassified FA cell lines, a deletion of a single G at base 322 in one allele was detected leading to a truncated peptide of 44 residues. No other mutations were detected in the coding region of the FACC cDNA of these two cell lines; the other mutation likely resides in the 5' UTR, 3' UTR or promoter regions of the gene. The conclusion that these two cell lines belong to group C can be tested through complementation analysis using the cloned FACC cDNA. Such an assay presents a simple alternative to the previous methodology, based on somatic cell hybridization (Duckworth-Rysiecki et al., 1985) for establishing the complementation group status of unknown FA cell lines and may be useful in identifying FA(C) cell lines in a more widespread search for FACC mutations.

EXAMPLE 4

Genomic Mapping of the FACC cDNA

Figure 9:
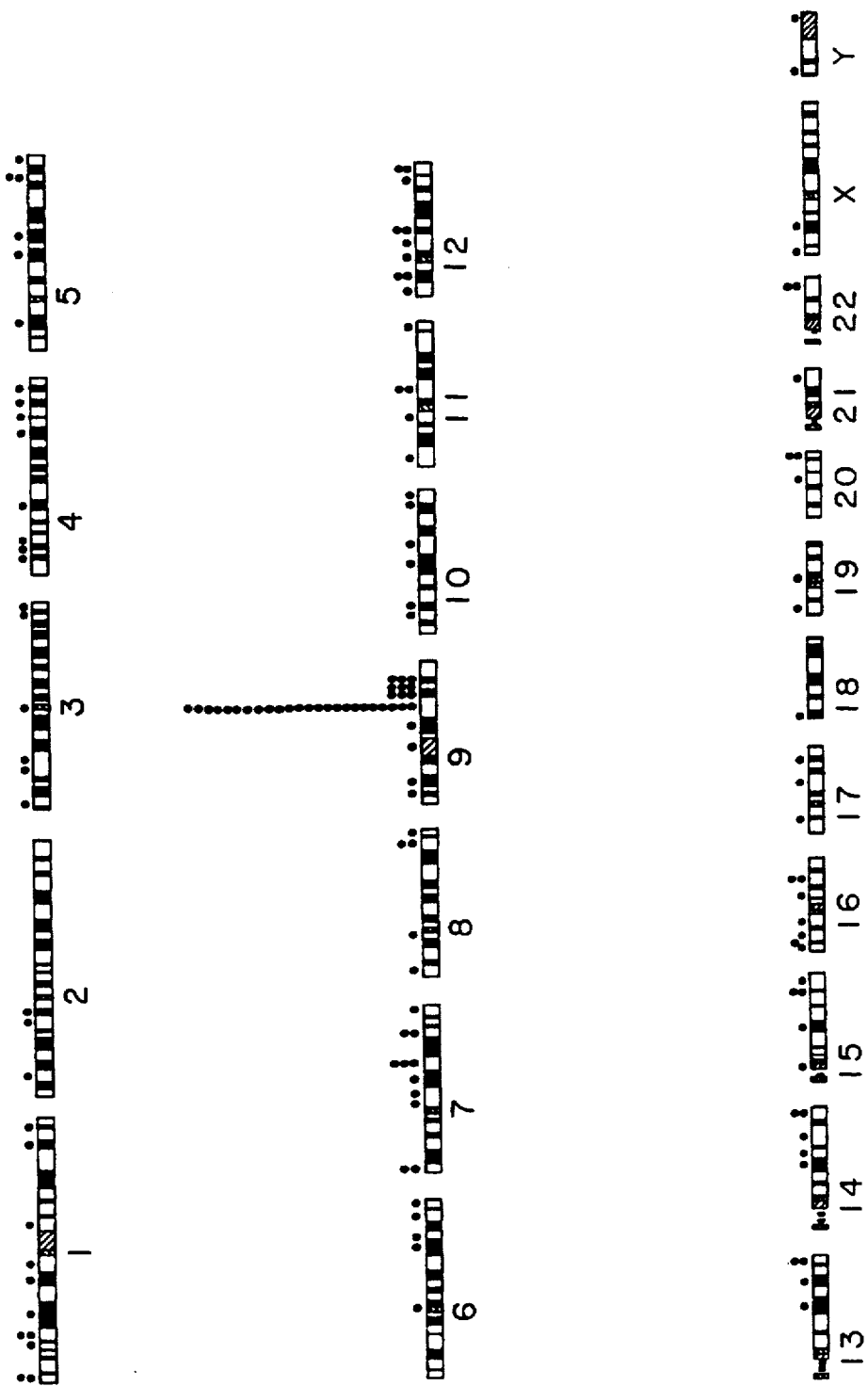
FIG. 9 is a karyotype analysis showing silver grain distribution, following in situ hybridization of the FACC probe, localizing to human chromosome 9q.

The FACC cDNA was mapped to a specific chromosomal location in the human genome using in situ hybridization. Plasmid FAC-EX was obtained by subcloning a 1.4 kb EcoRI to XbaI fragment from pFAC3 (as shown in FIG. 5) into the plasmid Bluescript SK+ (Stratagene). Plasmid FAC-Ex was labelled to a specific activity of $3 \times 10^7$ cpm/µg DNA with [$^3$H]-dTTP and [$^3$H]-dATP (New England Nuclear [NEN], Boston, Mass.) using a multiprime DNA labelling system (Amersham, Arlington Heights, Ill.). In situ hybridization to BrdU-synchronized peripheral blood lymphocytes was performed using the method of Harper and Saunders (1981). Briefly, metaphase chromosomes on slides were denatured for 2 min. at 70° in 70% deionized formamide, 2×SSC (Standard Saline Citrate, where 1×SSC comprises 0.15M sodium chloride, 0.015M sodium citrate, pH 7.0). Slides were then dehydrated with ethanol. The probe hybridization mixture consisted of 50% deionized formamide, 10% dextran sulfate, 2×SSC (pH 6.0), 02 µg/ml probe DNA, and 20 µg/ml sonicated salmon sperm DNA. The probe was denatured in the hybridization solution at 70° C. for 5 min. Fifty µl of hybridization mix were placed on each slide which was then coverslipped, sealed with rubber cement and incubated overnight at 37°. Posthybridization washes were 3 times 3 min. in 50% deionized formamide, 2×SSC, and 5 times 3 min. in 2×SSC (pH 7.0). The slides were sequentially dehydrated in ethanol, coated with Kodak NTB/2 emulsion, exposed for 3 weeks at 4° C. and developed. Chromosomes were stained with a modified fluorescence, 0.25% Wright's stain procedure (Lin et al., 1985). The positions of silver grains directly over or touching well-banded chromosomes were mapped to an International System of Human Cytogenetic Nomenclature (ISCN)-derived idiogram of the human karyotype (Harnden and Klinger, 1985). This mapping revealed a significant clustering of grains in the 9q22.3 region (P<0.0001) as shown in FIG. 9. The FA gene mapped by Mann et al. (1991) to chromosome 20q cannot then be the FA(C) gene. The mapping data for FACC further confirms the novelty of this DNA sequence.

EXAMPLE 5

Preferred Method of Making cDNA Clones

Example 2 above provides a means for obtaining the FACC cDNA clones and also provides the nucleotide sequence of these cDNA clones. Based upon this information, the polymerase chain reaction (PCR) may now be utilized in a preferred method for producing the disclosed cDNAs. As described in Example 3, the PCR may be utilized in conjunction with oligonucleotide primers derived from the presented DNA sequence to amplify these cDNAs from human cells.

Example 3 provides a description of one possible method of cloning FACC cDNAs from human cells using this approach. Example 3 provides primers which may utilized for the PCR amplification of the open reading frame portion of FACC cDNAs and also provides conditions suitable for such amplificationl Other regions of FACC cDNA may be amplified by PCR through modification of this approach. Essentially, total RNA is extracted from human cells by any one of a variety of methods routinely used; Sambrook et al. (1989) and Ausubel et al. (1987) provide descriptions of methods for RNA isolation. Any human cell line derived from a non-FA individual would be suitable, such as the widely used HeLa cell line, or the WI-38 human skin fibroblast cell line available from the American Type Culture Collection, Rockville, Md. The extracted RNA is then used as a template for performing the reverse transcription-polymerase chain reaction (RT-PCR) amplification of cDNA. Methods and conditions for RT-PCR are described in Kawasaki et al. (1990). The selection of PCR primers will be made according to the portions of the cDNA which are to be amplified. Primers may be chosen to amplify small segments of a cDNA or the entire cDNA molecule. Variations in amplification conditions may be required to accommodate primers of differing lengths; such considerations are well known in the art and are discussed in Innis et al. (1990). The entire cDNA molecules, corresponding to clones PFAC3, PFAC4 and PFAC8, may be amplified using the following combinations of primers:

pFAC3
primer 1  5' GAGCCCCCGGAGAGGCGGGAGCGGTGTTGG 3'
primer 2  5' AGGTGCAAACTGAAGTTTTATTTAGAATGA 3' pFAC4
primer 1  5' ACTGCTGACACGTGTGCGCGCGCGCGGCTC 3'
primer 2  5' CTCTCTAAATTCTTTAATGGTTCATGACCA 3' pFAC8
primer 1  5' ACTGCTGACACGTGTGCGCGCGCGCGGCTC 3'
primer 2  5' CAAAATGGACAAAAGCAAGTCTTGACTCAC 3'

The foregoing primer sequences are set forth in the accompanying sequence listing as Seq. I.D. Nos. 33–38. These primers are illustrative only; it will be appreciated by one skilled in the art that many different primers may be derived from the provided cDNA sequence in order to amplify particular regions of these cDNAs.

EXAMPLE 6

Cloning of the FA(C) Genomic Gene and Characterization of the Exon Structure of this Gene The FACC cDNA sequence described above does not contain the introns, upstream promoter and regulatory regions or downstream regulatory regions of the FA(C) gene. It is possible that some mutations in the FA(C) gene that may lead to FA are not included in the cDNA but rather are located in other regions of the FA(C) gene. Mutations located outside of the open reading frame that encodes the FACC protein are not likely to affect the functional activity of the protein but rather are likely to result in altered protein levels in the cell. For example, mutations in the promoter region of the FA(C) gene may prevent transcription of the gene and therefore lead to the complete absence of the FACC protein in the cell. Such a scenario may be responsible for the apparent non-expression of one of the two FACC alleles in HSC536N cells as described in Example 3.

Additionally, mutations within intron sequences in the genomic gene may also prevent expression of the FACC protein. As illustrated in FIG. 1, following transcription of a gene containing introns, the intron sequences are removed from the RNA molecule in a process termed splicing prior to translation of the RNA molecule which results in production of the encoded protein. When the RNA molecule is spliced to remove the introns, the cellular enzymes that perform the splicing function recognize sequences around the intron/exon border and in this manner recognize the appropriate splice sites. If there is a mutation within the sequence of the intron close to the junction of the intron with an exon, the enzymes may not recognize the junction and may fail to remove the intron. If this occurs, the encoded protein will likely be defective. Thus, mutations inside the intron sequences within the FA(C) gene (termed "splice site mutations") may also lead to FA.

Shortened FACC transcripts have been detected in several patients. Such shortened transcripts may be the result of splice-site mutations. However, knowledge of the exon structure and intronic splice site sequences of the gene is required to define the molecular basis of these abnormalities. Furthermore, as a consequence of the pancytopenia found in FA patients and the poor growth characteristics of FA cell-lines, only genomic DNA is available from the majority of patients. Efficient screening of the FA(C) gene for mutations in these patients by PCR amplification of genomic DNA as described in Example 11 requires knowledge of the exon structure and adjacent intron sequences of the gene.

The provision herein of the FACC cDNA sequence has enabled the cloning of the entire FA(C) gene (including the promoter and other regulatory regions and the intron sequences) and the determination of its nucleotide sequence. With this information in hand, diagnosis of FA carrier/sufferer status based on DNA analysis as described in Example 11 will comprehend all possible mutagenic events at the FA(C) locus.

As described below, a yeast artificial chromosome (YAC) clone containing the FA(C) gene has been isolated and analyzed to define exon boundaries and to determine adjacent intron sequences as described below. This information will facilitate screening and characterization of mutations in the FA(C) genes of Fanconi anemia patients.

A YAC library of human genomic sequences (Monaco and Lehrach, 1991) was screened for the FA(C) gene by the polymerase chain reaction (PCR). The library was arranged in 39 primary DNA pools, prepared from high-density grids each containing 384 YAC clones. Primary pools were screened by PCR to identify a pool which contained a positive clone. A secondary PCR screen was then performed on the appropriate set of eight row and 12 column pools, as described by Bentley et al. (1992). PCR primers corresponding to base pairs 1864–1885 and 2239–2214 of the FACC cDNA sequence shown in FIG. 6 (referred to respectively as 1864–1885F and 2239–2214R; F and R referring to forward and reverse primers respectively) were used as a sequence tagged site (STS) for the 3' region of the gene. The yeast DNA was then amplified by PCR for 30 cycles of 94° C. for 1 minute, 60° C. for 1 minute and 72° C. for 1 minute, with a final 5 minute extension at 72° C. One positive YAC was obtained by this method. Confirmation that it contained the majority of the coding sequence of the FA(C) genomic gene was obtained by amplification of an STS from the 5' end of the gene (using primers 194–212F and 344–322R).

Figure 16:
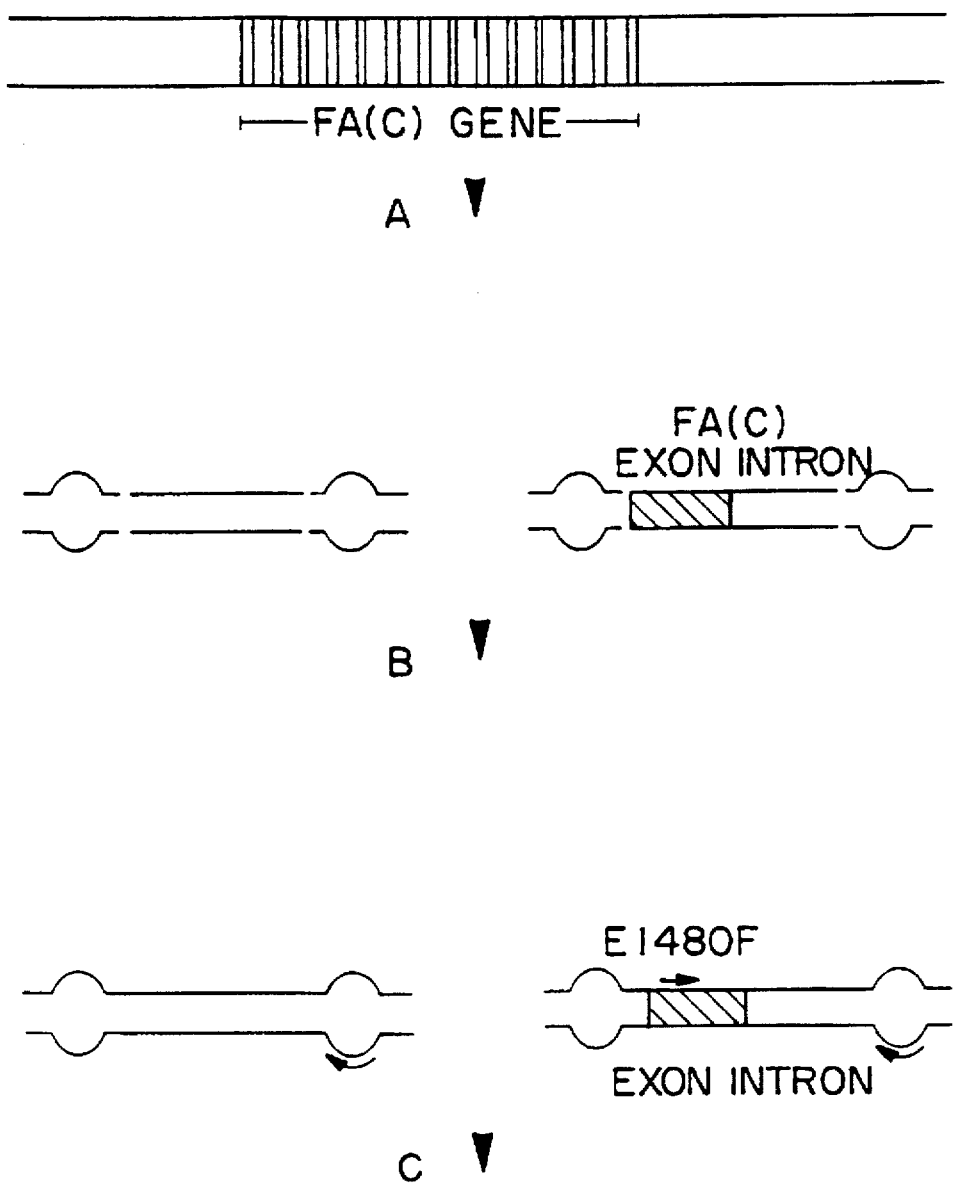
FIG. 16 is a diagram showing the principle of vectorette PCR to detect exon boundaries, using exon 12 of the FACC gene as an example. No amplification occurs unless the exon 12 specific primer creates a template for the vectorette primer. The sequence which follows exon 12 is intronic and contains the highly conserved donor splice site.

The strategy used to characterize exon boundaries was the vectorette PCR method. This strategy has been described in detail previously (Roberts et al., 1992). The principle of the vectorette PCR method is illustrated in FIG. 16. Vectorette libraries of the FA(C) YAC were constructed based on the method of Riley et al. (1990) and Roberts et al. (1992) essentially as described below. Agarose plugs of yeast DNA were digested with one of the three restriction enzymes RsaI, HaeIII and AluI. These digests were then ligated with annealed vectorette oligonucleotide, and the diluted ligation mix was stored at –20° C. Vectorette PCR was performed using the vectorette PCR primer 224 described in Riley et al. (1990) and an FA(C)-specific primer for 38 cycles in 50 microliter reaction volume containing 1 unit of perfect match enzyme (Stratagene, LaJolla, Calif.). PCR products from the FA(C) YAC and from control YACS which did not contain the FA(C) gene were then analyzed by gel electrophoresis. FA(C)-specific bands were excised from the gel and purified either using Geneclean (Bio101) cartridges (for fragments>200 base pairs in size), or by electrophoresis on to NA45 DEAE membranes (Schleicher and Schuell, Keene, N.H.) followed by elution in 1M NaCl and ethanol precipitation (for fragments<200 base pairs in size).

Gel-purified PCR products were sequenced directly as described by Green et al. (1989), with the inclusion of 10% dimethylsulfoxide in the sequencing reaction as described by Winship (1989). Sequencing was carried out using exon-specific primers, or the vectorette primer 224 described by Riley et al. (1990).

PCR amplification of the coding exons and their flanking intron sequences was carried out in 25 μl reactions with 250ng of genomic DNA, 10ng/μl of each primer, 0.5 mM of each dNTP, and 1.5 units of Taq polymerase in a buffer containing 6.7 mM $MgCl_2$ according to Roberts et al. (1992). After initial denaturation at 94° C. for 5 minutes, samples were amplified for 30 cycles of denaturation at 94° C. for 1 minute, annealing at 60° C. for 1 minute and extension at 72° C. for 1 minute, followed by a final 5 minute extension at 72° C.

Several putative exon boundaries were identified as a result of sequencing shortened RNA-PCR products from FA patients. For example, a transcript from one patient had a deletion of bases 1585–1788 (numbered according to FIG. 6) which suggested that these two positions might be located at exon boundaries. PCR primers were then designed from the cDNA sequence 5' and 3' to these positions, and used as the specific primer to amplify DNA from the vectorette libraries. Direct sequencing of the gel-purified products confirmed the presence of exon boundaries at these two positions. Once a boundary had been defined, primers were designed from the cDNA so that the donor and acceptor splice sites in the intron could be amplified and sequenced. The FA(C)-specific PCR primers used to characterize all of the exon boundaries in the coding sequence of the FA(C) gene are presented in Table 6, together with the approximate length of the vectorette PCR products obtained. Primers located in exon sequences are denoted "E", primers located in intron sequences are denoted "I". F and R refer to Forward and Reverse primers for PCR amplification. Intron primer sequences are given in b–f.

TABLE 6

Vectorette PCR primer sequences[a]

| Name Product | Position | Vectorette enzyme[g] | size(bp) |
|---|---|---|---|
| E198F | 198–217 | H | 800 |
| E350F | 350–370 | H | 400 |
| I421F[b] | | H | 1000 |
| E431F | 431–450 | H | 900 |
| E483R | 483–462 | A | 600 |
| E523F | 523–542 | A | 500 |
| E578R | 578–558 | A | 400 |
| E611F | 611–632 | H | 300 |
| E680R | 680–660 | A | 1000 |
| E720F | 720–740 | A | 900 |
| I776R[c] | | A | 500 |
| E797F | 797–815 | R | 300 |
| E891R | 891–869 | A | 500 |
| E1056F | 1056–1078 | A | 500 |
| E1076R | 1076–1057 | H | 450 |
| E1109F | 1109–1128 | H | 300 |
| E1141F | 1141–1162 | R | 2000 |
| I1150R[d] | | H | 1400 |
| E1198F | 1198–1218 | H | 300 |
| E1206R | 1206–1187 | R | 340 |
| E1260F | 1260–1280 | R | 600 |
| E1310R | 1310–1291 | R | 300 |
| I1328F[e] | | H | 550 |
| E1361R | 1361–1341 | A | 500 |
| E1390R | 1390–1369 | A | 600 |
| E1430R | 1430–1412 | A | 600 |
| E1480F | 1480–1501 | A | 300 |
| E1500R | 1500–1479 | H | 350 |
| E1614F | 1614–1634 | R | 300 |
| E1674R | 1674–1654 | A | 300 |
| E1734F | 1734–1753 | R | 160 |
| E1783R | 1783–1763 | A | 160 |
| I1788R[f] | | A | 500 |
| E1839R | 1839–1819 | H | 300 |

[a]Position of 5' & 3' ends of exon primers are numbered according to FIG. 6.
[b]I421F: GCA TAA TGC CTT TAC TGA CC
[c]I776R: CAC CTA CCG CCT TTG AGT G
[d]I1150R: CAG CCA GAG ACT ACC ACA AC
[e]I1328F: CTC TCC ACC CGC AGA TAT CC
[f]I1785R: GTC CGT CCC TGG ACA AAG GAC
[g]A = AluI, H = HaeIII, R = RsaI Table 6 includes several intron primers which were designed from intron sequences as required. The genomic continuity of all the exons was established by direct sequencing with primers of opposite orientation to the specific primers used to generate the vectorette product. The primer sequences set forth in B–F in Table 6 are presented in the accompanying sequence listing as Seq. I.D. Nos. 39–43.

Figure 17:
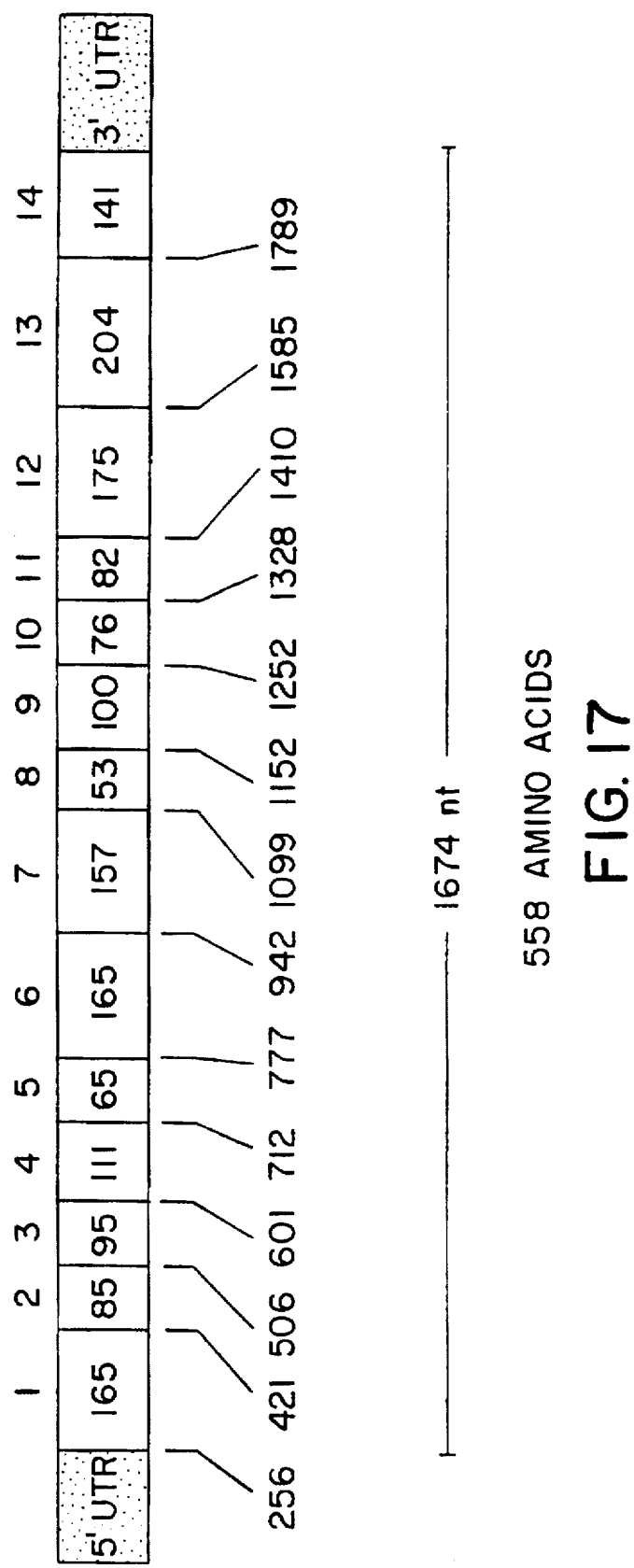
FIG. 17 shows the exon structure of the coding region of the human FA(C) gene as determined by vectorette PCR. The exon number which is shown above each box is subject to detailed characterization of the 5' untranslated region. The length of each exon in base pairs is given within the boxes, and the base position from which each exon begins is given below. (Sizes of exons 1 and 14 refer to the coding region of these exons only). The numbering of the bases is according to FIG. 6.

The sequence information obtained from the vectorette PCR products listed in Table 6 defined a total of 14 exons in the coding region of the FA(C) gene, ranging in size from 53 base pairs to 204 base pairs. Their positions and sizes are shown in FIG. 17. Since the exon structure of the 5' and 3' untranslated regions have not been fully characterized, the numbering of the FA(C) exons from 1 to 14 is provisional. The genomic sequences immediately upstream and downstream of the start and end of the coding sequence, respectively, do not appear to be interrupted, since amplification of genomic DNA with a 5' STS from bases 194 to 344 and a 3' STS from bases 1861 to 2236 produced the product size expected from the cDNA sequence. The sizes of exon 1 and exon 14 refer to coding region only.

Intron sequences obtained by vectorette PCR showed that all exons had donor and acceptor splice sites which conformed with the 5'/gt . . . ag/3' rule set forth in Breathnach and Chambon (1981) and these sequences fitted well with published consensus sequences. The splice sites were scored according to Shapiro and Senapathy (1987). The range for acceptor site scores was 80–99, and donor sites scored from 78–97. Intron sequences at the exon boundaries and their associated splice site scores are presented in Table 7 below.

TABLE 7

Intron sequences[a] at FA(C) donor and acceptor splice sites

| Exon No. | Acceptor | Donor | RF[b] | Acceptor splice[c] | Donor splice[c] |
|---|---|---|---|---|---|
| 1 | ATG- | -ATGgtaagtagtggaccagaataatg | — | — | 92 |
| 2 | caaaatttattttctttcacagGAT- | -ATGgtaagaatcaaaaacgtgtcctc | 3 | 99 | 86 |
| 3 | ttattaagttttcctttttgtagATG- | -CAGgtaagagagtaaatcttgctctg | 1 | 86 | 94 |
| 4 | cttttctgtttatgtttttagGGT- | -AATgtgagtatttaatatttatcact | 3 | 90 | 84 |
| 5 | ctgcaactgattttgttttacagATG- | -GCGgtaggtgttaaactaaacatcct | 3 | 96 | 81 |
| 6 | attatttcttatttcttccatagAAT- | -GCTgtaagtggcaaatgtttcctgtc | 2 | 85 | 79 |
| 7 | ttttgtttatttctttctgaaagGAA- | -CTGgtacgtactgggtttgatgaag | 2 | 86 | 80 |
| 8 | ctcatggtcttctccttttacagCCT- | -CAGgtaaacgttacactgtttcttct | 3 | 92 | 79 |
| 9 | tgatctgactttgcattgttcagGTG- | -CAGgtttgttatatcacatatattac | 2 | 90 | 78 |
| 10 | ttggattttccatcctgtggcagCTG- | -AAGgtgagttagggttgactttgccc | 3 | 80 | 97 |
| 11 | gacgtatctctctccacccgcagATA- | -TGGgtgagcaaacactgaccactccc | 1 | 87 | 83 |
| 12 | catgtgttctgcctctgttccagGTC- | -ATGgtgggtagcaggccccactgcat | 2 | 93 | 78 |
| 13 | ccctgtgaaatactattgcccagGTC- | -CTGgtaagtctccctgtggtccagct | 3 | 83 | 92 |
| 14 | cttctcttctgtcctgattgcagATG- | -GTC | 3 | 87 | — |

[a]Intron sequences are denoted by lower case letters. The first and last codon of each exon is given in upper case. More extensive intron sequences have been submitted to the GenBank/EMBL Databases (accession numbers L02651–L02664).
[b]1, 2, 3: 5' exon boundary occurs after the first, second or third base of a coding triplet respectively (RF = reading frame).
[c]Scores for adherence to consensus acceptor and donor splice sites, calculated according to the method of Shapiro and Senapathy (1987).

More extensive sequences from these regions have been deposited in GenBank/EMBL databases (accession numbers L02651-L021664) and are presented in Table 8, below. In Table 8, intron sequences are shown in lowercase letters, the intron-exon boundary is denoted by a slash (/) and exon sequences are shown in uppercase letters. The sequences shown in Tables 7 and 8 for intron numbers 1–14 are set forth in the accompanying sequence listing as Seq. I.D. Nos. 5–30.

TABLE 8 exon 1 . . . ATG / gtaagtagtg gaccagaata atgaaattat tttctgactt cagggactct accagatttc accaagacag aatgccaccc agaatcggga cttgtggt . . .

ttccctcaat ctataatgtc agttcagtat ttctaagttg cataatgcct ttactgacc aaaattatt tttctttcac ag / GAT . . . exon2 . . . ATG / gtaagaatca aaaacgtgtc ctctcaaaaa tggctatttt aatctttgca ttgtttcaca gaggcttac . . .

tagtagtttg agattttcct aaatataatg tttacagtgt tttttatatt aatgatttt tctgcttgat aaaacttatt aagttttcct tttgtag / ATG . . . exon3 . . . CAG / gtaagagagt aaatcttgct ctgcacttct ttgaattaaa ttgattattt aaaagtgctg cttaaaaaaa . . .

taaattgtag gcattgtaca taaaaggcac ttgcatttac ttttaaagaa gttaacttt tctgtttatg ttttttag / GGT . . . exon 4 . . . AAT / gtgagtattt aatatttatc acttttgaaa tgtttaatg ctgaatgtgc cat . . .

tagaactgatgta atcctgtttg cagcgtgagt taacctgcaa ctgattttgt tttccag / ATG . . . exon 5 . . . GCG / gtaggtgtta aactaaacat ccttctctc aggtttcaaa atgtatcagt ttggttatga gaggaaaatt tt . . .

atatgtcctt aattatgcat ggctcttaga tttgagtgat tatttcttat ttcttccata g / AAT . . . exon 6 . . . GCT/ gtaagtggca aatgtttcct gtcatcctgc gtcgttttc cttttcttag aaggctgtgg tgtgttggaa a . . .

tttttttcagt gagccatttc tgtttaaaat tttgtttatt tctttctgaa aag / GAA . . . exon 7 . . . CTG / gtacgtactg ggtttttgatg aagggaaaaa tccttgaagg acatgcttgg actcatttct ttt . . .

aactcctttg gctgataata gcaagttt(c/t)t gagaaagtgc ttgtgatatt tcacattctc atggtcttct ccttttacag / CCT . . . exon 8 . . . CAG / gtaaacgtta cactgtttct tctagtaattg atgtaaaaaa ggttccatttt ccaagcatga atcagaaaat gttgtggtag tctctggctg tatcatgggg . . .

aagtcttatgg cacaaaaaaa gtgtttctac ttttccctta tacagtgcag gtttcatgt ttgccggatt acttgttaaa cgtgttctga tctgactttg cattgttcag / GTG . . . exon 9 . . . CAG / gtttgttata tcacatatat tactcattca cccagagaat aagacgctgt tgagagtatt ttggacaaga gcactttatt ttcaataatt ttgatggact gtttt . . .

agagttttgt attttcctga ccccgtttca atcttaatgt tcatgctctt tggatttcc atcctgtggc ag / CTG . . . exon 10 . . . AAG / gtgagttagg gttgacttgc ccacatcaga atgaNNtcct gggaagagca ttgtcaaatt atga . . .

gtgaaccaga agtaaagggc gtctcccaaa gactcttcag gtcatccctg caggtggttc ctcatggggt tgacatttcc tcagttgccc tctgacgtat ctctctccac ccgcag / ATA . . . exon 11 . . . TGG / gtgagcaaac actgaccact cccaaatctg cttcacacat ggtttcccta gatcct . . .

aaaaacccaa aggaagaaga atttaggttg tcaactgcca tgtgttctgc ctctgttcca g / GTC . . . exon 12 . . . ATG / gtgggtagca ttccccactg catgtgtttg gggNNggctc tggggggcta gaggagcaag gagagg . . .

aatcctagaa gtatgtctgt cctgNNtctc ctaacctctc ccctgtgaaa tactattgcc cag / GTC . . . exon 13 . . . CTG / gtaagtctcc ctgtggtcca gcatcctagt caaggagagg acagca . . .

tggaaatgct ggataggggct tctttcaggg actgggtggt tatggtccgt ccctggacaa aggacaaatc tgtctggaaa gtgttttaat ttgccttctc ttctgtcctg attgcag / ATG . . . exon 14 . . . GTC . . . 3'UTR . . .

PCR reactions were designed and tested for amplification of the 14 coding exons from genomic DNA. The primer sequences and PCR product seizes are listed in Table 9 below. These primer sequences are also set forth as Seq. I.D. Nos. 44–71 in the accompanying sequence listing.

TABLE 9

PCR reactions for the 14 coding exons of the FA(C) gene

| Exon | Primer sequence (5'-3') | Product size (bp) |
|---|---|---|
| 1 | F: ACCATTTCCTTCAGTGCTGG<br>R: ACCACAAGTCCCGATTCTGGG | 326 |
| 2 | F: CCCTCAATCTATAATGTCAG<br>R: GTAAGCCTCTGTGAAACAATG | 232 |
| 3 | F: TAGTAGTTTGAGATTTTCC<br>R: GCAGCACTTTTAAATAATC | 254 |
| 4 | F: GTAGGCATTGTACATAAAAG<br>R: TGGCACATTCAGCATTAAAC | 234 |
| 5 | F: CTGATGTAATCCTGTTTGCAG<br>R: CCTCTCATAACCAAACTGATAC | 184 |
| 6 | F: GTCCTTAATTATGCATGGCTC<br>R: CAACACACCACAGCCTTCTAAG | 289 |
| 7 | F: TTTTCAGTGAGCCATTTCTG<br>R: AAATGAGTCCAAGCATGTCC | 265 |
| 8 | F: CTCCTTTGGCTGATAATAGC<br>R: CCCATGATACAGCCAGAGAC | 232 |

TABLE 9-continued

PCR reactions for the 14 coding exons of the FA(C) gene

| Exon | Primer sequence (5'-3') | Product size (bp) |
|---|---|---|
| 9 | F: TTTCCCTTTACAGTGCAGGA<br>R: GTGCTCTTGTCCAAAATACTC | 253 |
| 10 | F: TTCCTGACCCCGTTTCAATC<br>R: TTGACAATGCTCTTCCCAGG | 193 |
| 11 | F: GTGAACCAGAAGTAAAGGGC<br>R: AGGATCTAGGGAAACCATG | 255 |
| 12 | F: CCCAAAGGAAGAAGAATTTAG<br>R: CCTCTCCTTGCTCCTCTCAG | 297 |
|  | F: CCTAGAAGTATGTCTGTCCTG<br>R: CTCTCCTTGACTAGGATGCTG | 303 |
|  | F: GGATAGGCTTCTTTCAGGGG<br>R: TCCCAAGATGTGTACAGCTC | 392 |

Annealing temperatures were 60° C. for all PCRs except for exon 2 (55° C.).
(F = forward reaction, R = reverse)

These reactions allow amplification of each exon together with at least 50 base pairs of flanking intron sequence. Thus, the primers may be used in diagnostic tests to determine the presence of mutations in the genomic FA(C) gene of a patient. The primer sequences shown in Table 9 are by way of illustration only; other primers may also be used to amplify other portions of the FA(C) gene. Such primers will be oligonucleotides comprising a fragment of sequence from the FA(C) gene (either intron sequence, exon sequence or a sequence spanning an intron-exon boundary) and will preferably be at least 15 nucleotides in length. More preferably, such primers will be of at least 20 nucleotides in length.

In conclusion, these experiments show that the coding region of the FA(C) gene is highly interrupted, containing 14 exons ranging in size from 53–204 base pairs of coding sequence. Thus, in addition to the open reading frame of this gene and as yet undefined upstream and downstream regulatory sequences, the 13 introns provide multiple additional target regions for mutations which might disrupt the function of the gene. The availability of intron sequences from the splice sites and PCR reactions for the amplification of these sequences from genomic DNA will permit the analysis of these regions for potential splice site mutations. Furthermore, with the provision of the FA(C) intron sequence information the analysis of a large and as yet untapped source of patient material for mutations will now be possible using methods such as chemical cleavage of mismatches (Cotton et al., 1988; Montandon et al., 1989 which references are herein incorporated by reference) and single-strand conformational polymorphism analysis (Orita et al., 1989, herein incorporated by reference). The efficiency of these methods will permit an alternative method of classification of FA patients by classical complementation analysis described in Example 8. These molecular-genetic methods, including those described above and others set forth in Example 11, will likely provide a more rapid method of diagnosis than complementation tests.

Additional experiments may now be performed to identify and characterize regulatory elements flanking the FA(C) gene. These regulatory elements may be characterized by standard techniques including deletion analyses wherein successive nucleotides of a putative regulatory region are removed and the effect of the deletions are studied by either transient or long-term expression analyses experiments. The identification and characterization of regulatory elements flanking the genomic FA(C) gene may be made by functional experimentation (deletion analyses, etc.) in mammalian cells by either transient or long-term expression analyses as described in Example 9.

Having provided a genomic clone for the FA(C) gene, it will be apparent to one skilled in the art that either the genomic clone or the cDNA or sequences derived from these clones may be utilized in applications of this invention, including but not limited to, studies of the expression of the FA(C) gene, studies of the function of the FACC protein, the generation of antibodies to the FACC protein diagnosis of FA(C) sufferers and carriers and therapy of FA(C). Descriptions of applications describing the use of FACC cDNA are therefore intended to comprehend the use of the genomic FA(C) gene. It will also be apparent to one skilled in the art that homologs of this gene may now be cloned from other species, such as the mouse, by standard cloning methods. An example of this is presented in Example 14. Such homologs will be useful in the production of animal models of Fanconi Anemia.

EXAMPLE 7

Determination of Complementation Group

The provision herein of a cDNA clone corresponding to the FA(C) gene now enables for the first time a method for determining if FA sufferers have FA attributable specifically to FA complementation group C. Essentially, lymphoblasts derived from patients are transfected with the FACC cDNA, and the sensitivity of the transfected cells to the DNA cross-linking agents DEB and MMC is determined as described above. A decreased sensitivity of the cells to these agents relative to untransfected lymphocytes from the same patient indicates that the FA mutation of the patient is attributable specifically to FA complementation group C. If the sensitivity of the transfected lymphocytes is unaltered relative to the non-transfected control lymphocytes, then the patient is diagnosed as suffering from FA attributable to a complementation group other than group C.

EXAMPLE 8

Nucleotide Sequence Variants of FACC cDNA and Amino Acid Sequence Variants of FACC Protein FIG. 6 shows the nucleotide sequences of the three FACC cDNAs and the amino acid sequence of the FACC protein which is encoded by these cDNAs. It is concluded that the functional characteristic of the FACC protein is its ability to complement the hypersensitivity of FA(C) cells to DNA cross-linking agents. This protein is also encoded in the genomic FA(C) gene provided in Example 6. Having presented the nucleotide and the amino acid sequence of the FACC protein, this invention now also facilitates the creation of DNA molecules, and thereby proteins, which are derived from those disclosed but which vary in their precise nucleotide or amino acid sequence from those disclosed. Such variants may be obtained through a combination of standard molecular biology laboratory techniques and the nucleotide sequence information disclosed by this invention.

Variant DNA molecules include those created by standard DNA mutagenesis techniques, for example, M13 primer mutagenesis. Details of these techniques are provided in Sambrook et al. (1989), Ch. 15. By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the FACC protein are comprehended by this invention. Also within the scope of this invention are small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of an FACC cDNA molecule or the FA(C) gene and, for the purposes of PCR, will comprise at least a 10–15 nucleotide sequence and, more preferably, a 15–30 nucleotide sequence of the FACC cDNA or the FA(C) gene. DNA molecules and nucleotide sequences which are derived from the disclosed DNA molecules as described above may also be defined as DNA sequences which hybridize under stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the Na$^+$ concentration) of the hybridization buffer will determine the stringency of hybridization. Calculations regarding hybridization conditions required for attaining particular degrees of stringency are discussed by Sambrook et al. (1989), chapters 9 and 11, herein incorporated by reference. By way of illustration only, a hybridization experiment may be performed by hybridization of a DNA molecule (for example, a deviation of the FACC cDNA) to a target DNA molecule (for example, the FACC cDNA) which has been electrophoresed in an agarose gel and transferred to a nitrocellulose membrane by Southern blotting (Southern, 1975), a technique well known in the art and described in (Sambrook et al., 1989). Hybridization with a target probe labeled with [$^{32}$P]-dCTP is generally carried out in a solution of high ionic strength such as 6×SSC at a temperature that is 20°–25° C. below the melting temperature, $T_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to 10$^9$ CPM/μg or greater). Following hybridization, the nitrocellulose filter is washed to remove background hybridization. The washing conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton and McCarthy, 1962):

$$T_m = 81.5° C. - 16.6(\log_{10}[Na^+]) + 0.41(\%G+C) - 0.63(\% \text{ formamide}) - (600/l)$$

Where l=the length of the hybrid in base pairs. This equation is valid for concentrations of Na$^+$ in the range of 0.01M to 0.4M, and it is less accurate for calculations of $T_m$ in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., 1989).

Thus, by way of example, for a 150 base pair DNA probe derived from the first 150 base pairs of the open reading frame of the FACC cDNA (with a % GC=45%), a calculation of hybridization conditions required to give particular stringencies may be made as follows:

For this example, it is assumed that the filter will be washed in 0.3×SSC solution following hybridization, thereby

[Na$^+$]=0.045M

% GC=45%

Formamide concentration=0 l=150 base pairs $$T_m = 81.5 - 16(\log_{10}[Na^+]) + (0.41 \times 45) - \frac{(600}{150)}$$

and so $T_m$=74.4° C.

The $T_m$ of double-stranded DNA decreases by 1°–1.5° C. with every 1% decrease in homology (Bonner et al., 1973). Therefore, for this given example, washing the filter in 0.3×SSC at 59.4°–64.4° C. will produce a stringency of hybridization equivalent to 90%; that is, DNA molecules with more than 10% sequence variation relative to the target FACC cDNA will not hybridize. Alternatively, washing the hybridized filter in 0.3×SSC at a temperature of 65.4°–68.4° C. will yield a hybridization stringency of 94%; that is, DNA molecules with more than 6% sequence variation relative to the target FACC cDNA molecule will not hybridize. The above example is given entirely by way of theoretical illustration. One skilled in the art will appreciate that other hybridization techniques may be utilized and that variations in experimental conditions will necessitate alternative calculations for stringency.

In preferred embodiments of the present invention, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. In a most preferred embodiment, stringent conditions are those under which DNA sequences with more than 6% mismatch will not hybridize.

The degeneracy of the genetic code further widens the scope of the present invention as it enables major variations in the nucleotide sequence of a DNA molecule while maintaining the amine acid sequence of the encoded protein. For example, the second amine acid residue of the FACC protein is alanine. This is encoded in the FACC cDNA by the nucleotide codon triplet GCT. Because of the degeneracy of the genetic code, three other nucleotide codon triplets—GCT, GCC and GCA—also code for alanine. Thus, the nucleotide sequence of the FACC cDNA could be changed at this position to any of these three codons without affecting the amine acid composition of the encoded protein or the characteristics of the protein. The genetic code and variations in nucleotide codons for particular amine acids is presented in Tables 10-A and 10-B. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein T comprehended by this invention.

TABLE 10-A

The Genetic Code

| First Position | Second Position | | | | Third Position |
|---|---|---|---|---|---|
| (5' end) T | C | A | | G | (3' end) |
| T  Phe | Ser | Tyr | | Cys | T |
|    Phe | Ser | Tyr | | Cys | C |

TABLE 10-A-continued

The Genetic Code

| First Position (5' end) | Second Position | | | | Third Position (3' end) |
|---|---|---|---|---|---|
| | T | C | A | G | |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"Stop (och)" stands for the ocre termination triplet, and "Stop (amb)" for the amber. ATG is the most common initiator codon; GTG usually codes for valine, but it can also code for methionine to initiate an mRNA chain.

TABLE 10-B

The Degeneracy of the Genetic Code

| Number of Synonymous Codons | Amino Acid | Total Number of Codons |
|---|---|---|
| 6 | Leu, Ser, Arg | 18 |
| 4 | Gly, Pro, Ala, Val, Thr | 20 |
| 3 | Ile | 3 |
| 2 | Phe, Tyr, Cys, His, Gln, Glu, Asn, Asp, Lys | 18 |
| 1 | Met, Trp | 2 |
| Total number of codons for amino acids | | 61 |
| Number of codons for termination | | 3 |
| Total number of codons in genetic code | | 64 |

One skilled in the art will recognize that the DNA mutagenesis techniques described above may be used not only to produce variant DNA molecules, but will also facilitate the production of proteins which differ in certain structural aspects from the FACC protein, yet which proteins are clearly derivative of this protein and which maintain the essential characteristics of the FACC protein. Newly derived proteins may also be selected in order to obtain variations on the characteristic of the FACC protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure (EP 75,444A).

Substitutional variants are those in which at least one residue in the amino acid sequence has been removed and a different residue inserted in its place. Such substitutions generally are made in accordance with the following Table 11 when it is desired to finely modulate the characteristics of the protein. Table 11 shows amino acids which may be substituted for an original amino acid in a protein and which are regarded as conservative substitutions.

TABLE 11

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 11, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the FACC protein by analyzing the ability of the derivative proteins to complement the sensitivity to DNA cross-linking agents exhibited by FA(C) cells. These assays may be performed by transfecting DNA molecules encoding the derivative proteins into FA(C) cells as described above.

The FA(C) gene, FACC cDNA, DNA molecules derived therefrom and the protein encoded by the cDNA and derivative DNA molecules may be utilized in aspects of both the study of FA and for diagnostic and therapeutic applications related to FA. Utilities of the present invention include, but are not limited to, those utilities described in the examples

EXAMPLE 9

Expression of FACC cDNA Sequences

With the provision of the FACC cDNA, the expression and purification of the FACC protein by standard laboratory techniques is now enabled. The purified protein may be used for function analyses, antibody production and patient therapy. Furthermore, the DNA sequence of the FACC cDNA and the mutant FACC cDNAs isolated from FA(C) patients as disclosed in Example 3 can be manipulated in studies to understand the expression of the gene and the function of its product. In this way, the underlying biochemical defect which results in the symptoms of FA(C) can be established. The mutant versions of the FACC cDNA isolated to date and others which may be isolated based upon information contained herein, may be studied in order to detect alteration in expression patterns in terms of relative quantities, tissue specificity and functional properties of the encoded mutant FACC protein. Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to FACC proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in *E. coli* in large amounts for functional studies. Methods and plasmid vectors for producing fusion proteins and intact native proteins in bacteria are described in Sambrook et al. (1989) (ch. 17, herein incorporated by reference). Such fusion proteins may be made in large amounts, are easy to purify, and can be used to elicit antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (1989) and are well known in the art. Often, proteins expressed at high levels are found in insoluble inclusion bodies. Methods for extracting proteins from these aggregates are described by Sambrook et al. (1989) (ch. 17). Vector systems suitable for the expression of lacZ fusion genes include the pUR series of vectors (Ruther and Muller-Hill, 1983), pEX1-3 (Stanley and Luzio, 1984) and pMR100 (Gray et al., 1982). Vectors suitable for the production of intact native proteins include pKC30 (Shimatake and Rosenberg, 1981), pKK177-3 (Amann and Brosius, 1985) and pET-3 (Studiar and Moffatt, 1986). FACC fusion proteins may be isolated from protein gels, lyophilized, ground into a powder and used as an antigen. The DNA sequence can also be transferred from its existing context in pREP4 to other cloning vehicles, such as other plasmids, bacteriophages, cosmids, animal viruses and yeast artificial chromosomes (YACs) (Burke et al., 1987). These vectors may then be introduced into a variety of hosts including somatic cells, and simple or complex organisms, such as bacteria, fungi (Timberlake and Marshall, 1989), invertebrates, plants (Gasser and Fraley, 1989), and pigs (Pursel et al., 1989), which cell or organisms are rendered transgenic by the introduction of the heterologous FACC cDNA.

For expression in mammalian cells, the cDNA sequence may be ligated to heterologous promoters, such as the simian virus (SV)40, promoter in the pSV2 vector (Mulligan and Berg, 1981), and introduced into cells, such as monkey COS-1 cells (Gluzman, 1981), to achieve transient or long-term expression. The stable integration of the chimeric gene construct may be maintained in mammalian cells by biochemical selection, such as neomycin (Southern and Berg, 1982) and mycophoenolic acid (Mulligan and Berg, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) is introduced into eukaryotic expression vectors by conventional techniques. These vectors are designed to permit the transcription of the cDNA eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., 1981; Gorman et al., 1982), and indeed the pREP4 vector (Groger et al., 1989) described in Example 2 is an example of such vectors. The level of expression of the cDNA can be manipulated with this type of vector, either by using promoters that have different activities (for example, the baculovirus pAC373 can express cDNAs at high levels in *S. frugiperda* cells (Summers and Smith, 1985) or by using vectors that contain promoters amenable to modulation, for example, the glucocorticoid-responsive promoter from the mouse mammary tumor virus (Lee et al., 1982). The expression of the cDNA can be monitored in the recipient cells 24 to 72 hours after introduction (transient expression).

In addition, some vectors contain selectable markers such as the gpt (Mulligan and Berg, 1981) or neo (Southern and Berg, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., 1981) or Epstein-Barr (Sugden et al., 1985). Such episomal vectors are exemplified by the pREP4 Epstein-Barr virus vector in which the cDNA library described in Example 2 herein was constructed. Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., 1978).

The transfer of DNA into eukaryotic, in particular human or other mammalian cells, is now a conventional technique.

The vectors are introduced into the recipient cells as pure DNA (transfection) by, for example, precipitation with calcium phosphate (Graham and vander Eb, 1973) or strontium phosphate (Brash et al., 1987), electroporation (Neumann et al., 1982), lipofection (Felgner et al., 1987), DEAE dextran (McCuthan et al., 1968), microinjection (Mueller et al., 1978), protoplast fusion (Schafner, 1980), or pellet guns (Klein et al., 1987). Alternatively, the cDNA can be introduced by infection with virus vectors. Systems are developed that use, for example, retroviruses (Bernstein et al., 1985), adenoviruses (Ahmad et al., 1986), or Herpes virus (Spaete et al., 1982).

These eukaryotic expression systems can be used for studies of the FA(C) gene and mutant forms of this gene, the FACC protein and mutant forms of this protein. Such uses include, for example, the identification of regulatory elements located in the 5' region of the FA(C) gene on genomic clones that can be isolated from human genomic DNA libraries using the information contained in the present invention and described in Example 7. The eukaryotic expression systems may also be used to study the function of the normal complete protein, specific portions of the protein, or of naturally occurring or artificially produced mutant proteins. Naturally occurring mutant proteins exist in patients with FA, while artificially produced mutant proteins can be designed by site directed mutagenesis as described above. These latter studies may probe the function of any desired amino acid residue in the protein by mutating the nucleotide coding for that amino acid.

Using the above techniques, the expression vectors containing the FA gene sequence or fragments or variants or mutants thereof can be introduced into human cells, mammalian cells from other species or non-mammalian cells as desired. The choice of cell is determined by the purpose of the treatment. For example, monkey COS cells (Gluzman, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts (as described herein) may be used.

The following is provided as one exemplary method to express FACC polypeptide from the cloned FACC cDNA sequences in mammalian cells. Cloning vector pXT1, commercially available from Stratagene, contains the Long Terminal Repeats (LTRs) and a portion of the GAG gene from Moloney Murine Leukemia Virus. The position of the viral LTRs allows highly efficient, stable transfection of the region within the LTRs. The vector also contains the Herpes Simplex Thymidine Kinase promoter (TK), active in embryohal cells and in a wide variety of tissues in mice, and a selectable neomycin gene conferring G418 resistance. Two unique restriction sites BglII and XhoI are directly downstream from the TK promoter. FACC cDNA, including the entire open reading frame for the FACC protein and the 3' untranslated region of the cDNA is cloned into one of the two unique restriction sites downstream from the promoter.

The ligated product is transfected into mouse NIH 3T3 cells using Lipofectin (Life Technologies, Inc.) under conditions outlined in the product specification. Positive transfectants are selected after growing the transfected cells in 600 µg/ml G418 (Sigma, St. Louis, Mo.). The protein is released into the supernatant and may be purified by standard immunoaffinity chromatography techniques using antibodies raised against the FACC protein, as described below.

Expression of the FACC protein in eukaryotic cells may also be used as a source of proteins to raise antibodies. The FACC protein may be extracted following release of the protein into the supernatant as described above, or, the cDNA sequence may be incorporated into a eukaryotic expression vector and expressed as a chimeric protein with, for example, β-globin. Antibody to β-globin is thereafter used to purify the chimeric protein. Corresponding protease cleavage sites engineered between the β-globin gene and the cDNA are then used to separate the two polypeptide fragments from one another after translation. One useful expression vector for generating β-globin chimeric proteins is pSG5 (Stratagene). This vector encodes rabbit β-globin.

The recombinant cloning vector, according to this invention, then comprises the selected DNA of the DNA sequences of this invention for expression in a suitable host. The DNA is operatively linked in the vector to an expression control sequence in the recombinant DNA molecule so that the FACC polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this invention, may be selected from the group consisting of *E. coli*, Pseudomonas, *Bacillus subtilis*, *Bacillus stearothermophilus* or other bacilli; other bacteria; yeast; fungi; insect; mouse or other animal; or plant hosts; or human tissue cells.

It is appreciated that for mutant or variant DNA sequences, similar systems are employed to express and produce the mutant product.

EXAMPLE 10

Production of an Antibody to FACC Protein

Monoclonal or polyclonal antibodies may be produced to either the normal FACC protein or mutant forms of this protein. Optimally, antibodies raised against the FACC protein would specifically detect the FACC protein. That is, such antibodies would recognize and bind the FACC protein and would not substantially recognize or bind to other proteins found in human cells. The determination that an antibody specifically detects the FACC protein is made by any one of a number of standard immunoassay methods; for instance, the Western blotting technique (Sambrook et al., 1989). To determine that a given antibody preparation (such as one produced in a mouse) specifically detects the FACC protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the FACC protein will, by this technique, be shown to bind to the FACC protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-FACC protein binding.

Substantially pure FACC protein suitable for use as an immunogen is isolated from the transfected or transformed cells as described in Example 7 above. Concentration of protein in the final preparation is adjusted, for example, by concentration on an Amicon filter device, to the level of a few micrograms per milliliter. Monoclonal or polyclonal antibody to the protein can then be prepared as follows:

A. Monoclonal Antibody Production by Hybridoma Fusion.

Monoclonal antibody to epitopes of the FACC protein identified and isolated as described can be prepared from murine hybridomas according to the classical method of Kohler and Milstein (1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use. Detailed procedures for monoclonal antibody production are described in Harlow and Lane (1988).

B. Polyclonal Antibody Production by Immunization.

Polyclonal antiserum containing antibodies to hererogenous epitopes of a single protein can be prepared by immunizing suitable animals with the expressed protein (Example 9), which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (1973). Plateau concentration of antibody is usually in the range of 0.1 to 0.2 mg/ml of serum (about 12 μM). Affinity of the antisera for the antigen is determined by preparing competitive binding curves, as described, for example, by Fisher (1980).

C. Antibodies Raised against Synthetic Peptides.

A third approach to raising antibodies against the FACC protein is to use synthetic peptides synthesized on a commercially available peptide synthesizer based upon the predicted amino acid sequence of the FACC protein.

D. Antibodies Raised by Injection of FA(C) Gene.

Antibodies may be raised against the FACC protein by subcutaneous injection of a DNA vector which expresses the FACC protein into laboratory animals, such as mice. Delivery of the recombinant vector into the animals may be achieved using a hand-held form of the Biolistic system (Sanford et al., 1987) as described by Tang et al. (1992). Expression vectors suitable for this purpose may include those which express the FA(C) gene under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample.

EXAMPLE 11

DNA-Based Diagnosis

One major application of the FACC cDNA and FA(C) gene intron/exon boundary sequence information presented herein is in the area of genetic testing, carrier detection and prenatal diagnosia for FA(C). Individuals carrying mutations in the FA(C) gene (disease carrier or patients) may be detected at the DNA level with the use of a variety of techniques. For such a diagnostic procedure, a biological sample of the subject, which biological sample contains either DNA or RNA derived from the subject, is assayed for the presence of a mutant FA(C) gene. Suitable biological samples include samples containing genomic DNA or RNA obtained from body cells, such as those present in peripheral blood, urine, saliva, tissue biopsy, surgical specimen, amniocentesis samples and autopsy material. The detection in the biological sample of either a mutant FA(C) gene or a mutant FA(C) RNA may be performed by a number of methodologies, as outlined below.

A preferred embodiment of such detection techniques is the polymerase chain reaction amplification of reverse transcribed RNA (RT-PCR) of RNA isolated from lymphocytes followed by direct DNA sequence determination of the products. This approach is described in Example 3 above. The presence of one or more nucleotide difference between the obtained sequence and the cDNA sequences presented in FIG. 6, and especially, differences in the ORF portion of the nucleotide sequence are taken as indicative of a potential FA(C) gene mutation. The effect of such nucleotide differences may be determined by engineering the nucleotide differences into the FACC cDNA by transfecting the altered cDNA into HSC536N cells. Transfected cells are then examined for their sensitivity to DEB and MMC. If the cells show the same sensitivity to those agents as non-FA cells (i.e., the altered cDNA complements the FA(C) mutation), then the observed nucleotide differences are regarded as "neutral," and the patient is not classified as an FA(C) carrier or sufferer on the basis of this nucleotide difference. On the other hand, if the altered cDNA does not complement the sensitivity of the cells to the mutagenic agents, the nucleotide difference is regarded as a mutation rather than a natural difference, and the patient is classified as an FA(C) sufferer or carrier.

Because of the diploid nature of the human genome, both copies of the FA(C) gene need to be examined to distinguish between FA(C) carriers and FA(C) sufferers. If a single copy of the FA(C) gene is found to be mutated and the other copy is "normal," then the subject is classified as an FA(C) carrier or heterozygote. If both copies of the FA(C) gene are found to be mutated and do not complement the DEB hypersensitivity of HSC536N cells, then the subject is classified as an FA(C) sufferer.

Alternatively, DNA extracted from lymphocytes or other cells may be used directly for amplification. The direct amplification from genomic DNA would be appropriate for analysis of the entire FA(C) gene including regulatory sequences located upstream and downstream from the open reading frame. Recent reviews of direct DNA diagnosis have been presented by Caskey (1987) and by Landegren et al. (1988).

Further studies of FA(C) genes isolated from FA(C) patients may reveal particular mutations which occur at a high frequency within this population of individuals. In this case, rather than sequencing the entire FA(C) gene, it may be possible to design DNA diagnostic methods to specifically detect the most common FA(C) mutations.

The detection of specific DNA mutations may be achieved by methods such as hybridization using specific oligonucleotides (Wallace et al., 1986), direct DNA sequencing (Church and Gilbert, 1988), the use of restriction enzymes (Flavell et al., 1978; Geever et al., 1981), discrimination on the basis of electrophoretic mobility in gels with denaturing reagent (Myers and Maniatis, 1986), RNase protection (Myers et al., 1985), chemical cleavage (Cotton et al., 1985), and the ligase-mediated detection procedure (Landegren et al., 1988).

Oligonucleotides specific to normal or mutant sequences are chemically synthesized using commercially available machines, labelled radioactively with isotopes (such as $^{32}P$) or non-radioactively (with tags such as biotin (Ward and Langer et al., 1981), and hybridized to individual DNA samples immobilized on membranes or other solid supports by dot-blot or transfer from gels after electrophoresis. The presence or absence of these specific sequences are visualized by methods such as autoradiography or fluorometric (Landegren, et al., 1989) or colorimetric reactions (Gebeyehu et al., 1987).

Sequence differences between normal and mutant forms of that gene may also be revealed by the direct DNA sequencing method of Church and Gilbert (1988). Cloned DNA segments may be used as probes to detect specific DNA segments. The sensitivity of this method is greatly enhanced when combined with PCR (Wrichnik et al., 1987; Wong et al., 1987; Stoflet et al., 1988). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags.

Sequence alterations may occasionally generate fortuitous restriction enzyme recognition sites or may eliminate existing restriction sites. Changes in restriction sites are revealed by the use of appropriate enzyme digestion followed by conventional gel-blot hybridization (Southern, 1975). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

Genetic testing based on DNA sequence differences may be achieved by detection of alteration in electrophoretic mobility of DNA fragments in gels with or without denaturing reagent. Small sequence deletions and insertions can be visualized by high-resolution gel electrophoresis. For example, a PCR product with small deletions is clearly distinguishable from a normal sequence on an 8% non-denaturing polyacrylamide gel (WO 91/10734, [Nagamine et al., 1989]). DNA fragments of different sequence compositions may be distinguished on denaturing formamide gradient gels in which the mobilities of different DNA fragments are retarded in the gel at different positions according to their specific "partial-melting" temperatures (Myers et al., 1985). Alternatively, a method of detecting a mutation comprising a single base substitution or other small change could be based on differential primer length in a PCR. For example, an invariant primer could be used in addition to a primer specific for a mutation. The PCR products of the normal and mutant genes can then be differentially detected in acrylamide gels.

In addition to conventional gel-electrophoresis and blot-hybridization methods, DNA fragments may also be visualized by methods where the individual DNA samples are not immobilized on membranes. The probe and target sequences may be both in solution, or the probe sequence may be immobilized (Saiki et al., 1989). A variety of detection methods, such as autoradiography involving radioisotopes, direct detection of radioactive decay (in the presence or absence of scintillant), spectrophotometry involving calorigenic reactions and fluorometry involved fluorogenic reactions, may be used to identify specific individual genotypes.

If more than one mutation is frequently encountered in the FA(C) gene, a system capable of detecting such multiple mutations would be desirable. For example, a PCR with multiple, specific oligonucleotide primers and hybridization probes may be used to identify all possible mutations at the same time (Chamberlain et al., 1988). The procedure may involve immobilized sequence-specific oligonucleotides probes (Saiki et al., 1989).

EXAMPLE 12

Quantitation of FACC Protein

An alternative method of diagnosing FA(C) sufferers or FA(C) carrier status may be to quantitate the level of FACC protein in the cells of an individual. This diagnostic tool would be useful for detecting reduced levels of the FACC protein which result from, for example, mutations in the promoter regions of the FA(C) gene or mutations within the coding region of the gene which produced truncated, non-functional polypeptides. The determination of reduced FACC protein levels would be an alternative or supplemental approach to the direct determination of FA status by nucleotide sequence determination outlined above. The availability of antibodies specific to the FACC protein would allow the quantitation of cellular FACC protein by one of a number of immunoassay methods which are well known in the art and are presented in Harlow and Lane (1988).

For the purposes of quantitating the FACC protein, a biological sample of the subject, which sample includes cellular proteins, is required. Such a biological sample may be obtained from body cells, such as those present in peripheral blood, urine, saliva, tissue biopsy, amniocentesis samples, surgical specimens and autopsy material. Quantitation of FACC protein would be made by immunoassay and compared to levels of the protein found in non-FA human cells. A significant (preferably 50% or greater) reduction in th& amount of FACC protein in the cells of a subject compared to the amount of FACC protein found in non-FA human cells would be taken as an indication that the subject may be an FA sufferer or FA carrier.

EXAMPLE 13

Gene Therapy

The death of FA sufferers usually results from one or more conditions arising from hematopoietic failure. Bone marrow transplantation (BMT) may be performed in order to treat this problem; however, the lack of a suitable donor may prevent this course of treatment and conventional BMT is still associated with potentially fatal risks (Ebell et al., 1989), many arising from the risk of transplant rejection and the immunosuppression regimes required to minimize this risk. An improved gene therapy approach to BMT for FA(C) patients is now made possible by the present work. Essentially, bone marrow cells may be removed from an FA patient and transfected with an expression vector containing the FACC cDNA. These transfected bone marrow cells will thereby produce functional FACC protein and can be reintroduced into the patient without concern of rejection.

The scientific and medical procedures required for this approach—bone marrow transplantation and human cell transfection—are now routine procedures. The provision herein of FACC cDNAs now allows the development of human gene therapy based upon these procedures. Immunotherapy of melanoma patients using genetically engineered tumor-infiltrating lymphocytes (TILs) has been reported by Rosenberg et al. (1990). In that study, a retrovirus vector was used to introduce a gene for neomycin resistance into TILs. A similar approach may be used to introduce the FACC cDNA into bone marrow cells of FA(C) patients.

Retroviruses have been considered the preferred vector for experiments in gene therapy, with a high efficiency of infection and stable integration and expression (Orkin et al., 1988). The full length FA gene or cDNA can be cloned into a retroviral vector and driven from either its endogenous promoter or from the retrovital LTR (long terminal repeat). Expression of levels of the normal protein as low as 10% of the endogenous mutant protein in FA(C) patients would be expected to be beneficial, since this is a recessive disease. Other viral transfection systems may also be utilized for this type of approach, including Adeno-Associated virus (AAV) (McLaughlin et al., 1988), Vaccinia virus (Moss et al., 1987), Bovine Papilloma virus (Rasmussen et al., 1987) or members of the herpesvirus group such as Epstein-Barr virus (Margolskee et al., 1988).

EXAMPLE 14

Cloning and Analysis of the Murine Fanconi Anemia Group C cDNA

Two million clones from a mouse liver cDNA library constructed in the vector Lambda DASH (Stratagene, LaJolla, Calif.) were screened with a 1131 base pair fragment from the human FACC cDNA encompassing bases 1108 to 2239 of the sequence shown in FIG. 6. Hybridization was performed under moderate stringency at 37° C. in a solution containing 50% formamide, 6×SSC and a final wash at 60° C. in 1×SSC, 0.1% SDS. Three positive bacteriophage clones were plaque purified and the inserts clones into pBluescript (Stratagene, LaJolla, Calif.) using the in vivo excision protocol recommended by the manufacturer. Random primed $^{32}$P- labelling, plasmid propagation and purification, restriction enzyme analysis, DNA sequencing, and subcloning were performed according to standard protocols (Sambrook et al., 1989). The three clones were named as pmfac2, pmfac6 and pmfac7.

Figure 10:
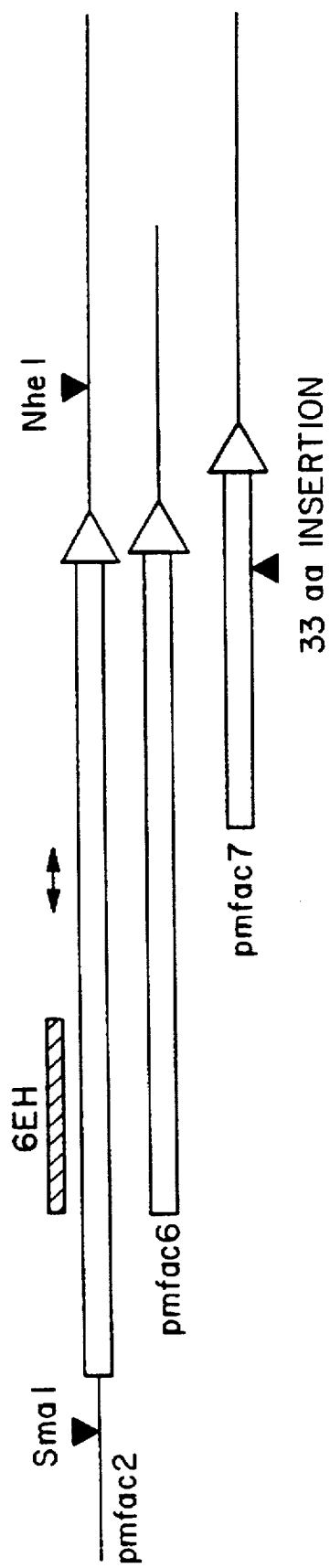
FIG. 10 shows maps of the three mouse liver cDNAs (pmfac2, pmfac6 and pmfac7) which were isolated with a human FACC probe. The unfilled arrows indicate the open reading frame. The filled arrowhead on pmfac7 indicates the position of a 33 amino acid insertion in this clone. The Sma I and Nhe I sites were used to subclone the putative cloning region into the pREP4 expression vector.

Restriction maps of the three clones were found to overlap in part as shown in FIG. 10.

The cDNA clones were sequenced and the mouse and human sequences compared at the nucleotide and protein level. The sequence of pmfac2 is shown in FIG. 11 with the putative open reading frame shown underneath. The full length pmfac2 contains an open reading frame of 558 amino acids, the same length as the human FACC cDNA coding sequence. In addition, one of the clones (pmfac7) contains an additional 99 base pair region inserted at nucleotide 1849, resulting in an open reading frame of 591 amino acids. This sequence is shown in FIG. 12. The 99 base pair insertion in pmfac7 does not change the open reading frame of the protein and is likely to be an alternatively spliced exon. Clone pmfac6 was found to contain a shorter 3' untranslated region ending at an alternative polyadenylation site at position 2515 in FIG. 11. (The polyadenylation sites are underlined in FIG. 11.)

Figure 15:
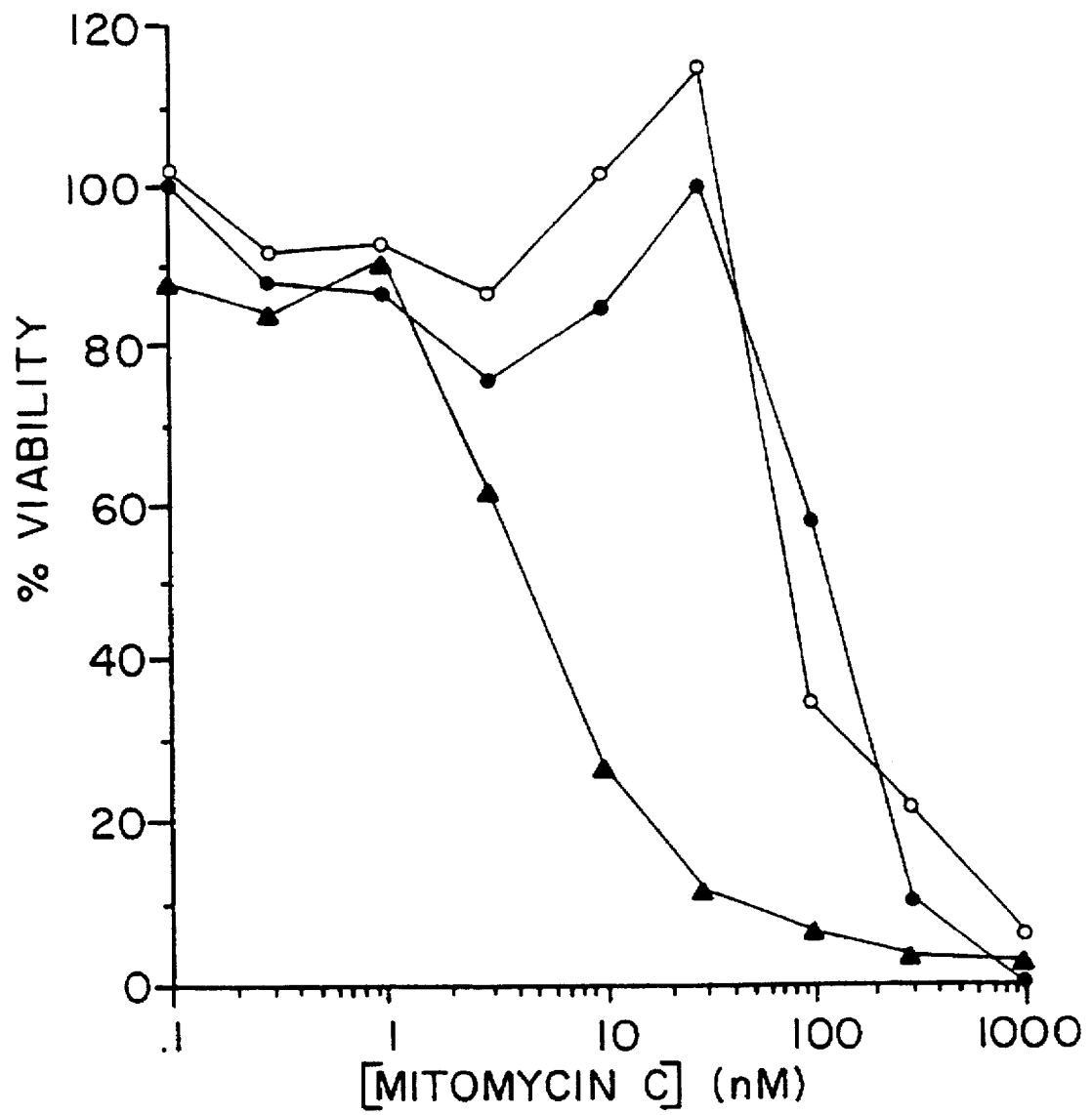
FIG. 15 is a graph showing complementation of the MMC sensitive phenotype of human FA(C) cells by the murine cDNA. The graph shows viability of FA(C) cells transfected with the mouse cDNA (●), untransfected FA(C) cells (▲) and normal cells (o).

Only pmfac 2 contains any 5' untranslated region (UTR). These 5' UTR sequences are more similar to exon 1 than to exon 1A of the human pFAC clones. The alignment of the 5' UTR of pmfac2 to exon 1 is shown in FIG. 15. The similarity between exon 1 and the homologous region in the murine clone is approximately 75% whereas the similarity between the untranslated region of the exon immediately preceding the start site of translation and the homologous murine region is approximately 61% (including the large gap as a single mismatch). The human clone contains an additional 17 base pairs of 5' sequence.

FIG. 15 shows a comparison of the theoretical protein sequences derived from the human and mouse cDNAs. The amino acid sequences of the two proteins are 67% identical to each other, with 79% similarity including conservative changes. There are no obvious regions of higher conservation, although there is one region (amino acids 474–486) that is not conserved at all between the two sequences. This region is identical in all three mouse clones and is not flanked by splice sites so it is unlikely to be an alternatively spliced exon. The leucine residue mutated to proline (L554P) in the FA cell line HSC536N is conserved in the mouse.

The genomic gene from which the mouse Facc cDNA was derived may now be cloned from a mouse genomic library using regions of either the human FACC cDNA or the mouse Facc cDNA as probes to protect hybridizing clones. Mouse genomic libraries which are screened for these clones may be purchased commerically or may be constructed in the laboratory. Suitable examples of commercial libraries include the mouse genomic libraries established in the bacteriophage lambda EMBL3 vector available from Clontech, Palo Alto, Calif. and the mouse genomic libraries established in the pWE15 and Supercos 1 vectors available from Stratagene, LaJolla, Calif. Libraries of mouse genomic DNA made in yeast artifical chromosomes (YACs) as described in Example 6 for the human genomic gene may also be utilized. YAC vectors offer the advantage of being able to carry much larger genomic fragments than conventional bacteriophage vectors, significantly increasing the likelihood of obtaining a large gene intact.

The methodology described for cloning the human genomic FA(C) gene described in Example 6 may be followed for the cloning of the mouse gene. Other suitable methods for cloning the mouse genomic gene are available and are well known in the art. Methods for labelling fragments of the mouse or human cDNA for use as a probe and for screening such libraries are widely known, and the detailed methodologies are presented in Sambrook et al. (1989). Following the isolation of hybridizing genomic DNA clones, the clones are analyzed by methods including restriction mapping and DNA sequence analysis to determine the extent of the mouse genomic FA(C) gene. The complete gene may need to be assembled from several individual clones if it is of large size. Additional internal or terminal sequences not present in the assembled gene may be obtained by reprobing the library using probes derived from regions adjacent to the missing sequences. Alternatively, polymerase chain reaction (PCR) based methods such as inverse PCR and ligation mediated PCR may be used to amplify and clone the missing sequences from total mouse DNA. The identification and characterization of regulatory elements flanking the mouse genomic FA(C) gene may be made by methods similar to those described in Example 6 for the human genomic gene.

EXAMPLE 15

Confirmation that the Mouse cDNA is the True Homolog of the Human FACC cDNA

To confirm the identity of pmfac2 as the homolog of the human FACC cDNA rather than a related gene, experiments were performed to determine whether pmfac2 was capable of complementing the sensitivity to MMC of FA group C cells. A 1954 base pair fragment of pmfac2 comprising nucleotides 254 to 2208 defined by the SmaI-NheI restriction fragment as shown in FIG. 10 was subcloned in the appropriate orientation for expression of the encoded protein into the polylinker of the eukaryotic expression vector pREP4 to create the plasmid pREPmfac. pREPmfac therefore includes the entire open reading frame from pmfac2. pREPmfac was transfected into HSC536N cells (the FA group C cell line) essentially as described in Example I. Briefly, 40 μg of pREPmfac was transfected into HSC536N using Lipofectin and the presence of the plasmid was selected by growth in hygromycin. The resulting pool of transfected cells was subcultured in concentrations of MMC ranging from 0.1 nM to 1000 nM and the dose response curve compared to untransfected HSC536n lymphoblasts and to normal lymphoblasts (HSC93). Cell viability was assayed as described in Example I and $EC_{50}$ data were determined directly from the viability plot. The results of these experiments are shown in FIG. 15. The experiments confirm that HSC536N cells are MMC sensitive, with an $Ec_{50}$ of 5 nM (closed triangles in FIG. 15), while the HSC536N cells expressing the mouse Facc cDNA (closed circles in FIG. 15) exhibited an elevated resistance to the MMC compared to untransfected HSC536N cells. The normal lymphoblast cell line HSC93 cells (open circles in FIG. 15) demonstrated an $Ec_{50}$ of 134 nM whereas HSC536N cells transfected with pREPmfac demonstrated an $EC_{50}$ of 87 nM. Thus, the murine Facc cDNA is capable of correcting the MMC sensitive phenotype of FA group C cells.

EXAMPLE 16

Cross-Species Hybridization

A cross-species Southern blot hybridization experiment was performed to determine whether homologs of the FA gene were conserved throughout evolution. A 376 base pair subclone from the mouse cDNA was used as a probe in these experiments. This subclone is shown on FIG. 10 as the hatched box 6EH; the fragment extended from position 720 to position 1096 of pmfac2 as shown in FIG. 11. The labelled fragment was hybridized under low stringency conditions to a Southern blot prepared from EcoRI-digested DNA from multiple species using standard procedures (Sambrook et al., 1989). The hybridization conditions included a hybridization at 55° C. in Church-Gilbert hybridization solution (7% SDS, 0.5M sodium phosphate pH 7.2, 1 mM EDTA and 1% BSA) and a final wash in 1×SSC, 0.1% SDS at 60° C. The autoradiograph was exposed for three days with an intensifying screen (Dupont, Wilmington, Del.). Strong hybridizing fragments were seen in DNA from mouse, rat and human. In addition, cross-hybridizing fragments were seen in chicken and *Drosophila melanogaster* DNA and some hybridization was also detected in salmon DNA. These results indicated the presence of conserved sequences in these species. No signal was seen in *Xenopus laevis* DNA at this hybridization stringency. The specificity of the signal in the mouse DNA at the same stringency under which hybridizing fragments can be detected in other species is a good indication that it will be possible to isolate related clones from these species.

EXAMPLE 17

Tissue and Developmental Specific Expression of the Murine Facc cDNA

The tissue distribution of the expression of the murine Facc gene was determined by amplification of cDNA prepared from tissues of normal adult mice. This approach allows the detection of RNA transcribed from the Facc gene.

Total RNA was prepared from tissues of C57BL/6 mice by guanidine thiocyanate precipitation essentially as described by Sambrook et al. (1989). One μg of RNA was reverse transcribed in the reaction with Moloney murine leukemia virus RNase H- reverse transcriptase (BRL, Gaithersburg, Md.) and random hexamers as primers according to the manufacturer's instructions. Polymerase chain reaction amplification of the first strand cDNA was performed using primers RAC9 (5' TACTAGCTGCTCT-TCAGG 3') and RAC16 (5' AGCATCAGGAGACGGTTG 3') amplifying from positions 1244 to 1682 of the mouse cDNA sequence as shown in FIG. 11. Primer sequences RAC9 end RAC16 are set forth as Seq. I.D. Nos. 72 and 73 in the accompanying sequence listing. The fragment amplified by these primers is also shown by the double headed arrow in FIG. 10. Following an initial denaturation at 96° C. for 5 minutes followed by addition of 0.5 units of Taq polymerase at 72° C., the amplification cycle used was 95° C. for 30 seconds, 50° C. for 30 seconds and 72° C. for one minute. This was repeated for 40 cycles and followed by a final 7 minutes extension as 72° C.

Eight tissues types were analyzed in this manner: liver, small intestine, submucosal gland, brain, lung, heart, spleen and kidney. Amplification product was obtained in all of these tissues, indicating the presence of the murine Facc message in each tissue type.

A Northern blot prepared with RNA from murine LtK cells (available from the American Type Tissue Collection, Rockville, Md., Accession No. ATCC CCL1.3) and probed with the 6EH probe demonstrated that the message is present in moderate abundance in these cells and that both polyadenylation sites (shown underlined in FIGS. 11 and 12 and by the arrowheads in FIG. 10) are used approximately equally. The equal usage of two polyadenylation sites is in contrast to the situation in the human cDNA where the longest of three messages, resulting from three alternative polyadenylation sites is more abundant than the two shorter messages.

EXAMPLE 18

In situ RNA Hybridization

Because developmental defects are a common, although not constant feature of human Fanconi Anemia, the possibility that the murine Facc gene is differentially expressed during mouse development was examined. FA malformations include growth retardation, birth marks, kidney and urinary abnormalities, absence of the radius and/or thumb and microphthalmia and are suggestive of a defect during day 25 to day 35 of human gestation (Gordon-Smith and Rutherford, 1991), corresponding to approximately day 9 to day 11.5 of gestation in the mouse.

Paraffin embedded sections of mouse adult tissues and embryos (NIH Swiss mice) were obtained from Novagen, Inc. (Madison, Wis.). The probe 6EH was labelled with $^{35}$S-UTP by in vitro transcription from the T7 and T3 promoters of pBluescript using a kit from Stratagene. The antisense positive control probe HOX10, which hybridizes to the central nervous system in 12 day mouse embryos (Liu et al., 1992) was labelled in a similar fashion. The slides were dewaxed in three 5 minute changes of xylene and rehydrated through 100%, 100%, 95%, 80%, 50% and 30% ethanol in water, with three minutes in each solution. Thereafter, in situ hybridization was performed essentially as described by Trezise and Buchwald (1991) with a 7.5 minute proteinase K treatment, a hybridization temperature of 52° C. and a final wash at 60° C. Slides were exposed to NTB-2 emulsion in the dark for 2-3 weeks, developed and stained with hematoxylin and eosin.

The examination of adult mouse tissues (heart, kidney, thymus, brain, testis, spleen and intestine) by this in situ RNA hybridization approach revealed a uniform pattern of expression in all cells. In addition, sagittal and parasagittal sections of embryos from days 8-13 also showed a uniform pattern of expression with a somewhat higher level of expression in days 8 and 9 in the head mesenchyme as compared to the rest of the embryo. Higher levels of expression were detected in the developing bones of 14 to 16 day embryos. At this stage, uniform labelling of surrounding tissues similar to the labelling in adult tissues was seen, but the perichondrium of developing bone was observed to be more heavily labelled, as was the region surrounding the whisker hair follicles. For example, a positive signal was detected in the perichondria layer of the developing digits of the forelimb and rib in 16 day embryos. Hybridization was also detected in the outer root sheath of the hair follicles of the upper jaw and in the perichondrium of the vertebrae in these 16 day embryos. In 15 day embryos, hybridization was detected in the perichondrium of the iliac bone in addition to the perichondrium of the ribs and vertebrae. These signals were detected in at least two separate hybridization experiments, however, the signal was not always detected in these structures. The detection of signals seemed to depend on the level of the section in the embryo.

Thus, the precise embryonic regions in which FACC is expressed have not yet been completely defined. In all hybridization experiments, hybridization with the positive control probe HOX10 was always observed and negative controls included for each slide were consistently negative.

The results of these experiments indicate that while the expression of the mouse Facc gene in early embryos (8-13 days) is uniform, or at least not highly localized, a significant level of expression was seen in the developing bone and hair follicles. This is surprising since the human defect in skeletal development resulting in short stature, microphthalmia and radial ray anomalies would be expected to result from a loss of expression of the gene as detected earlier in the development of the mouse embryo. Two possible explanations can be presented to explain the expression in developing bone. The first is that the Facc protein performs a second function in addition to a general role in protection against or repair of DNA damage, and that the loss of this function in human FA patients is insufficient to cause a detectable phenotype directly related to bone development or differentiation. The second is that the Facc protein plays a single role in protection against or repair of DNA damage, including a role in growth or differentiation, which is reflected in its expression in differentiating cells forming the bone.

Notably, these preliminary experiments do not indicate that there is a significant increase in the expression of the gene during the critical period of organogenesis, between days 9 and 11 of embryo development. This result may be interpreted to mean that the gene is expressed at a constitutive level at this time, despite the particularly acute susceptibility of the organism to effects of teratogenis during organogenesis. Thus, loss of Facc protein function may increase the susceptibility to such a level that the defenses of the embryo are overwhelmed (perhaps due to the influence of other genes, environmental factors, or loss of heterozygosity due to DNA damage), resulting in a variety of congenital malformations.

While not wishing to be bound by speculation, it may be suggested that the embryonic expression studies indicate the possibility that genes involved in Fanconi anemia are not merely required in every cell for the maintenance of DNA during all stages of development, but are instead involved in the complex regulation of cell growth or differentiation.

The mouse is an extremely useful experimental organism, particularly with respect to transgenic technology. The cloning of the mouse FA homolog should permit the generation of a mouse model for FA by targeted gene replacement in mouse embryonic stem cells (Sedivy and Joyner, 1992, herein incorporated by reference). This in turn, will facilitate the study of the abnormal developmental and hematopoietic processes leading to the pleiotropic phenotype of Fanconi Anemia. Furthermore, the full cross-species complementation of the mouse Facc gene, in spite of the relatively low protein homology, may indicate that the proteins involved in the protection against DNA cross linking agents are not completely interdependent in structure. This suggests that methods using heterologous cDNA or DNA to clone the other FA genes may be successful. Additionally, the presence of cross hybridizing sequences in genomic DNA from chicken and Drosophila indicates that FA equivalents may exist in these species. In fact, a Drosophila mutant (Mus308) with similar cellular characteristics to FA group A has been described (Boyd et al., 1990). Cloning of FA(C) homologs from other species may also enable the identification of regions of sequence conservation indicative of function, which are presently difficult to define with the limited data available.

Having illustrated and described the principles of isolating the mouse Facc cDNA, and having provided the nucleotide sequence of this cDNA and the amino acid sequence of the Facc protein encoded by this cDNA, it will be apparent that the methodologies and applications described for the human FACC cDNA, the human genomic FA(C) gene and the human FACC protein in Examples 5-13 apply to the mouse Facc cDNA, the mouse genomic FAC(C) gene and the Facc protein. Thus, for example, it will now be possible to clone the mouse genomic gene from which the mouse Facc cDNA is derived and to express and purify the mouse Facc protein and to make antibodies to this protein.

Having illustrated and described the principles of isolating the human FACC cDNA and the mouse Face cDNA, their corresponding genomic genes, the FACC and Facc proteins and modes of use of these biological molecules, it should be apparent to one skilled in the art that the invention can be modified in arrangement and detail without departing from such principles. We claim all modifications coming within the spirit and scope of the claims presented herein.

BIBLIOGRAPHY

Ahmad et al. (1986). *J. Virol.* 57:267.

Amann and Brosius (1985). *Gene* 40:183.

Alt et al. (1978). *J. Biol. Chem.* 253:1357.

Arwert and Kwee (1989). In *Fanconi Anemia: clinical, cytogenetic, and Experimental Aspects*, 83–92 Schroeder-Kurth et al. (eds.), Springer-Verlag, Berlin.

Auerbach and Wolman (1978). *Nature* 271:69–70.

Auerbach et al. (1989a). *Blood* 73:391–396.

Auerbach et al. (1989b). In *Fanconi Anemia: Clinical, Cytogenetic, and Experimental Aspects*, 71–82 Schroeder-Kurth et al. (eds.), Springer-Verlag, Berlin.

Ausubel et al. (1987). In *Current protocols in Molecular Biology*, Greene Publishing Associates and Wiley-Intersciences.

Belt et al. (1989). *Gene* 84:407–417.

Bentley et al. (1992). *Genomics* 12:534–541.

Berger et al. (1980). *Cancer Genet. Cytogenet.* 2:259–267.

Bernstein et al. (1985). *Gen. Engr'g* 7:235.

Bolton and McCarthy (1962). *Proc. Natl. Acad. Sci. USA* 48:1390.

Bonner et al. (1973). *J. Mol. Biol.* 81:123.

Boyd et al. (1990). *Genetics* 125:813–819.

Bradley et al. (1988). *BioTechniques* 6:114–116.

Brash et al. (1987). *Mol. Cell Biol.* 7:2013.

Breathnach and Chambon (1981). *Ann. Rev. Biochem.* 50:349–383.

Buchwald et al. (1989). In *Fanconi Anaemia: Clinical, Cytogenetic, and Experimental Aspects* 226–235, Schroeder-Kurth et al. (eds.), Springer-Verlag, Berlin.

Buchwald et al. (1987). *Mutation Res.* 184:153–159.

Burke et al. (1987). *Science* 236:806–812.

Caskey (1987). *Science* 236:1223–1228.

Cervenka et al. (1981). *Pediatrics* 67:119–127.

Chamberlain et al. (1988). *Nucl. Acids Res.* 16:1141–1155 (1988).

Church and Gilbert (1988). *Proc. Natl. Acad. Sci. USA* 81:1991–1995.

Cotton et al. (1985). *Proc. Natl. Acad. Sci. USA* 85:4397–4401.

Dallapiccola and Porfirio (1989). In *Fanconi Anaemia: Clinical, Cytogenetic, and experimental Aspects* 145–158, Schroeder-Kurth et al. (eds.), Springer-Verlag, Berlin.

Duckworth-Rysiecki et al. (1985). *Somatic. Cell. Mol. Genet.* 11:35–41.

Ebell et al. (1989). In *Fanconi Anaemia: Clinical, Cytogenetic, and Experimental Aspects* 47–59, Schroeder-Kurth et al. (eds.), Springer-Verlag, Berlin.

Eisenberg (1984). *Annu. Rev. Biochem.* 53:595–623.

Engvall (1980). *Enzymol.* 70:419.

Felgner et al. (1987). *Proc. Natl. Acad. Sci USA* 84:7413.

Fisher (1980). *Manual of clinical Immunology*, ch. 42.

Flavell et al. (1978). *Cell* 15:25.

Gasser and Fraley (1989). *Science* 244:1293.

Gebeyehu et al. (1987). *Nucleic Acids Res.* 15:4513–4534.

Geever et al. (1981). *Proc. Natl. Acad. Sci USA* 78:5081.

Glade and Broder (1971). In *In Vitro Methods in Cell Mediated Immunity* 561–570, Bloom, B. R. and Glade, P. R. (eds.), Academic Press, New York.

Glanz and Fraser (1982). *J. Med. Genet.* 9:412–416.

Gluckman et al. (1989). In *Fanconi Anaemia: Clinical, Cytogenetic, and Experimental Aspects* 60–68, Schroeder-Kurth et al. (eds.), Springer-Verlag, Berlin.

Gluzman (1981). *Cell* 23:175–182.

Gordon-Smith and Rutherford (1991). *Sem. In Hemat.* 28:104–112.

Gorman et al. (1982). *Proc. Natl. Acad. Sci USA* 78:6777–6781.

Graham and vander Eb (1973). *Virology* 52:466.

Gray et al. (1982). *Proc. Natl. Acad. Sci. USA* 79:6598.

Green et al. (1989). *EMBO J.* 8:1067–1072.

Groger et al. (1989). *Gene* 81:285–294.

Harlow and Lane (1988). *Antibodies, A Laboratory Manual*, Cold Spring Harbor Laboratory, New York.

Harnden and Klinger (1985). *An International System for Human Cytogenetic Nomenclature*, published in collaboration with Cytogenetics and Cell Genetics, Karger, Basel.

Harper and Saunders (1981). *Chromosoma* 83:431–439.

Innis et al. (1990). *PCR Protocols, A Guide to Methods and Applications*, Innis et al. (eds.), Academic Press, Inc., San Diego, Calif.

Jaspers et al. (988). *Cytogenet. Cell Genet.* 49:259–263.

Kawasaki et al. (1990). In *PCR Protocols, A Guide to Methods and Applications*, Innis et al. (eds.), 21–27, Academic Press, Inc., San Diego, Calif.

Klein et al. (1987). *Nature* 327:70.

Kohler and Milstein (1975). *Nature* 256:495.

Kozak (1987). *Nucleic Acids Res.* 15:8125–8148.

Kriegler (1990). In *Gene Transfer and Expression*, 131–132, Stockton Press, New York.

Landegren et al. (1988). *Science* 242:229–237.

Landegren et al. (1988). *Science* 241:1077.

Lee et al. (1982). *Nature* 294:228.

Leeder et al. (1989). *Anal. Biochem.* 177:364–372.

Lin et al. (1985). *Cytogenet. Cell Genet.* 39:269–274.

Liu et al. (1992). *Am. J. Hum. Genet.* 51:A55.

Mann et al. (1991). *Genomics* 9:329–337.

Margolskee et al. (1988). *Mol. Cell. Biol.* 8:2837–2847.

McCabe (1990). In *PCR Protocols, A Guide to Methods and Applications*, Innis et al. (eds.), 76–83, Academic Press, New York.

McCuthan et al. (1968). *J. Natl. Cancer Inst.* 41:351.

McIntosh et al. (1979). *Am, J. Pediatr. Hematol. Oncol.* 1:107–110.

McLaughlin et al. (1988). J. Virol. 62:1963.

Monaco and Lehrach (1991). *Proc. Natl. Acad. Sci. U.S.A.* 88:4123–4127.

Montandon et al. (1989). *Nucleic Acids Res.* 9:3347–3358.

Moss et al. (1987). *Annu. Rev. Immunol.* 5:305.

Moustacchi et al. (1987). *Hum. Genet.* 75:45–47.

Mueller et al. (1978). *Cell* 15:579.

Mulligan and Berg (1981). *Proc. Natl. Acad. Sci. USA* 78:2072–2076.

Mulligan et al. (1981). *Proc. Natl. Acad. Sci. USA* 78:1078–2076.

Myers and Maniatis (1986). *Cold Spring Harbor Symp. Quant. Biol.* 51:275–284.

Myers et al. (1985). *Science* 230:1242.

Nagamine et al. (1989). *Am. J. Hum. Genet.* 45:337–339.

Nakamura et al. (1987). *Science* 235:1616–1622.

Neumann et al. (1982). *EMBO J* 1:841.

Orita et al. (1989). *Genomics* 5:874–879.

Orkin et al. (1988). *Prog. Med. Genet.* 7:130.

Ouchterlony et al. (1973). In *Handbook of Experimental Immunology*, Wier, D. (ed.) chapter 19. Blackwell.

Petridon and Barrett (1990). *Acta Pardiatr. Scand.* 79:1069–1074.

Proudfoot (1991). *Cell* 64:671–674.

Pursel et al. (1989). *Science* 244:1281–1288.

Rasmussen et al. (1987). *Methods Enzymol.* 139:642.

Riley et al. (1990). *Nucleic Acids Res.* 18:2887–2890.

Roberts et al. (1992). *Genomics* 13:942–950.

Rosenberg et al. (1990). *N. Engl. J. Med.* 323:570–578.

Rousset et al. (1990). *Cancer Res.* 50:2443–2448.

Ruther and Muller-Hill (1983). *EMBO J.* 2:1791.

Saiki et al. (1989). *Proc. Nat. Acad. Sci. USA* 86:6230–6234.

Sambrook et al. (1989). In *Molecular Cloning: A Laboratory Manual*, Cold Spring Harbor, N.Y.

Sanford et al. (1987). *Particulate Sci. Technol.* 5:27–37.

Sanger et al. (1977). *Proc. Natl. Acad. Sci. U.S.A.* 74:5463.

Santerre et al. (1984). *Gene* 30:147–156.

Sarver et al. (1981). *Mol. Cell Biol.* 1:486.

Schafner (1980). *Proc. Natl. Acad. Sci. USA* 77:2163–2167.

Schroeder et al. (1976). *Hum. Genet.* 32:257–288.

Schroeder et al. (1964). *Hum. Genet.* 1:194–196.

Sedivy and Joyner (1992). In *Gene Targeting*, W. H. Freeman and Company, New York.

Shapiro and Senapathy (1987). *Nucleic Acids Res.* 15:7155–7174.

Shimatake and Rosenberg (1981). *Nature* (London) 292:128.

Southern (1975). *J. Mol. Biol.* 98:503.

Southern and Berg (1982). *J. Mol. Appl. Genet.* 1:327–341.

Spaete et al. (1982). *Cell* 30:295.

Stanley and Luzio (1984). *EMBO J.* 3:1429.

Stanners et al. (1971). *Nature New Biology* 230:52–54.

Stoflet et al. (1988). *Science* 239:491–494.

Studiar and Moffatt (1986). *J. Mol. Biol.* 189:113.

Sugden et al. (1985). *Mol. Cell Biol.* 5:410.

Summers and Smith (1985). In *Genetically Altered Viruses and the Environment*, Fields et al. (Eds.) 22:319–328, Cold Spring Harbor Laboratory Press, Cold Spring Harbor, N.Y.

Swift (1971). *Nature* 230:370–373.

Szybalski and Iyer (1967). In *Antibiotics, Vol. 1. Mechanisms of Action* 211–245, Springer-Verlag, New York.

Tanaka et al. (1989). *Proc. Natl. Acad. Sci. USA* 86:5512–5516.

Tang et al. (1992). *Nature* (London) 356:152–154.

Timberlake and Marshall (1989). *Science* 244:1313–1317.

Trezise and Buchwald (1991). *Nature* 353:434–437.

Tsui and Estevill (1991). In *Genes and Phenotypes* 1–36, Cold Spring Harbor Laboratory Press, Cold Spring Harbor, N.Y.

Vaitukaitis et al. (1971). *J. Clin. Endocrinol. Metab.* 33:988–991.

Van Duuren (1969). *Ann. N.Y. Acad. Sci.* 163:633–651.

Veres et al. (1987). *Science* 237:415–417.

Vermeulen et al. (1991). *Mutation Res.* 255:201–208.

Wallace et al. (1986). *Cold Spring Harbor Symp. Quant. Biol.* 51:257–261.

Ward and Langer et al. (1981). Proc. Natl. Acad. Sci. USA 78:6633–6657.

Winship, P. R. (1989). *Nucleic Acids Res.* 17:1266.

Wong et al. (1987). *Nature* 330:384–386.

Wrichnik et al. (1987). *Nucleic Acids Res.* 15:529–542.

---

We claim:

1. An isolated DNA molecule selected from the group consisting of:

(a) a DNA molecule having a nucleotide sequence encoding an amino acid sequence as shown in Seq. ID No. 4;

(b) a DNA molecule capable of specific hybridization under stringent conditions to a DNA molecule according to (a), and which encodes a protein that, when introduced into cells from patients with Fanconi Anemia of Complementation group C, reduces the sensitivity of those cells to mitomycin C;

(c) a DNA molecule capable of specific hybridization under stringent conditions to a DNA molecule according to (a), and which encodes a protein that, when introduced into cells from patients with Fanconi Anemia of Complementation group C, reduces the sensitivity of those cells to diepoxybutane;

(d) a DNA molecule having a nucleotide sequence which is degenerate as a result of the genetic code to the encoded protein amino acid sequence according to (b), and which encodes a protein that, when introduced into cells from patients with Fanconi Anemia of Complementation group C, reduces the sensitivity of those cells to mitomycin C; and (e) a DNA molecule having a nucleotide sequence which is degenerate as a result of the genetic code to the encoded protein amino acid sequence according to (c), and which encodes a protein that, when Complementation group C, reduces the sensitivity of those cells to diepoxybutane.

2. A DNA molecule according to part (b) or (c) of claim 1 wherein the DNA molecule is capable of specifically hybridizing to a DNA molecule according to part (a) of claim 1 under conditions wherein DNA sequences with more than 25% mismatch will not hybridize to each other.

3. A DNA molecule according to part (b) or (c) of claim 1 wherein the DNA molecule is capable of specifically hybridizing to a DNA molecule of part (a) of claim 1 under conditions wherein DNA sequences with more than 10% mismatch will not hybridize to each other.

4. An isolated DNA molecule having a sequence selected from the group consisting of:

(a) the nucleotide sequences shown in Seq. I.D. Nos. 5–30; and (b) the complementary strand of said nucleotide sequences.

5. An oligonucleotide consisting of at least 15 consecutive nucleotides of a DNA sequence selected from the group consisting of the nucleotide sequences shown in Seq. I.D. Nos. 5–30, and the complementary strands of said nucleotide sequences.

6. An oligonucleotide capable of specifically hybridizing to a nucleic acid molecule encoding an amino acid sequence as shown in Seq. ID No. 4, the oligonucleotide consisting of at least 15 consecutive nucleotides of a DNA sequence selected from the group consisting of the DNA sequences set forth in Seq. I.D. Nos. 1, 2 and 3 and the complementary strands of said DNA sequences.

7. An isolated DNA molecule having a nucleotide sequence selected from the group consisting of:

(a) nucleotide Nos. 311–1983 set forth in Seq. I.D. No. 31;

(b) nucleotide Nos. 311–2092 set forth in Seq. I.D. No. 32; and (c) the complementary strand of a nucleotide sequence according to (a) or (b).

8. An isolated DNA molecule having a nucleotide sequence encoding an amino acid sequence as shown in Seq. ID No. 4.

9. An isolated DNA molecule capable of specifically hybridizing under stringent conditions to a DNA molecule according to claim 8 and which encodes a protein that, when introduced into cells from patients with Fanconi Anemia of Complementation group C, reduces the sensitivity of those cells to diepoxybutane.

10. An isolated DNA molecule capable of specifically hybridizing under stringent conditions to a DNA molecule according to claim 8 and which encodes a protein that, when introduced into cells from patients with Fanconi Anemia of Complementation group C, reduces the sensitivity of those cells to mitomycin C.

11. An oligonucleotide according to claim 5 wherein the oligonucleotide consists of at least 25 consecutive nucleotides of a DNA sequence selected from the group consisting of DNA sequences shown in Seq. I.D. Nos. 5–30 and the complementary strands of said DNA sequences.

12. An oligonucleotide according to claim 6 wherein the oligonucleotide consists of at least 25 consecutive nucleotides of a DNA sequence selected from the group consisting of DNA sequences shown in Seq. I.D. Nos. 1, 2 and 3 and the complementary strands of said DNA sequences.

13. An oligonucleotide consisting of at least 15 consecutive nucleotides of a DNA molecule according to claim 7.

14. An oligonucleotide according to claim 13 wherein the oligonucleotide consists of at least 25 consecutive nucleotides of a DNA molecule according to claim 7.

* * * * *